(12) United States Patent
Carter et al.

(10) Patent No.: US 10,927,380 B2
(45) Date of Patent: Feb. 23, 2021

(54) OLIGONUCLEOTIDES COMPRISING MODIFIED NUCLEOSIDES

(71) Applicant: SOMALOGIC, INC., Boulder, CO (US)

(72) Inventors: Jeff Carter, Boulder, CO (US); Bharat Gawande, Boulder, CO (US); Nebojsa Janjic, Boulder, CO (US); Daniel Schneider, Boulder, CO (US)

(73) Assignee: SOMALOGIC, INC., Boulder, CO (US)

( * ) Notice: Subject to any disclaimer, the term of this patent is extended or adjusted under 35 U.S.C. 154(b) by 0 days.

(21) Appl. No.: 16/307,520

(22) PCT Filed: Jun. 30, 2017

(86) PCT No.: PCT/US2017/040299
§ 371 (c)(1),
(2) Date: Dec. 6, 2018

(87) PCT Pub. No.: WO2018/005974
PCT Pub. Date: Jan. 4, 2018

(65) Prior Publication Data
US 2019/0177730 A1 Jun. 13, 2019

Related U.S. Application Data

(60) Provisional application No. 62/437,592, filed on Dec. 21, 2016, provisional application No. 62/357,623, filed on Jul. 1, 2016.

(51) Int. Cl.
| C07H 21/02 | (2006.01) |
| C07H 21/04 | (2006.01) |
| C12N 15/115 | (2010.01) |
| C12N 15/11 | (2006.01) |
| C12N 15/10 | (2006.01) |
| C12Q 1/6876 | (2018.01) |

(52) U.S. Cl.
CPC ........ *C12N 15/115* (2013.01); *C12N 15/1048* (2013.01); *C12N 15/111* (2013.01); *C12Q 1/6876* (2013.01); *C12N 2310/16* (2013.01); *C12N 2310/334* (2013.01); *C12N 2310/335* (2013.01); *C12N 2310/3341* (2013.01); *C12N 2330/31* (2013.01)

(58) Field of Classification Search
CPC .............................. A61K 45/06; C12N 2310/16
See application file for complete search history.

(56) References Cited

U.S. PATENT DOCUMENTS

| 7,517,646 B2 | 4/2009 | Fujihara et al. |
| 8,080,649 B2 | 12/2011 | Miyakawa et al. |
| 8,299,225 B2 | 10/2012 | Fujihara |
| 8,889,843 B2 | 11/2014 | Fujihara |
| 8,940,879 B2 | 1/2015 | Fujihara et al. |
| 2014/0213636 A1* | 7/2014 | Lee .................. A61P 35/02 514/44 R |
| 2015/0125867 A1* | 5/2015 | Ochsner ............ G01N 33/573 435/6.12 |

FOREIGN PATENT DOCUMENTS

| EP | 1489171 B1 | 10/2012 |
| RU | 2401306 C2 | 10/2010 |
| RU | 2460794 C2 | 9/2012 |
| WO | 2009012410 A1 | 1/2009 |
| WO | 2009012418 A2 | 1/2009 |
| WO | 2011109642 A1 | 9/2011 |
| WO | 2011129494 A1 | 10/2011 |
| WO | 2013149086 A1 | 10/2013 |
| WO | 2015048084 A1 | 4/2015 |
| WO | 2015077292 A1 | 5/2015 |
| WO | 2016069461 A1 | 5/2016 |

OTHER PUBLICATIONS

Gold et al. (PLoS One, 2010, 5(12), 1-17).*
Gold et al., "Aptamer-Based Multiplexed Proteomic Technology for Biomarker Discovery," PLoS One, 5(12):e15004, 32 pages, 2010.
Vaught et al., "Expanding the Chemistry of DNA for in vitro Selection," J. Am. Chem. Soc., 132(12):4141-4151, 2010.
Stovall et al., "In Vitro Selection Using Modified or Unnatural Nucleotides," Current Protocols in Nucleic Acid Chemistry, 9.6.1-33, 2014.
Davies et al., "Unique motifs and hydrophobic interactions shape the binding of modified DNA ligands to protein targets," PNAS, 109(49):19971-19976, 2012.
Eaton et al., "Post-SELEX Combinatorial Optimization of Aptamers," Bioorganic & Medicinal Chemistry, 5(6):1087-1096, 1997.
Gawande et al., "Selection of DNA aptamers with two modified bases," PNAS, 114(11):2898-2903, 2017.
Gupta et al., "An evaluation of an aptamer for use as an affinity reagent with MS: PCSK9 as an example protein," Bioanalysis, 8(15):1557-1564, 2016.
International Search Report and Written Opinion issued in International Application No. PCT/US2017/040299, dated Dec. 8, 2017, 25 pages.
Gupta et al., "Chemically Modified DNA Aptamers Bind Interleukin-6 with High Affinity and Inhibit Signaling by Blocking its Interaction with Interleukin-6 Receptor," J. Biol. Chem., 289(12):8706-8719, 2014.
Fujita et al., "Novel Protein Detection System Using DNA as Constituent Material," Sci. Tech. J., 48(2):237-243, Apr. 2012.
Russian Search Report issued in RU2019102588, dated Nov. 30, 2020, including English translation, 6 pages.

* cited by examiner

Primary Examiner — Amy H Bowman
(74) Attorney, Agent, or Firm — McNeill Baur PLLC

(57) ABSTRACT

Polynucleotides, such as aptamers, comprising at least first one 5-position modified pyrimidine and at least one second 5-position modified pyrimidine are provided, wherein the first and second 5-position modified pyrimidines are different. Methods of selecting and using such polynucleotides, such as aptamers, are also provided.

19 Claims, 32 Drawing Sheets

Specification includes a Sequence Listing.

CYTOSINE                             URACIL

∿∿∿ - denotes attachment to backbone of nucleic acid molecules (e.g., phosphate deoxyribose backbone)

X - denotes a linker attached to the 5-position of the pyrimidine molecule (uracil or cytosine)

R' - denotes a moiety attached to the 5-position of the pyrimdine molecule via the linker (X)

Exemplary Linkers (denoted as X in Figure 20, above)
n = 0, 1, 2, 3, 4, 5, 6, 7, 8, 9 or 10; R' denotes a moiety
∽ - denotes attachment to the 5-position of the pyrimidine molecule (uracil or cytosine)

| Group | R' Structures (* denotes the point of attachment of the R' group to X (linker)) |
|---|---|
| I |  |
| II |  |
| III |  |
| IV |  |
| V |  |
| VI |  |
| VII |  |
| VIII |  |
| IX |  |
| X |  |

| Group | R' Structures (* denotes the point of attachment of the R' group to X (linker)) |
|---|---|
| XI | (anthracenyl, phenanthrenyl, and phenanthrenyl isomer structures with *) |
| XII | cyclopropyl*, cyclopentyl*, cyclohexyl* |
| XIII | *−CH₃, H₃C−CH*−CH₃, H₃C−CH*−CH₂−CH₃, H₃C−C*(CH₃)(CH₃) with H₃C |
| XIV | *−CH₂−OH, *−CH(OH)−CH₃, *−C(OH)(CH₃)(H₃C) |
| XV | *−CH₂−OR'', *−CH(OR'')−CH₃, *−C(OR'')(CH₃)(H₃C), *−CH₂−O−CH₂−CH₂−O−CH₃ |
| XVI | *−CH₂−SR'', *−CH(SR'')−CH₃, *−C(SR'')(CH₃)(H₃C) |
| XVII | *−CH₂−N⁺(R'')(R'')(R''), *−CH(N⁺R''R''R'')−CH₃, *−C(N⁺R''R'')(CH₃)(H₃C) |
| XVIII | *−C(=O)OH, *−C(=O)OR'', *−C(=O)NH₂, *−C(=O)NHR'', *−C(=O)NR''R''' |
| XIX | *−C(=N)NH₂, *−C(=N)NHR'', *−C(=N)NR''R''', *−C(=NR'')NHR'', *−C(=NR'')NR''R''' |
| XX | *−CH(=O), *−C(=O)CH₃, *−CH(=NOH), *−C(=NOH)CH₃, *−CH(=NOR''), *−C(=NOR'')CH₃ |

R''' and R'''' are, independently, selected from a halogen (-F, -Cl, -Br, -I); nitrile (-CN); -NH₂; -OH; branched lower alkyl (C1-C20); linear lower alkyl (C1-C20); primary amide; secondary amide; tertiary amide; and alkoxy group.

*FIG. 20 (cont.)*

| Abbreviation | 5-dU Modification Attached via Amide Linkage | Chemical Structure |
|---|---|---|
| Bn | benzylmethyl | 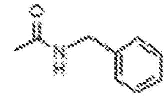 |
| Nap | *1*-naphthylmethyl | 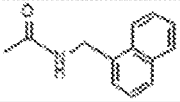 |
| PE | *2*-phenylethyl | 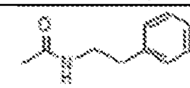 |
| PP | *3*-phenylpropyl | 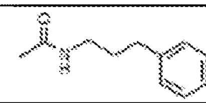 |
| iBu | *iso*-butyl | 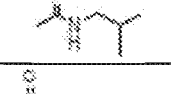 |
| FBn | *4*-fluorobenzylmethyl | 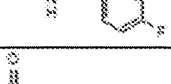 |
| 2Nap | *2*-naphthylmethyl | 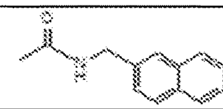 |
| Tyr | tyrosyl | 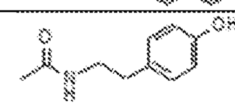 |
| NE | *1*-naphthylethyl | 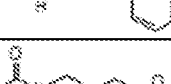 |
| MBn | 3,4-methylenedioxy benzyl | 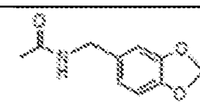 |
| MOE | morpholinoethyl | 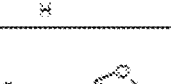 |
| BF | 3-benzofuranylethyl | 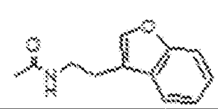 |
| BT | 3-benzothiophenylethyl | 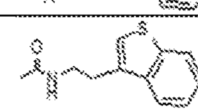 |
| Trp | 3-indole-2-ethyl | 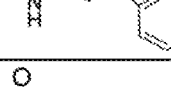 |
| Thr | (R)-2-hydroxypropyl | 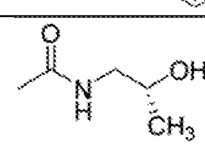 |

*FIG. 21*

| Abbreviation | 5-dC Modification Attached via Amide Linkage | Chemical Structure |
| --- | --- | --- |
| Bn | *1*-benzylmethyl | 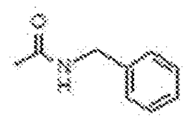 |
| Nap | *1*-naphthylmethyl | 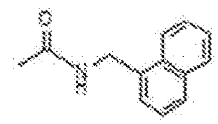 |
| PE | *2*-phenylethyl | 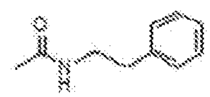 |
| PP | *3*-phenylpropyl | 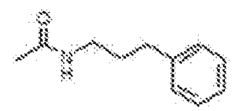 |
| 2Nap | *2*-naphthylmethyl | 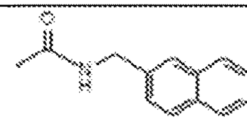 |
| Tyr | tyrosyl | 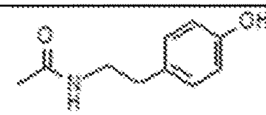 |
| NE | *1*-naphthylethyl | 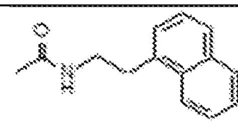 |
| 2NE | *2*-naphthyl-2-ethyl | 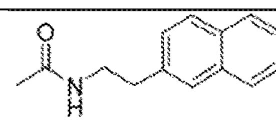 |

*FIG. 22*

OLIGONUCLEOTIDES COMPRISING MODIFIED NUCLEOSIDES

CROSS-REFERENCE TO RELATED APPLICATIONS

This application is a national phase entry pursuant to 35 U.S.C. § 371 of International Application No. PCT/US2017/040299, filed Jun. 30, 2017, which claims the benefit of priority of U.S. Provisional Application No. 62/357,623, filed Jul. 1, 2016, and U.S. Provisional Application No. 62/437,592, filed Dec. 21, 2016, each of which is incorporated by reference herein in its entirety for any purpose.

SEQUENCE LISTING

This application contains a Sequence Listing, which has been submitted electronically in ASCII format and is hereby incorporated by reference in its entirety. Said ASCII copy, created on Jun. 15, 2017, is named 01137-0020-00PCT_SL.txt and is 21,863 bytes in size.

FIELD

The present disclosure relates generally to the field of oligonucleotides comprising modified nucleosides, such as aptamers that are capable of binding to target molecules. In some embodiments, the present disclosure relates to oligonucleotides, such as aptamers, that comprise more than one type of base-modified nucleoside, and methods of making and using such aptamers.

BACKGROUND

Modified nucleosides have been used as therapeutic agents, diagnostic agents, and for incorporation into oligonucleotides to improve their properties (e.g., stability).

SELEX (Systematic Evolution of Ligands for EXponential Enrichment) is a method for identifying oligonucleotides (referred to as "aptamers") that selectively bind target molecules. The SELEX process is described, for example, in U.S. Pat. No. 5,270,163. The SELEX method involves the selection and identification of oligonucleotides from a random mixture of oligonucleotides to achieve virtually any desired criterion of binding affinity and selectivity. By introducing specific types of modified nucleosides to the oligonucleotides identified in the course of the SELEX process, the nuclease stability, net charge, hydrophilicity or lipophilicity may be altered to provide differences in the three dimensional structure and target binding capabilities of the oligonucleotides.

SUMMARY

In some embodiments, an aptamer comprising at least one first 5-position modified pyrimidine and at least one second 5-position modified pyrimidine is provided, wherein the first 5-position modified pyrimidine and the second 5-position modified pyrimidine are different. In some embodiments, the first 5-position modified pyrimidine is a 5-position modified uridine and wherein the second 5-position modified pyrimidine is a 5-position modified cytidine. In some embodiments, the first 5-position modified pyrimidine is a 5-position modified cytidine and wherein the second 5-position modified pyrimidine is a 5-position modified uridine. In some embodiments, the 5-position modified uridine comprises a moiety at the 5-position selected from a naphthyl moiety, a benzyl moiety, a tyrosyl moiety, an indole moiety and a morpholino moiety. In some embodiments, the 5-position modified cytidine comprises a moiety at the 5-position selected from a naphthyl moiety, a benzyl moiety, a tyrosyl moiety, and a morpholino moiety. In certain embodiments, the moiety is covalently linked to the 5-position of the base via a linker comprising a group selected from an amide linker, a carbonyl linker, a propynyl linker, an alkyne linker, an ester linker, a urea linker, a carbamate linker, a guanidine linker, an amidine linker, a sulfoxide linker, and a sulfone linker. In some embodiments, the 5-position modified cytidine is selected from NapdC, 2NapdC, TyrdC, and PPdC. In some embodiments, the 5-position modified uridine is selected from NapdU, 2NapdU, PPdU, MOEdU, TyrdU, TrpdU, and ThrdU. In some embodiments, the at least one first 5-position modified pyrimidine is a NapdC and the at least one second 5-position modified pyrimidine is selected from NapdU, 2NapdU, PPdU, MOEdU, TyrdU, and ThrdU. In some embodiments, the at least one first 5-position modified pyrimidine is a PPdC and the at least one second 5-position modified pyrimidine is selected from NapdU, 2NapdU, PPdU, MOEdU, TyrdU, TrpdU, and ThrdU. In some embodiments, the at least one second 5-position modified pyrimidine is a TyrdU. In some embodiments, the first 5-position modified pyrimidine and the second 5-position modified pyrimidine are capable of being incorporated by a polymerase enzyme. In some embodiments, the first 5-position modified pyrimidine and the second 5-position modified pyrimidine are capable of being incorporated by a KOD DNA polymerase.

In some embodiments, the aptamer binds a target protein selected from PCSK9, PSMA, ErbB1, ErbB2, FXN, KDM2A, IGF1R, pIGF1R, a1-Antritrypsin, CD99, MMP28 and PPIB.

In some embodiments, the aptamer comprises a region at the 5' end of the aptamer that is at least 10, at least 15, at least 20, at least 25 or at least 30 nucleotides in length, or 5 to 30, 10 to 30, 15 to 30, 5 to 20, or 10 to 20 nucleotides in length, wherein the region at the 5' end of the aptamer lacks 5-position modified pyrimidines. In some embodiments, the aptamer comprises a region at the 3' end of the aptamer that is at least 10, at least 15, at least 20, at least 25 or at least 30 nucleotides in length, or 5 to 30, 10 to 30, 15 to 30, 5 to 20, or 10 to 20 nucleotides in length, wherein the region at the 3' end of the aptamer lacks 5-position modified pyrimidines. In some embodiments, the aptamer is 20 to 100, or 20 to 90, or 20 to 80, or 20 to 70, or 20 to 60, or 20 to 50, or 30 to 100, or 30 to 90, or 30 to 80, or 30 to 70, or 30 to 60, or 30 to 50, or 40 to 100, or 40 to 90, or 40 to 80, or 40 to 70, or 40 to 60, or 40 to 50 nucleotides in length.

In some embodiments, the aptamer has improved nuclease stability compared to an aptamer of the same length and nucleobase sequence that comprises an unmodified pyrimidine in place of each of the first 5-position modified pyrimidines and/or an unmodified pyrimidine in place of each of the second 5-position modified pyrimidine. In some embodiments, the aptamer has a longer half-life in human serum compared to an aptamer of the same length and nucleobase sequence that comprises an unmodified pyrimidine in place of each of the first 5-position modified pyrimidines or an unmodified pyrimidine in place of each of the second 5-position modified pyrimidine.

In some embodiments, a composition comprising a plurality of polynucleotides is provided, wherein each polynucleotide comprises at least one first 5-position modified pyrimidine and at least one second 5-position modified pyrimidine, wherein the first 5-position modified pyrimidine and the second 5-position modified pyrimidine are different. In some embodiments, each polynucleotide comprises a fixed region at the 5' end of the polynucleotide. In some embodiments, the fixed region at the 5' end of each polynucleotide is at least 10, at least 15, at least 20, at least 25 or at least 30 nucleotides in length, or 5 to 30, 10 to 30, 15 to 30, 5 to 20, or 10 to 20 nucleotides in length. In some embodiments, each polynucleotide comprises a fixed region at the 3' end of the polynucleotide. In some embodiments, the fixed region at the 3' end of the polynucleotide is at least 10, at least 15, at least 20, at least 25 or at least 30 nucleotides in length, or 5 to 30, 10 to 30, 15 to 30, 5 to 20, or 10 to 20 nucleotides in length. In some embodiments, the first 5-position modified pyrimidine is a 5-position modified uridine and wherein the second 5-position modified pyrimidine is a 5-position modified cytidine. In some embodiments, the first 5-position modified pyrimidine is a 5-position modified cytidine and wherein the second 5-position modified pyrimidine is a 5-position modified uridine. In some embodiments, the 5-position modified uridine comprises a moiety at the 5-position selected from a naphthyl moiety, a benzyl moiety, a tyrosyl moiety, a tryptophanyl moiety, an indole moiety and a morpholino moiety. In some embodiments, the 5-position modified cytidine comprises a moiety at the 5-position selected from a naphthyl moiety, a benzyl moiety, a tyrosyl moiety and a morpholino moiety. In certain embodiments, the moiety is covalently linked to the 5-position of the base via a linker comprising a group selected from an amide linker, a carbonyl linker, a propynyl linker, an alkyne linker, an ester linker, a urea linker, a carbamate linker, a guanidine linker, an amidine linker, a sulfoxide linker, and a sulfone linker. In some embodiments, the 5-position modified cytidine is selected from NapdC, 2NapdC, TyrdC, and PPdC. In some embodiments, the 5-position modified uridine is selected from NapdU, PPdU, MOEdU, TyrdU, TrpdU, and ThrdU. In some embodiments, the at least one first 5-position modified pyrimidine is a NapdC and the at least one second 5-position modified pyrimidine is selected from NapdU, 2NapdU, PPdU, MOEdU, TyrdU, TrpdU, and ThrdU. In some embodiments, the at least one first 5-position modified pyrimidine is a PPdC and the at least one second 5-position modified pyrimidine is selected from NapdU, 2NapdU, PPdU, MOEdU, TrydU, TrpdU, and ThrdU. In some embodiments, the at least one second 5-position modified pyrimidine is a TyrdU. In some embodiments, the first 5-position modified pyrimidine and the second 5-position modified pyrimidine are capable of being incorporated by a polymerase enzyme. In some embodiments, the first 5-position modified pyrimidine and the second 5-position modified pyrimidine are capable of being incorporated by a KOD DNA polymerase.

In some embodiments, each polynucleotide of the composition comprises a random region. In some embodiments, the random region is 20 to 100, or 20 to 90, or 20 to 80, or 20 to 70, or 20 to 60, or 20 to 50, or 20 to 40, or 30 to 100, or 30 to 90, or 30 to 70, or 30 to 60, or 30 to 50, or 30 to 40 nucleotides in length. In some embodiments, each polynucleotide is 20 to 100, or 20 to 90, or 20 to 80, or 20 to 70, or 20 to 60, or 20 to 50, or 30 to 100, or 30 to 90, or 30 to 80, or 30 to 70, or 30 to 60, or 30 to 50, or 40 to 100, or 40 to 90, or 40 to 80, or 40 to 70, or 40 to 60, or 40 to 50 nucleotides in length.

In some embodiments, a composition is provided, comprising a first aptamer, a second aptamer, and a target, wherein the first aptamer comprises at least one first 5-position modified pyrimidine and at least one second 5-position modified pyrimidine; wherein the second aptamer comprises at least one third 5-position modified pyrimidine or wherein the second aptamer comprises at least one third 5-position modified pyrimidine and at least one fourth 5-position modified pyrimidine; wherein the first aptamer, second aptamer and the target are capable of forming a trimer complex; and wherein the first 5-position modified pyrimidine and the second 5-position modified pyrimidine are different 5-position modified pyrimidines.

In some embodiments, the first 5-position modified pyrimidine is a 5-position modified uridine and wherein the second 5-position modified pyrimidine is a 5-position modified cytidine. In some embodiments, the first 5-position modified pyrimidine is a 5-position modified cytidine and wherein the second 5-position modified pyrimidine is a 5-position modified uridine. In some embodiments, the 5-position modified uridine comprises a moiety at the 5-position selected from a naphthyl moiety, a benzyl moiety, a tyrosyl moiety, an indole moiety and a morpholino moiety. In some embodiments, the 5-position modified cytidine comprises a moiety at the 5-position selected from a naphthyl moiety, a benzyl moiety, a tyrosyl moiety and a morpholino moiety. In certain embodiments, the moiety is covalently linked to the 5-position of the base via a linker comprising a group selected from an amide linker, a carbonyl linker, a propynyl linker, an alkyne linker, an ester linker, a urea linker, a carbamate linker, a guanidine linker, an amidine linker, a sulfoxide linker, and a sulfone linker. In some embodiments, the 5-position modified cytidine is selected from NapdC, 2NapdC, TyrdC, and PPdC. In some embodiments, the 5-position modified uridine is selected from NapdU, 2NapdU, PPdU, MOEdU, TyrdU, TrpdU, and ThrdU. In some embodiments, the at least one first 5-position modified pyrimidine is a NapdC and the at least one second 5-position modified pyrimidine is selected from NapdU, 2NapdU, PPdU, MOEdU, TyrdU, TrpdU, and ThrdU. In some embodiments, the at least one first 5-position modified pyrimidine is a PPdC and the at least one second 5-position modified pyrimidine is selected from NapdU, 2NapdU, PPdU, MOEdU, TyrdU, TrpdU, and ThrdU. In some embodiments, the at least one second 5-position modified pyrimidine is a TyrdU. In some embodiments, the first 5-position modified pyrimidine and the second 5-position modified pyrimidine are capable of being incorporated by a polymerase enzyme. In some embodiments, the first 5-position modified pyrimidine and the second 5-position modified pyrimidine are capable of being incorporated by a KOD DNA polymerase.

In some embodiments, the third 5-position modified pyrimidine is selected from a 5-position modified cytidine and a 5-position modified pyrimidine. In some embodiments, the third 5-position modified pyrimidine and the fourth 5-position modified pyrimidine are different 5-position modified pyrimidines. In some embodiments, third 5-position modified pyrimidine is a 5-position modified cytidine and the fourth 5-position modified pyrimidine is a 5-position modified uridine. In some embodiments, the third 5-position modified cytidine is selected from BndC, PEdC, PPdC, NapdC, 2NapdC, NEdC, 2NEdC, and TyrdC. In some embodiments, the 5-position modified uridine is selected from BNdU, NapdU, PEdU, IbdU, FBndU, 2NapdU, NEdU, MBndU, BFdU, BTdU, PPdU, MOEdU, TyrdU, TrpdU, and ThrdU.

In some embodiments, the target is selected from a protein, a peptide, a carbohydrate, a small molecule, a cell and a tissue.

In some embodiments, a method is provided, comprising:

(a) contacting an aptamer capable of binding to a target molecule with a sample;

(b) incubating the aptamer with the sample to allow an aptamer-target complex to form;

(c) enriching for the aptamer-target complex in the sample and (c) detecting for the presence of the aptamer, aptamer-target complex or target molecule, wherein the detection of the aptamer, aptamer-target complex or target molecule indicates that the target molecule is present in the sample, and wherein the lack of detection of the aptamer, aptamer-target complex or target molecule indicates that the target molecule is not present in the sample;

wherein the aptamer is a dual-modified aptamer provided herein. In some embodiments, the method comprises at least one additional step selected from: adding a competitor molecule to the sample; capturing the aptamer-target complex on a solid support; and adding a competitor molecule and diluting the sample; wherein the at least one additional step occurs after step (a) or step (b). In some embodiments, the competitor molecule is selected from a polyanionic competitor. In some embodiments, the polyanionic competitor is selected from an oligonucleotide, polydextran, DNA, heparin and dNTPs. In some embodiments, polydextran is dextran sulfate; and DNA is herring sperm DNA or salmon sperm DNA. In some embodiments, the target molecule is selected from a protein, a peptide, a carbohydrate, a small molecule, a cell and a tissue. In some embodiments, the sample is selected from whole blood, leukocytes, peripheral blood mononuclear cells, plasma, serum, sputum, breath, urine, semen, saliva, meningial fluid, amniotic fluid, glandular fluid, lymph fluid, nipple aspirate, bronchial aspirate, synovial fluid, joint aspirate, cells, a cellular extract, stool, tissue, a tissue biopsy, and cerebrospinal fluid.

In some embodiments, a method for detecting a target in a sample is provided, comprising a) contacting the sample with a first aptamer to form a mixture, wherein the first aptamer is capable of binding to the target to form a first complex;

b) incubating the mixture under conditions that allow for the first complex to form;

c) contacting the mixture with a second aptamer, wherein the second aptamer is capable of binding the first complex to form a second complex;

d) incubating the mixture under conditions that allow for the second complex to form;

e) detecting for the presence or absence of the first aptamer, the second aptamer, the target, the first complex or the second complex in the mixture, wherein the presence of the first aptamer, the second aptamer, the target, the first complex or the second complex indicates that the target is present in the sample;

wherein the first aptamer comprises at least one first 5-position modified pyrimidine and at least one second 5-position modified pyrimidine;

wherein the second aptamer comprises at least one third 5-position modified pyrimidine, or wherein the second aptamer comprises at least one third 5-position modified pyrimidine and at least one fourth 5-position modified pyrimidine;

wherein the first 5-position modified pyrimidine and the second 5-position modified pyrimidine are different 5-position modified pyrimidines.

In some embodiments, the first 5-position modified pyrimidine is a 5-position modified uridine and wherein the second 5-position modified pyrimidine is a 5-position modified cytidine. In some embodiments, the first 5-position modified pyrimidine is a 5-position modified cytidine and wherein the second 5-position modified pyrimidine is a 5-position modified uridine. In some embodiments, the 5-position modified uridine comprises a moiety at the 5-position selected from a naphthyl moiety, a benzyl moiety, a tyrosyl moiety, an indole moiety and a morpholino moiety. In some embodiments, the 5-position modified cytidine comprises a moiety at the 5-position selected from a naphthyl moiety, a benzyl moiety, a tyrosyl moiety and a morpholino moiety. In certain embodiments, the moiety is covalently linked to the 5-position of the base via a linker comprising a group selected from an amide linker, a carbonyl linker, a propynyl linker, an alkyne linker, an ester linker, a urea linker, a carbamate linker, a guanidine linker, an amidine linker, a sulfoxide linker, and a sulfone linker. In some embodiments, the 5-position modified cytidine is selected from NapdC, 2NapdC, TyrdC, and PPdC. In some embodiments, the 5-position modified uridine is selected from NapdU, 2NapdU, PPdU, MOEdU, TyrdU, TrpdU, and ThrdU. In some embodiments, the at least one first 5-position modified pyrimidine is a NapdC and the at least one second 5-position modified pyrimidine is selected from NapdU, 2NapdU, PPdU, MOEdU, TyrdU, and ThrdU. In some embodiments, the at least one first 5-position modified pyrimidine is a PPdC and the at least one second 5-position modified pyrimidine is selected from NapdU, 2NapdU, PPdU, MOEdU, TyrdU, TrpdU, and ThrdU. In some embodiments, the at least one second 5-position modified pyrimidine is a TyrdU. In some embodiments, the first 5-position modified pyrimidine and the second 5-position modified pyrimidine are capable of being incorporated by a polymerase enzyme. In some embodiments, the first 5-position modified pyrimidine and the second 5-position modified pyrimidine are capable of being incorporated by a KOD DNA polymerase.

In some embodiments, the third 5-position modified pyrimidine is selected from a 5-position modified cytidine and a 5-position modified pyrimidine. In some embodiments, the third 5-position modified pyrimidine and the fourth 5-position modified pyrimidine are different 5-position modified pyrimidines. In some embodiments, third 5-position modified pyrimidine is a 5-position modified cytidine and the fourth 5-position modified pyrimidine is a 5-position modified uridine. In some embodiments, the third 5-position modified cytidine is selected from BndC, PEdC, PPdC, NapdC, 2NapdC, NEdC, 2NEdC, and TyrdC. In some embodiments, the 5-position modified uridine is selected from BNdU, NapdU, PedU, IbdU, FbndU, 2NapdU, NedU, MbndU, BfdU, BtdU, PpdU, MOEdU, TyrdU, TrpdU, and ThrdU.

In some embodiments, the target molecule is selected from a protein, a peptide, a carbohydrate, a small molecule, a cell and a tissue. In some embodiments, the first aptamer, second aptamer and the target are capable of forming a trimer complex.

In some embodiments, a method for identifying one or more aptamers capable of binding to a target molecule is provided, comprising:

(a) contacting a library of aptamers with the target molecule to form a mixture, and allowing for the formation of an aptamer-target complex, wherein the aptamer-target complex forms when an aptamer has affinity for the target molecule;

(b) partitioning the aptamer-target complex from the remainder of the mixture (or enriching for the aptamer-target complex);

(c) dissociating the aptamer-target complex; and (d) identifying the one or more aptamers capable of binding to the target molecule;

wherein the library of aptamers comprises a plurality of polynucleotides, wherein each polynucleotide comprises at least one first 5-position modified pyrimidine and at least one second 5-position modified pyrimidine, wherein the first 5-position modified pyrimidine and the second 5-position modified pyrimidine are different 5-position modified pyrimidines. In some embodiments, steps (a), (b) and/or (c) are repeated at least one time, two times, three times, four times, five times, six times, seven times, eight times, nine times or ten times.

In some embodiments, the one or more aptamers capable of binding to the target molecule are amplified. In some embodiments, the mixture comprises a polyanionic competitor molecule. In some embodiments, the polyanionic competitor is selected from an oligonucleotide, polydextran, DNA, heparin and dNTPs. In some embodiments, polydextran is dextran sulfate; and DNA is herring sperm DNA or salmon sperm DNA.

In some embodiments, the target molecule is selected from a protein, a peptide, a carbohydrate, a small molecule, a cell and a tissue.

In some embodiments, each polynucleotide comprises a fixed region at the 5' end of the polynucleotide. In some embodiments, the fixed region at the 5' end of each polynucleotide is at least 10, at least 15, at least 20, at least 25 or at least 30 nucleotides in length, or 5 to 30, 10 to 30, 15 to 30, 5 to 20, or 10 to 20 nucleotides in length. In some embodiments, each polynucleotide comprises a fixed region at the 3' end of the polynucleotide. In some embodiments, the fixed region at the 3' end of the polynucleotide is at least 10, at least 15, at least 20, at least 25 or at least 30 nucleotides in length, or 5 to 30, 10 to 30, 15 to 30, 5 to 20, or 10 to 20 nucleotides in length.

In some embodiments, the first 5-position modified pyrimidine is a 5-position modified uridine and wherein the second 5-position modified pyrimidine is a 5-position modified cytidine. In some embodiments, the first 5-position modified pyrimidine is a 5-position modified cytidine and wherein the second 5-position modified pyrimidine is a 5-position modified uridine. In some embodiments, the 5-position modified uridine comprises a moiety at the 5-position selected from a naphthyl moiety, a benzyl moiety, a tyrosyl moiety, an indole moiety and a morpholino moiety. In some embodiments, the 5-position modified cytidine comprises a moiety at the 5-position selected from a naphthyl moiety, a benzyl moiety, a tyrosyl moiety and a morpholino moiety. In certain embodiments, the moiety is covalently linked to the 5-position of the base via a linker comprising a group selected from an amide linker, a carbonyl linker, a propynyl linker, an alkyne linker, an ester linker, a urea linker, a carbamate linker, a guanidine linker, an amidine linker, a sulfoxide linker, and a sulfone linker. In some embodiments, the 5-position modified cytidine is selected from NapdC, 2NapdC, TyrdC, and PPdC. In some embodiments, the 5-position modified uridine is selected from NapdU, PPdU, MOEdU, TyrdU, TrpdU, and ThrdU. In some embodiments, the at least one first 5-position modified pyrimidine is a NapdC and the at least one second 5-position modified pyrimidine is selected from NapdU, 2NapdU, PPdU, MOEdU, TrydU, TrpdU, and ThrdU. In some embodiments, the at least one first 5-position modified pyrimidine is a PPdC and the at least one second 5-position modified pyrimidine is selected from NapdU, 2NapdU, PPdU, MOEdU, TyrdU, TrpdU, and ThrdU. In some embodiments, the at least one second 5-position modified pyrimidine is a TyrdU. In some embodiments, the first 5-position modified pyrimidine and the second 5-position modified pyrimidine are capable of being incorporated by a polymerase enzyme. In some embodiments, the first 5-position modified pyrimidine and the second 5-position modified pyrimidine are capable of being incorporated by a KOD DNA polymerase.

In some embodiments, each polynucleotide comprises a random region. In some embodiments, the random region is 20 to 100, or 20 to 90, or 20 to 80, or 20 to 70, or 20 to 60, or 20 to 50, or 20 to 40, or 30 to 100, or 30 to 90, or 30 to 70, or 30 to 60, or 30 to 50, or 30 to 40 nucleotides in length. In some embodiments, each polynucleotide is 20 to 100, or 20 to 90, or 20 to 80, or 20 to 70, or 20 to 60, or 20 to 50, or 30 to 100, or 30 to 90, or 30 to 80, or 30 to 70, or 30 to 60, or 30 to 50, or 40 to 100, or 40 to 90, or 40 to 80, or 40 to 70, or 40 to 60, or 40 to 50 nucleotides in length.

In some embodiments, each polynucleotide is an aptamer that binds a target, and wherein the library comprises at least 1000 aptamers, wherein each aptamer comprises a different nucleotide sequence.

In some embodiments, an aptamer that binds PCSK9 protein is provided. In some such embodiments, the aptamer comprises the sequence 5'-yGpppG-3', wherein each y is a TyrdU and each p is a NapdC. In some embodiments, the aptamer further comprises the sequence 5'-yEAyGA$_n$pAp-3', wherein E is selected from y, A, and G; and n is 0 or 1. In some embodiments, n is 0. In some embodiments, the sequence 5'-yEAyGA$_n$pAp-3' is located 5' of the sequence 5'-yGpppG-3'. In some embodiments, E is y.

In some embodiments, an aptamer that binds PCSK9 is provided, wherein the aptamer comprises the sequence 5'-F$_n$pppAAGRJrpRppW$_m$-3' (SEQ ID NO: 81), wherein F is selected from r and G; each R is independently selected from G and A; J is selected from r and A; W is selected from r, G, and A; n is 0 or 1; m is 0 or 1; r is PpdC; and p is NapdU. In some embodiments, m is 1. In some embodiments, F is r. In some embodiments, J is r. In some embodiments, W is G.

In some embodiments, an aptamer that binds PCSK9 is provided, wherein the aptamer comprises the sequence 5'-TTppGGpp-3', wherein each p is a NapdC.

In some embodiments, an aptamer that binds PCSK9 is 20 to 100, or 20 to 90, or 20 to 80, or 20 to 70, or 20 to 60, or 20 to 50, or 30 to 100, or 30 to 90, or 30 to 80, or 30 to 70, or 30 to 60, or 30 to 50, or 40 to 100, or 40 to 90, or 40 to 80, or 40 to 70, or 40 to 60, or 40 to 50 nucleotides in length.

In some embodiments, the aptamer inhibits PCSK9 binding to LDL-R. In some embodiments, the aptamer inhibits PCSK9 binding to LDL-R with an IC$_{50}$ of less than 30 nM, less than 20 nM, or less than 15 nM.

In some embodiments, a method of lowering cholesterol in a subject is provided, comprising administering to a subject in need thereof an aptamer that binds PCSK9. In some embodiments, the aptamer that binds PCSK9 is an aptamer provided herein. In some embodiments, the cholesterol is low-density lipoprotein (LDL) cholesterol (LDL-C). In some embodiments, the subject has heterozygous familial hypercholesterolemia or clinical atherosclerotic cardiovascular disease (CVD).

The foregoing and other objects, features, and advantages of the invention will become more apparent from the following detailed description, which proceeds with reference to the accompanying figures.

DETAILED DESCRIPTION

Figure 1:
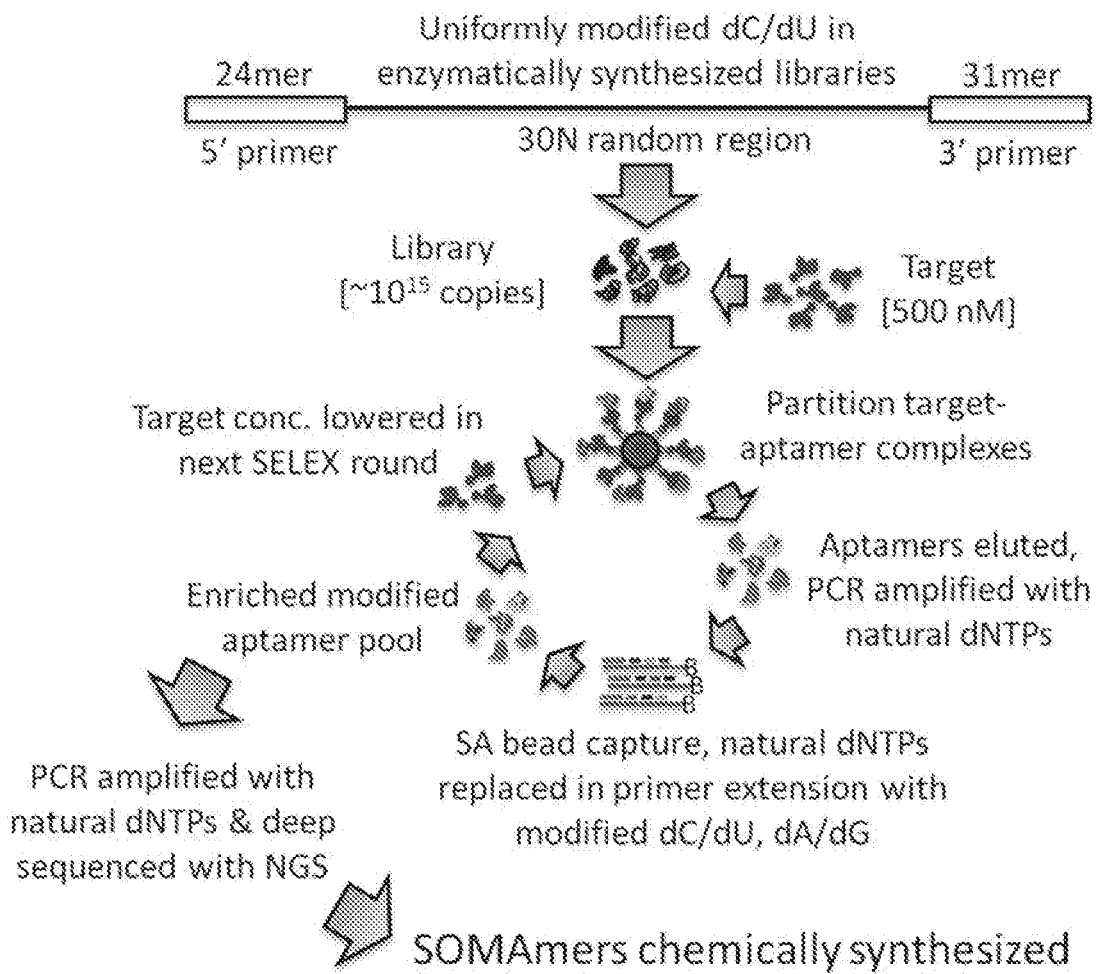
FIG. 1. Selection of nucleic acid aptamers modified with DNA libraries containing C5-position modified uridine and cytidine triphosphates. Schematics of selection with two modified bases. Outline of selection method in which 30N randomized chemically synthesized master antisense biotinylated template library was used to enzymatically synthesize various modified and unmodified libraries by primer extension reactions.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Further, ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean ±20% of the indicated range, value, or structure, unless otherwise indicated. As used herein, the terms "include" and "comprise" are open ended and are used synonymously.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs). As used herein, the term "cytidine" is used generically to refer to a ribonucleotide, deoxyribonucleotide, or modified ribonucleotide comprising a cytosine base, unless specifically indicated otherwise. The term "cytidine" includes 2'-modified cytidines, such as 2'-fluoro, 2'-methoxy, etc. Similarly, the term "modified cytidine" or a specific modified cytidine also refers to a ribonucleotide, deoxyribonucleotide, or modified ribonucleotide (such as 2'-fluoro, 2'-methoxy, etc.) comprising the modified cytosine base, unless specifically indicated otherwise. The term "uridine" is used generically to refer to a ribonucleotide, deoxyribonucleotide, or modified ribonucleotide comprising a uracil base, unless specifically indicated otherwise. The term "uridine" includes 2'-modified uridines, such as 2'-fluoro, 2'-methoxy, etc. Similarly, the term "modified uridine" or a specific modified uridine also refers to a ribonucleotide, deoxyribonucleotide, or modified ribonucleotide (such as 2'-fluoro, 2'-methoxy, etc.) comprising the modified uracil base, unless specifically indicated otherwise.

Figure 20:
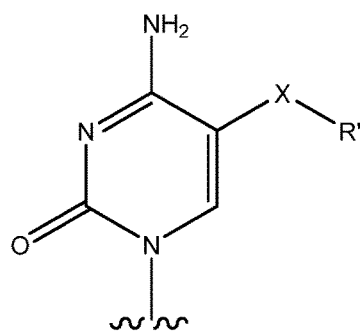
FIG. 20. Certain exemplary 5-position modified uridines and cytidines that may be incorporated into aptamers.
Figure 20:
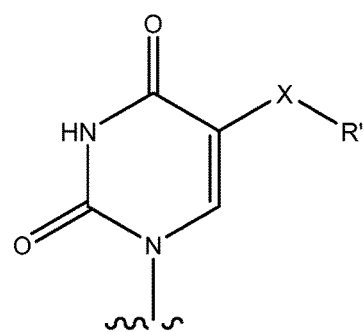
Figure 20:
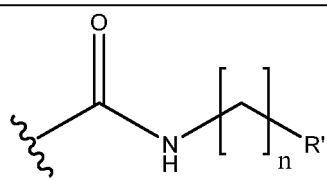
Figure 20:
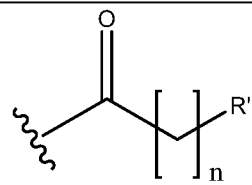
Figure 20:
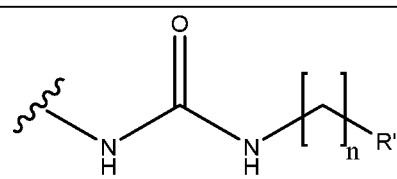
Figure 20:
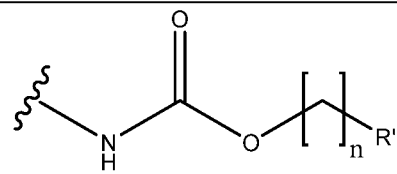
Figure 20:
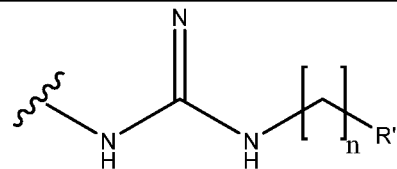
Figure 20:
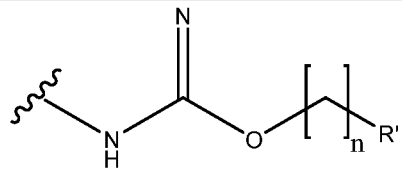
Figure 20:
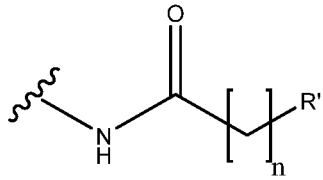
Figure 20:
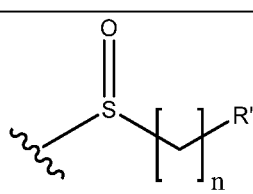
Figure 20:
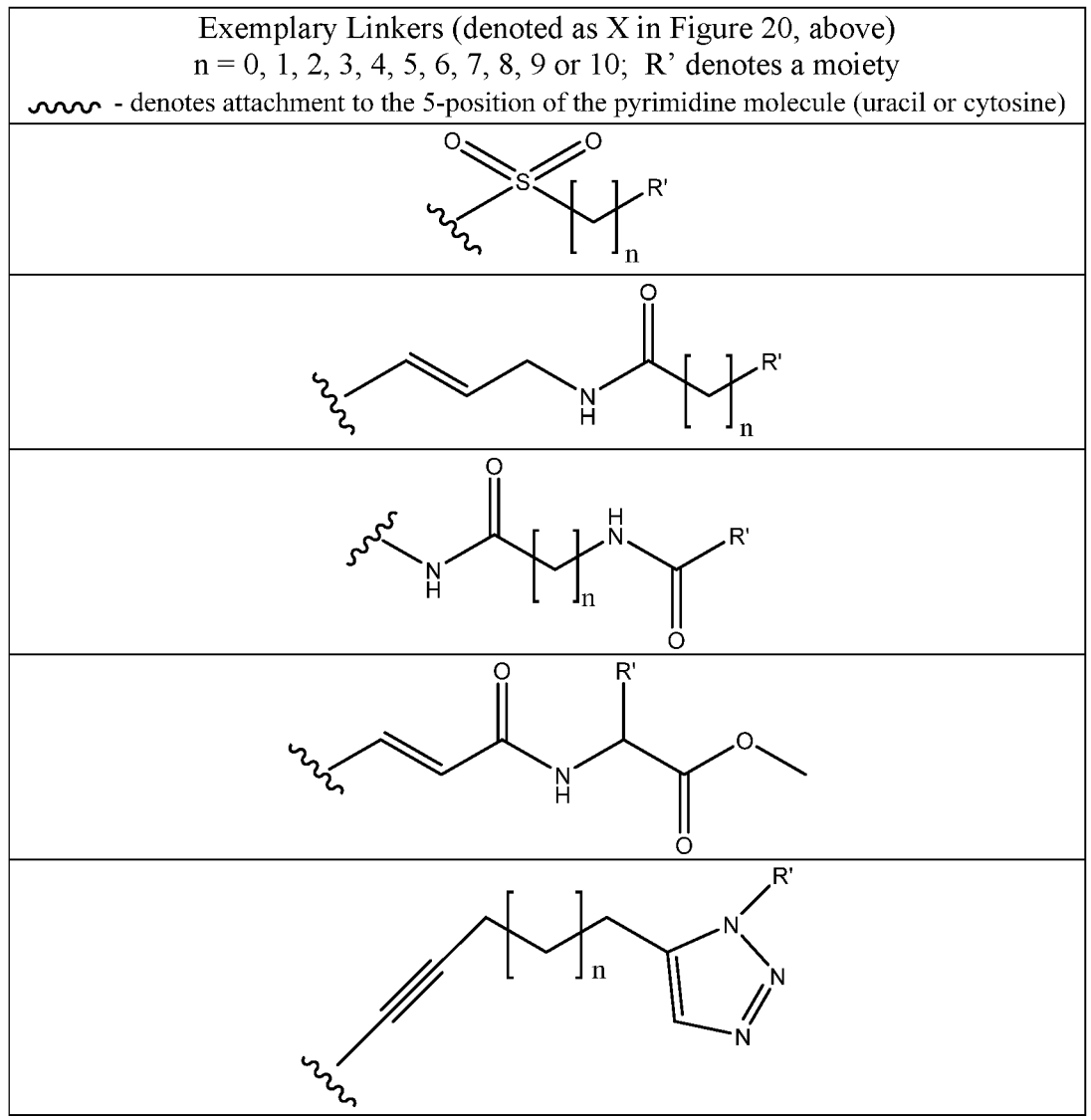
Figure 20:
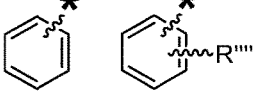
Figure 20:
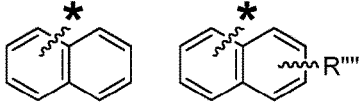
Figure 20:
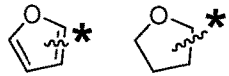
Figure 20:
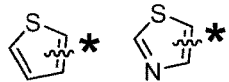
Figure 20:
Figure 20:
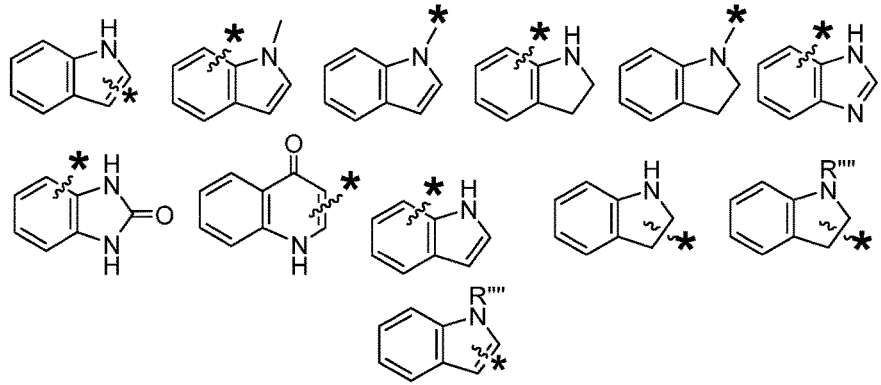
Figure 20:
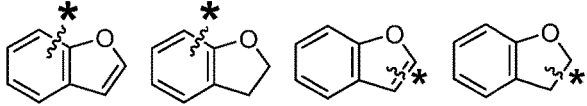
Figure 20:
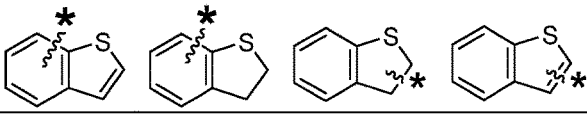
Figure 20:
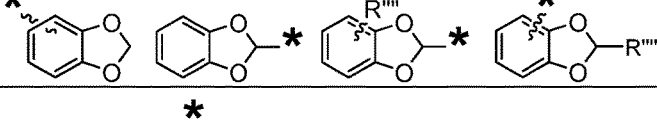
Figure 20:
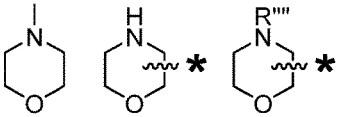

As used herein, the term "5-position modified cytidine" or "C-5 modified cytidine" refers to a cytidine with a modification at the C-5 position of the cytidine, e.g., as shown in FIG. 20. Nonlimiting exemplary 5-position modified cytidines include those shown in FIG. 22. Nonlimiting exemplary 5-position modified cytidines include, but are not limited to, 5-(N-benzylcarboxamide)-2'-deoxycytidine (referred to as "BndC" and shown in FIG. 21); 5-(N-2-phenylethylcarboxamide)-2'-deoxycytidine (referred to as "PEdC" and shown in FIG. 21); 5-(N-3-phenylpropylcarboxamide)-2'-deoxycytidine (referred to as "PPdC" and shown in FIG. 21); 5-(N-1-naphthylmethylcarboxamide)-2'-deoxycytidine (referred to as "NapdC" and shown in FIG. 21); 5-(N-2-naphthylmethylcarboxamide)-2'-deoxycytidine (referred to as "2NapdC" and shown in FIG. 21); 5-(N-1-naphthyl-2-ethylcarboxamide)-2'-deoxycytidine (referred to as "NEdC" and shown in FIG. 21); 5-(N-2-naphthyl-2-ethylcarboxamide)-2'-deoxycytidine (referred to as "2NEdC" and shown in FIG. 21); and 5-(N-tyrosylcarboxamide)-2'-deoxycytidine (referred to as TyrdC and shown in FIG. 21). In some embodiments, the C5-modified cytidines, e.g., in their triphosphate form, are capable of being incorporated into an oligonucleotide by a polymerase (e.g., KOD DNA polymerase).

Chemical modifications of the C-5 modified cytidines described herein can also be combined with, singly or in any combination, 2'-position sugar modifications (for example, 2'-O-methyl or 2'-fluoro), modifications at exocyclic amines, and substitution of 4-thiocytidine and the like.

As used herein, the term "C-5 modified uridine" or "5-position modified uridine" refers to a uridine (typically a deoxyuridine) with a modification at the C-5 position of the uridine, e.g., as shown in FIG. 20. In some embodiments, the C5-modified uridines, e.g., in their triphosphate form, are capable of being incorporated into an oligonucleotide by a polymerase (e.g., KOD DNA polymerase). Nonlimiting exemplary 5-position modified uridines include those shown in FIG. 21. Nonlimiting exemplary 5-position modified uridines include:

5-(N-benzylcarboxamide)-2'-deoxyuridine (BndU),
5-(N-phenethylcarboxamide)-2'-deoxyuridine (PEdU),
5-(N-thiophenylmethylcarboxamide)-2'-deoxyuridine (ThdU),
5-(N-isobutylcarboxamide)-2'-deoxyuridine (iBudU),
5-(N-tyrosylcarboxamide)-2'-deoxyuridine (TyrdU),
5-(N-3,4-methylenedioxybenzylcarboxamide)-2'-deoxyuridine (MBndU),
5-(N-4-fluorobenzylcarboxamide)-2'-deoxyuridine (FBndU),
5-(N-3-phenylpropylcarboxamide)-2'-deoxyuridine (PPdU),
5-(N-imidizolylethylcarboxamide)-2'-deoxyuridine (ImdU),
5-(N-tryptaminocarboxamide)-2'-deoxyuridine (TrpdU),
5-(N-R-threoninylcarboxamide)-2'-deoxyuridine (ThrdU),
5-(N-[1-(3-trimethylamonium) propyl]carboxamide)-2'-deoxyuridine chloride,
5-(N-naphthylmethylcarboxamide)-2'-deoxyuridine (NapdU),
5-(N-[1-(2,3-dihydroxypropyl)]carboxamide)-2'-deoxyuridine),
5-(N-2-naphthylmethylcarboxamide)-2'-deoxyuridine (2NapdU),
5-(N-1-naphthylethylcarboxamide)-2'-deoxyuridine (NEdU),
5-(N-2-naphthylethylcarboxamide)-2'-deoxyuridine (2NEdU),
5-(N-3-benzofuranylethylcarboxamide)-2'-deoxyuridine (BFdU),
5-(N-3-benzothiophenylethylcarboxamide)-2'-deoxyuridine (BTdU).

Chemical modifications of the C-5 modified uridines described herein can also be combined with, singly or in any combination, 2'-position sugar modifications (for example, 2'-O-methyl or 2'-fluoro), modifications at exocyclic amines, and substitution of 4-thiouridine and the like.

As used herein, the terms "modify," "modified," "modification," and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. Additional modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers.

As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers but the terms nucleic acid, oligonucleotide, and polynucleotide are not limited to aptamers.

Polynucleotides can also contain analogous forms of ribose or deoxyribose sugars that are generally known in the art, including 2'-O-methyl, 2'-O-allyl, 2'-O-ethyl, 2'-O-propyl, 2'-O—CH$_2$CH$_2$OCH3, 2'-fluoro, 2'-NH$_2$ or 2'-azido, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted herein, one or more phosphodiester linkages may be replaced by alternative linking groups. These alternative linking groups include embodiments wherein phosphate is replaced by P(O)S ("thioate"), P(S)S ("dithioate"), (O)NR$^X_2$ ("amidate"), P(O) R$^X$, P(O)OR$^{X_1}$, CO or CH$_2$ ("formacetal"), in which each $R^X$ or $R^{Xt}$ are independently H or substituted or unsubstituted alkyl (C1-C20) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

Polynucleotides can also contain analogous forms of carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

If present, a modification to the nucleotide structure can be imparted before or after assembly of a polymer. A sequence of nucleotides can be interrupted by non-nucleotide components. A polynucleotide can be further modified after polymerization, such as by conjugation with a labeling component.

As used herein, the term "at least one nucleotide" when referring to modifications of a nucleic acid, refers to one, several, or all nucleotides in the nucleic acid, indicating that any or all occurrences of any or all of A, C, T, G or U in a nucleic acid may be modified or not.

As used herein, "nucleic acid ligand," "aptamer," "SOMAmer," and "clone" are used interchangeably to refer to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In one embodiment, the action is specific binding affinity for a target molecule, such target molecule being a three dimensional chemical structure other than a polynucleotide that binds to the aptamer through a mechanism which is independent of Watson/Crick base pairing or triple helix formation, wherein the aptamer is not a nucleic acid having the known physiological function of being bound by the target molecule. Aptamers to a given target include nucleic acids that are identified from a candidate mixture of nucleic acids, where the aptamer is a ligand of the target, by a method comprising: (a) contacting the candidate mixture with the target, wherein nucleic acids having an increased affinity to the target relative to other nucleic acids in the candidate mixture can be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby aptamers of the target molecule are identified. It is recognized that affinity interactions are a matter of degree; however, in this context, the "specific binding affinity" of an aptamer for its target means that the aptamer binds to its target generally with a much higher degree of affinity than it binds to other, non-target, components in a mixture or sample. An "aptamer," "SOMAmer," or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers can have either the same or different numbers of nucleotides. Aptamers may be DNA or RNA and may be single stranded, double stranded, or contain double stranded or triple stranded regions. In some embodiments, the aptamers are prepared using a SELEX process as described herein, or known in the art.

As used herein, a "SOMAmer" or Slow Off-Rate Modified Aptamer refers to an aptamer having improved off-rate characteristics. SOMAmers can be generated using the improved SELEX methods described in U.S. Pat. No. 7,947,447, entitled "Method for Generating Aptamers with Improved Off-Rates."

As used herein, an aptamer comprising two different types of 5-position modified pyrimidines or C-5 modified pyrimidines may be referred to as "dual modified aptamers", aptamers having "two modified bases", aptamers having "two base modifications" or "two bases modified", aptamer having "double modified bases", all of which may be used interchangeably. A library of aptamers or aptamer library may also use the same terminology. Thus, in some embodiments, an aptamer comprises two different 5-position modified pyrimidines wherein the two different 5-position modified pyrimidines are selected from a NapdC and a NapdU, a NapdC and a PPdU, a NapdC and a MOEdU, a NapdC and a TyrdU, a NapdC and a ThrdU, a PPdC and a PPdU, a PPdC and a NapdU, a PPdC and a MOEdU, a PPdC and a TyrdU, a PPdC and a ThrdU, a NapdC and a 2NapdU, a NapdC and a TrpdU, a 2NapdC and a NapdU, and 2NapdC and a 2NapdU, a 2NapdC and a PPdU, a 2NapdC and a TrpdU, a 2NapdC and a TyrdU, a PPdC and a 2NapdU, a PPdC and a TrpdU, a PPdC and a TyrdU, a TyrdC and a TyrdU, a TrydC and a 2NapdU, a TyrdC and a PPdU, a TyrdC and a TrpdU, a TyrdC and a TyrdU, and a TyrdC and a TyrdU. In some embodiments, an aptamer comprises at least one modified uridine and/or thymidine and at least one modified cytidine, wherein the at least one modified uridine and/or thymidine is modified at the 5-position with a moiety selected from a naphthyl moiety, a benzyl moiety, a fluorobenzyl moiety, a tyrosyl moiety, an indole moiety a morpholino moiety , an isobutyl moiety, a 3,4-methylenedioxy benzyl moiety, a benzothiophenyl moiety, and a benzofuranyl moiety, and wherein the at least one modified cytidine is modified at the 5-position with a moiety selected from a naphthyl moiety, a tyrosyl moiety, and a benzyl moiety. In certain embodiments, the moiety is covalently linked to the 5-position of the base via a linker comprising a group selected from an amide linker, a carbonyl linker, a propynyl linker, an alkyne linker, an ester linker, a urea linker, a carbamate linker, a guanidine linker, an amidine linker, a sulfoxide linker, and a sulfone linker.

As used herein, an aptamer comprising a single type of 5-position modified pyrimidine or C-5 modified pyrimidine may be referred to as "single modified aptamers", aptamers having a "single modified base", aptamers having a "single base modification" or "single bases modified", all of which may be used interchangeably. A library of aptamers or aptamer library may also use the same terminology. As used herein, "protein" is used synonymously with "peptide," "polypeptide," or "peptide fragment." A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

In certain embodiments, an aptamer comprises a first 5-position modified pyrimidine and a second 5-position modified pyrimidine, wherein the first 5-position modified pyrimidine comprises a tryosyl moiety at the 5-position of the first 5-position modified pyrimidine, and the second 5-position modified pyrimidine comprises a naphthyl moiety or benzyl moiety at the 5-position at the second 5-position modified pyrimidine. In a related embodiment the first 5-position modified pyrimidine is a uracil. In a related embodiment, the second 5-position modified pyrimidine is a cytosine. In a related embodiment, at least 10%, 15%, 20%, 25%, 30%, 35%, 40%, 45%, 50%, 55%, 60%, 65%, 70%, 75%, 80%, 85%, 90%, 95%, or 100% of the uracils of the aptamer are modified at the 5-position. In a related embodiment, at least 10%, 15%, 20%, 25%, 30%, 35%, 40%, 45%, 50%, 55%, 60%, 65%, 70%, 75%, 80%, 85%, 90%, 95%, or 100% of the cytosine of the aptamer are modified at the 5-position.

Modified Nucleotides

Figure 21:
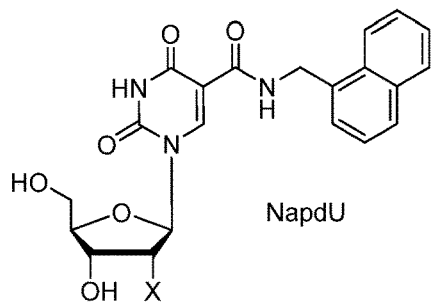
FIG. 21. Certain exemplary modifications that may be present at the 5-position of uridine. The chemical structure of the C-5 modification includes the exemplary amide linkage that links the modification to the 5-position of the uridine. The 5-position moieties shown include a benzyl moiety (e.g., Bn, PE and a PP), a naphthyl moiety (e.g., Nap, 2Nap, NE), a butyl moiety (e.g, iBu), a fluorobenzyl moiety (e.g., FBn), a tyrosyl moiety (e.g., a Tyr), a 3,4-methylenedioxy benzyl (e.g., MBn), a morpholino moiety (e.g., MOE), a benzofuranyl moiety (e.g., BF), an indole moiety (e.g, Trp) and a hydroxypropyl moiety (e.g., Thr).
Figure 21:
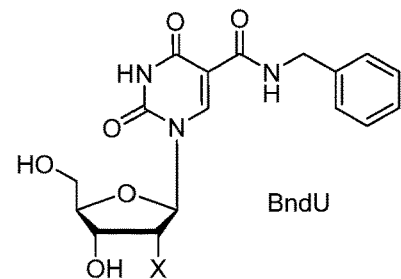
Figure 21:
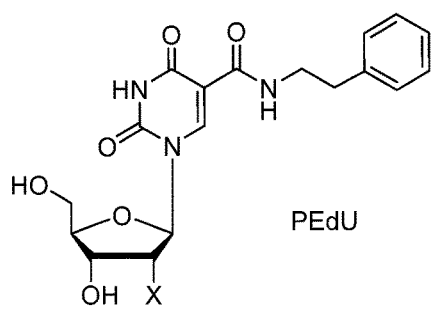
Figure 21:
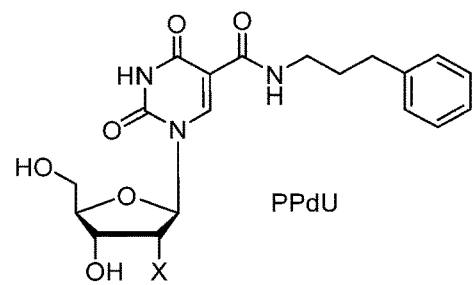
Figure 21:
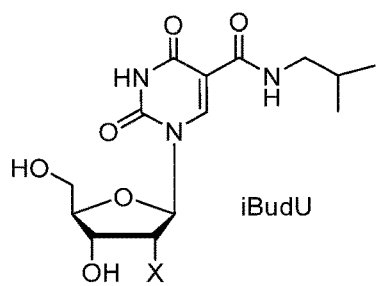
Figure 21:
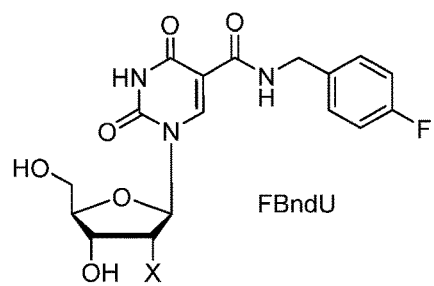
Figure 21:
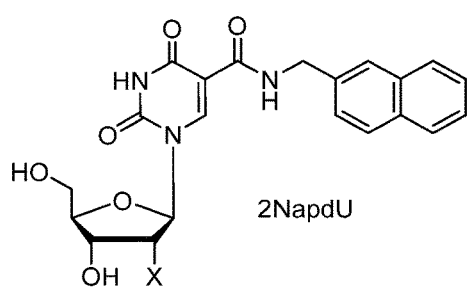
Figure 21:
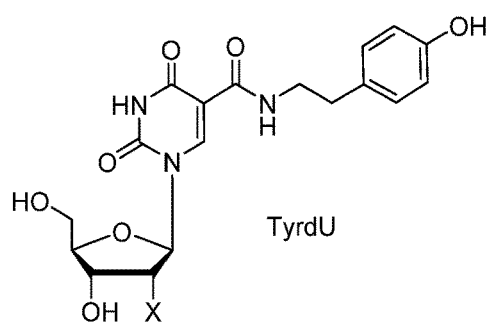
Figure 21:
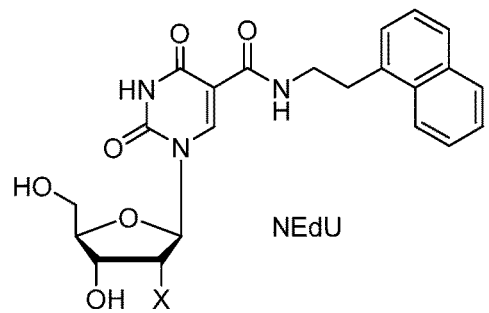
Figure 21:
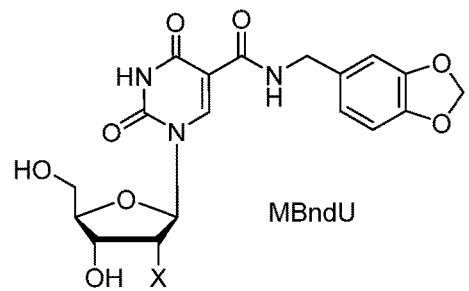
Figure 21:
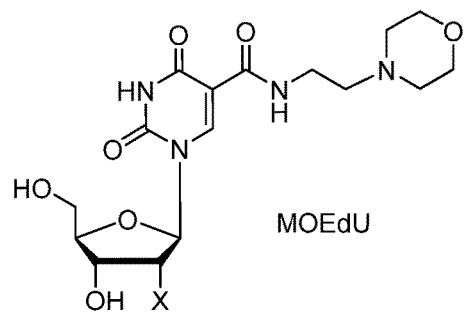
Figure 21:
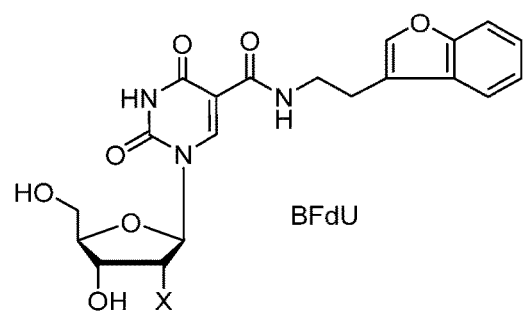
Figure 21:
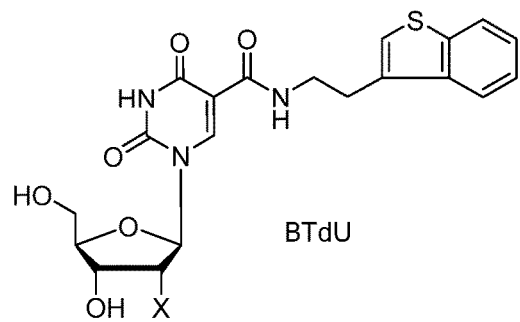
Figure 21:
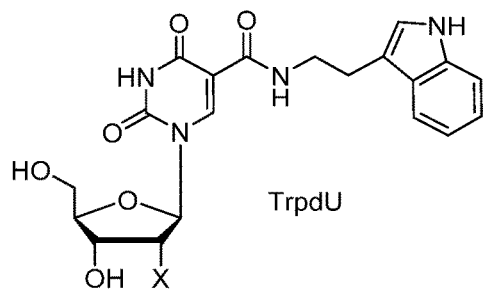
Figure 21:
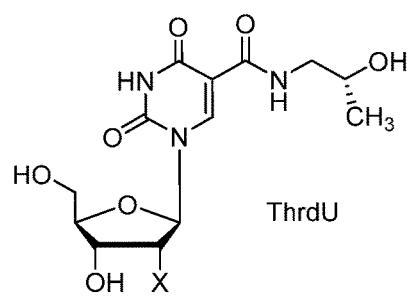
Figure 22:
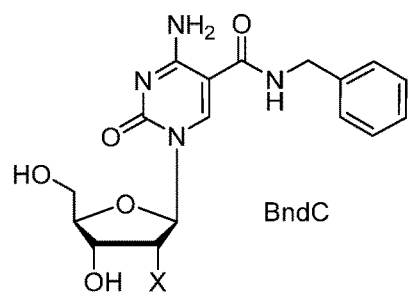
FIG. 22. Certain exemplary modifications that may be present at the 5-position of cytidine. The chemical structure of the C-5 modification includes the exemplary amide linkage that links the modification to the 5-position of the cytidine. The 5-position moieties shown include a benzyl moiety (e.g., Bn, PE and a PP), a naphthyl moiety (e.g., Nap, 2Nap, NE, and 2NE) and a tyrosyl moiety (e.g., a Tyr).
Figure 22:
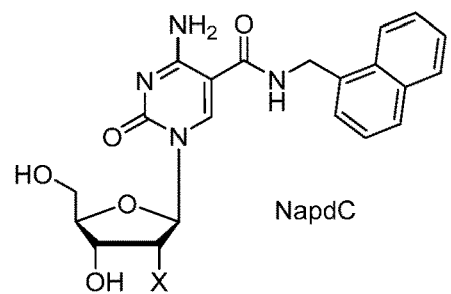
Figure 22:
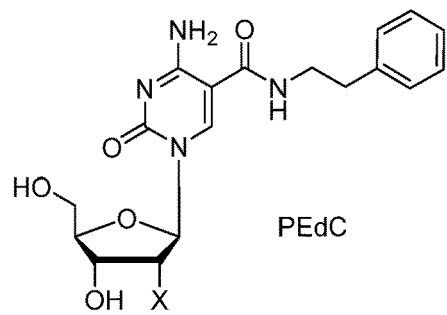
Figure 22:
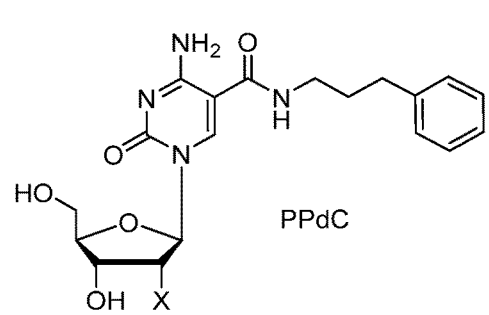
Figure 22:
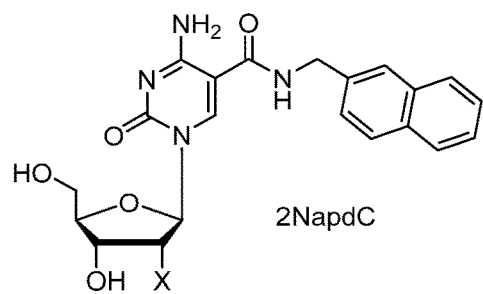
Figure 22:
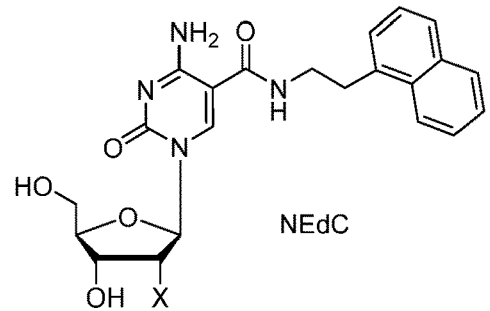
Figure 22:
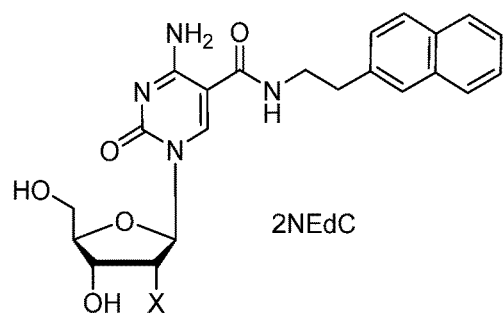
Figure 22:
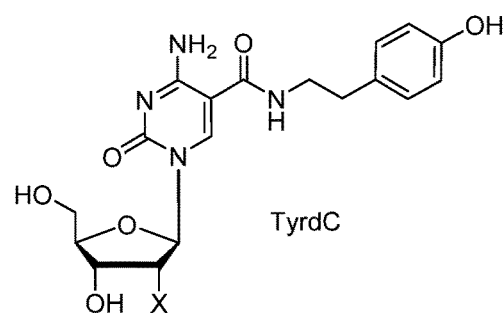

In certain embodiments, the disclosure provides oligonucleotides, such as aptamers, which comprise two different types of base-modified nucleotides. In some embodiments, the oligonucleotides comprise two different types of 5-position modified pyrimidines. In some embodiments, the oligonucleotide comprises at least one C5-modified cytidine and at least one C5-modified uridine. In some embodiments, the oligonucleotide comprises two different C5-modified cytidines. In some embodiments, the oligonucleotide comprises two different C5-modified uridines. Nonlimiting exemplary C5-modified uridines and cytidines are shown, for example, in Formula I below, and in FIG. 20. Certain nonlimiting exemplary C5-modified uridines are shown in FIG. 21, and certain nonlimiting exemplary C5-modified cytidines are shown in FIG. 22.

In some embodiments, the oligonucleotide comprises at least one pyrimidine of Formula I:

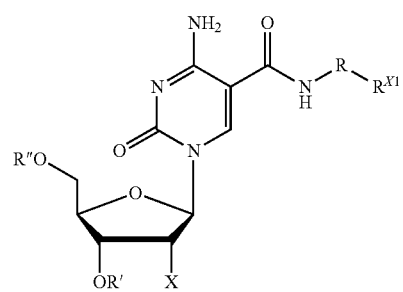

Formula I wherein

R is independently a —(CH$_2$)$_n$—, wherein n is an integer selected from 0, 1, 2, 3, 4, 5, 6, 7, 8, 9 or 10;

R$^{X1}$ is independently selected from the group consisting of

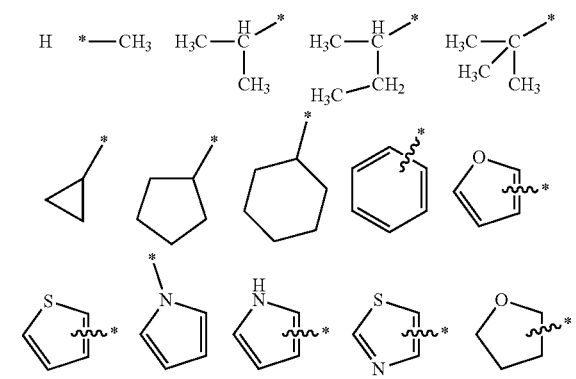

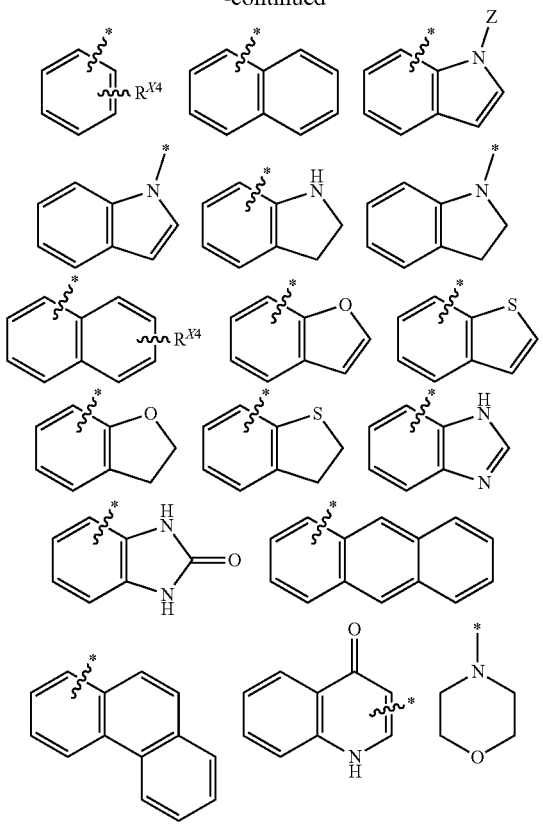

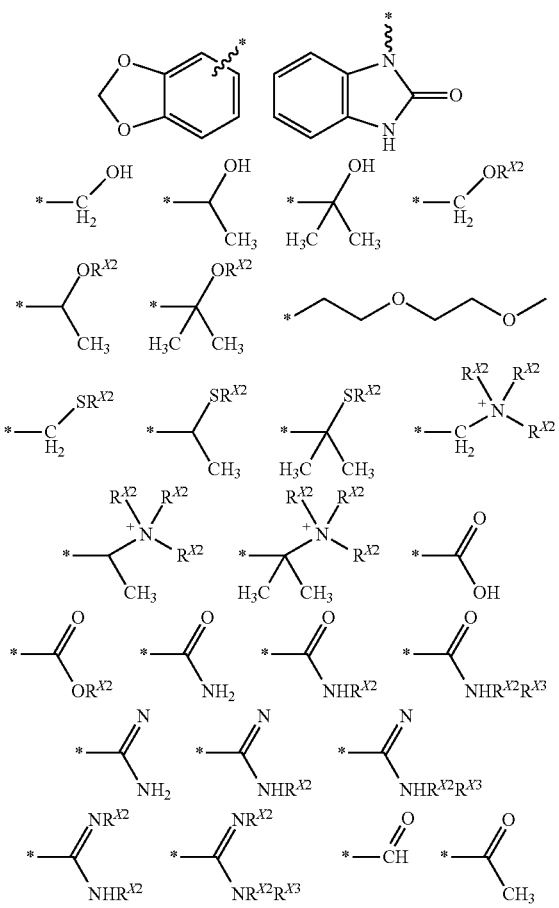

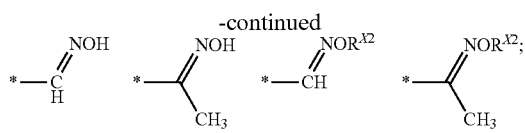
-continued wherein, * denotes the point of attachment of the $R^{X1}$ group to the —$(CH_2)_n$— group; and wherein, $R^{X4}$ is independently selected from the group consisting of a branched or linear lower alkyl (C1-C20); a hydroxyl group; a halogen (F, Cl, Br, I); nitrile (CN); boronic acid ($BO_2H_2$); carboxylic acid (COOH); carboxylic acid ester ($COOR^{X2}$); primary amide ($CONH_2$); secondary amide ($CONHR^{X2}$); tertiary amide ($CONR^{X2}R^{X3}$); sulfonamide ($SO_2NH_2$); N-alkylsulfonamide ($SONHR^{X2}$);

$R^{X2}$ and $R^{X3}$ are independently, for each occurrence, selected from the group consisting of a branched or linear lower alkyl (C1-C20); phenyl ($C_6H_5$); an $R^{X4}$ substituted phenyl ring ($R^{X4}C_6H_4$), wherein $R^{X4}$ is defined above; a carboxylic acid (COOH); a carboxylic acid ester ($COOR^{X5}$), wherein $R^{X5}$ is a branched or linear lower alkyl (C1-C20); and cycloalkyl, wherein $R^{X2}$ and $R^{X3}$ together form a substituted or unsubstituted 5 or 6 membered ring;

X is independently selected from the group consisting of —H, —OH, —OMe, —O-allyl, —F, —OEt, —OPr, —$OCH_2CH_2OCH_3$, $NH_2$ and -azido;

R' is independently selected from the group consisting of a —H, —OAc; —OBz; —P ($NiPr_2$)($OCH_2CH_2CN$); and —$OSiMe_2tBu$;

R" is independently selected from the group consisting of a hydrogen, 4,4'-dimethoxytrityl (DMT) and triphosphate (—P(O)(OH)—O—P(O)(OH)—O—P(O)(OH)$_2$) or a salt thereof;

Z is independently selected from the group consisting of a —H, a substituted or unsubstituted C(1-4)alkyl; and salts thereof.

In some embodiments, the oligonucleotide comprises at least one modified pyrimidine shown in FIG. 21, wherein each X is independently selected from —H, —OH, —OMe, —O-allyl, —F, —OEt, —OPr, —$OCH_2CH_2OCH_3$, $NH_2$ and -azido.

In some embodiments, the oligonucleotide comprises at least one modified pyrimidine shown in FIG. 22, wherein each X is independently selected from —H, —OH, —OMe, —O-allyl, —F, —OEt, —OPr, —$OCH_2CH_2OCH_3$, $NH_2$ and -azido.

In some embodiments, the oligonucleotide comprises at least one modified pyrimidine shown in FIG. 21 and at least one modified pyrimidine shown in FIG. 22, wherein each X is independently selected from —H, —OH, —OMe, —O-allyl, —F, —OEt, —OPr, —$OCH_2CH_2OCH_3$, $NH_2$ and -azido. Certain nonlimiting exemplary pairs of modified pyrimidines are shown in the Examples described herein.

In some embodiments, the oligonucleotide comprises at least one modified pyrimidine shown in FIG. 20, wherein the 2' position of the ribose is independently selected from —H, —OH, —OMe, —O-allyl, —F, —OEt, —OPr, —$OCH_2CH_2OCH_3$, $NH_2$ and -azido. In some embodiments, the oligonucleotide comprises at least two modified pyrimidines shown in FIG. 20, wherein the 2' position of the ribose is independently selected from —H, —OH, —OMe, —O-allyl, —F, —OEt, —OPr, —$OCH_2CH_2OCH_3$, $NH_2$ and -azido.

In some embodiments, the oligonucleotide comprises at least one modified pyrimidine shown in FIG. 20 and at least one modified pyrimidine shown in FIG. 21 or FIG. 22, wherein the 2' position of the ribose is independently selected from —H, —OH, —OMe, —O-allyl, —F, —OEt, —OPr, —$OCH_2CH_2OCH_3$, $NH_2$ and -azido. Certain nonlimiting exemplary pairs of modified pyrimidines are shown in the Examples described herein.

In any of the embodiments described herein, the oligonucleotide may be an aptamer. In some such embodiments, the oligonucleotide is an aptamer that specifically binds a target polypeptide.

Preparation of Oligonucleotides

The automated synthesis of oligodeoxynucleosides is routine practice in many laboratories (see e.g., Matteucci, M. D. and Caruthers, M. H., (1990) J. Am. Chem. Soc., 103: 3185-3191, the contents of which are hereby incorporated by reference in their entirety). Synthesis of oligoribonucleosides is also well known (see e.g. Scaringe, S. A., et al., (1990) Nucleic Acids Res. 18:5433-5441, the contents of which are hereby incorporated by reference in their entirety). As noted herein, the phosphoramidites are useful for incorporation of the modified nucleoside into an oligonucleotide by chemical synthesis, and the triphosphates are useful for incorporation of the modified nucleoside into an oligonucleotide by enzymatic synthesis. (See e.g., Vaught, J. D. et al. (2004) J. Am. Chem. Soc., 126:11231-11237; Vaught, J. V., et al. (2010) J Am. Chem. Soc. 132, 4141-4151; Gait, M. J. "Oligonucleotide Synthesis a practical approach" (1984) IRL Press (Oxford, UK); Herdewijn, P. "Oligonucleotide Synthesis" (2005) (Humana Press, Totowa, N.J. (each of which is incorporated herein by reference in its entirety).

The SELEX Method

The terms "SELEX" and "SELEX process" are used interchangeably herein to refer generally to a combination of (1) the selection of nucleic acids that interact with a target molecule in a desirable manner, for example binding with high affinity to a protein, with (2) the amplification of those selected nucleic acids. The SELEX process can be used to identify aptamers with high affinity to a specific target molecule or biomarker.

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands." The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH$_2$), 2'-fluoro (2'-F), and/or 2'-O-methyl (2'-OMe). See also, U.S. Patent Application Publication No. 20090098549, entitled "SELEX and PHOTOSELEX," which describes nucleic acid libraries having expanded physical and chemical properties and their use in SELEX and photoSELEX.

SELEX can also be used to identify aptamers that have desirable off-rate characteristics. See U.S. Pat. No. 7,947,447, entitled "Method for Generating Aptamers with Improved Off-Rates," which is incorporated herein by reference in its entirety, describes improved SELEX methods for generating aptamers that can bind to target molecules. Methods for producing aptamers and photoaptamers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates dissociate and do not reform, while complexes with slow dissociation rates remain intact. Additionally, the methods include the use of modified nucleotides in the production of candidate nucleic acid mixtures to generate aptamers with improved off-rate performance (see U.S. Pat. No. 8,409,795, entitled "SELEX and PhotoSELEX"). (See also U.S. Pat. No. 7,855,054 and U.S. Patent Publication No. 20070166740). Each of these applications is incorporated herein by reference in its entirety.

"Target" or "target molecule" or "target" refers herein to any compound upon which a nucleic acid can act in a desirable manner. A target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc., without limitation. Virtually any chemical or biological effector may be a suitable target. Molecules of any size can serve as targets. A target can also be modified in certain ways to enhance the likelihood or strength of an interaction between the target and the nucleic acid. A target can also include any minor variation of a particular compound or molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Embodiments of the SELEX process in which the target is a peptide are described in U.S. Pat. No. 6,376,190, entitled "Modified SELEX Processes Without Purified Protein." In some embodiments, a target is a protein.

As used herein, "competitor molecule" and "competitor" are used interchangeably to refer to any molecule that can form a non-specific complex with a non-target molecule. In this context, non-target molecules include free aptamers, where, for example, a competitor can be used to inhibit the aptamer from binding (rebinding), non-specifically, to another non-target molecule. A "competitor molecule" or "competitor" is a set of copies of one type or species of molecule. "Competitor molecules" or "competitors" refer to more than one such set of molecules. Competitor molecules include, but are not limited to oligonucleotides, polyanions (e.g., heparin, herring sperm DNA, salmon sperm DNA, tRNA, dextran sulfate, polydextran, abasic phosphodiester polymers, dNTPs, and pyrophosphate). In various embodiments, a combination of one or more competitor can be used.

As used herein, "non-specific complex" refers to a non-covalent association between two or more molecules other than an aptamer and its target molecule. A non-specific complex represents an interaction between classes of molecules. Non-specific complexes include complexes formed between an aptamer and a non-target molecule, a competitor and a non-target molecule, a competitor and a target molecule, and a target molecule and a non-target molecule.

As used herein, the term "slow off-rate enrichment process" refers to a process of altering the relative concentrations of certain components of a candidate mixture such that the relative concentration of aptamer affinity complexes having slow dissociation rates is increased relative to the concentration of aptamer affinity complexes having faster, less desirable dissociation rates. In one embodiment, the slow off-rate enrichment process is a solution-based slow off-rate enrichment process. In this embodiment, a solution-based slow off-rate enrichment process takes place in solution, such that neither the target nor the nucleic acids forming the aptamer affinity complexes in the mixture are immobilized on a solid support during the slow off-rate enrichment process. In various embodiments, the slow-off rate enrichment process can include one or more steps, including the addition of and incubation with a competitor molecule, dilution of the mixture, or a combination of these (e.g., dilution of the mixture in the presence of a competitor molecule). Because the effect of an slow off-rate enrichment process generally depends upon the differing dissociation rates of different aptamer affinity complexes (i.e., aptamer affinity complexes formed between the target molecule and different nucleic acids in the candidate mixture), the duration of the slow off-rate enrichment process is selected so as to retain a high proportion of aptamer affinity complexes having slow dissociation rates while substantially reducing the number of aptamer affinity complexes having fast dissociation rates. The slow off-rate enrichment process may be used in one or more cycles during the SELEX process. When dilution and the addition of a competitor are used in combination, they may be performed simultaneously or sequentially, in any order. The slow-off rate enrichment process can be used when the total target (protein) concentration in the mixture is low. In one embodiment, when the slow off-rate enrichment process includes dilution, the mixture can be diluted as much as is practical, keeping in mind that the aptamer retained nucleic acids are recovered for subsequent rounds in the SELEX process. In one embodiment, the slow off-rate enrichment process includes the use of a competitor as well as dilution, permitting the mixture to be diluted less than might be necessary without the use of a competitor.

In one embodiment, the slow off-rate enrichment process includes the addition of a competitor, and the competitor is a polyanion (e.g., heparin or dextran sulfate (dextran)). Heparin or dextran have been used in the identification of specific aptamers in prior SELEX selections. In such methods, however, heparin or dextran is present during the equilibration step in which the target and aptamer bind to form complexes. In such methods, as the concentration of heparin or dextran increases, the ratio of high affinity target/aptamer complexes to low affinity target/aptamer complexes increases. However, a high concentration of heparin or dextran can reduce the number of high affinity target/aptamer complexes at equilibrium due to competition for target binding between the nucleic acid and the competitor. By contrast, the presently described methods add the competitor after the target/aptamer complexes have been allowed to form and therefor does not affect the number of complexes formed. Addition of competitor after equilibrium binding has occurred between target and aptamer creates a non-equilibrium state that evolves in time to a new equilibrium with fewer target/aptamer complexes. Trapping target/aptamer complexes before the new equilibrium has been reached enriches the sample for slow off-rateaptamers since fast off-rate complexes will dissociate first.

In another embodiment, a polyanionic competitor (e.g., dextran sulfate or another polyanionic material) is used in the slow off-rate enrichment process to facilitate the identification of an aptamer that is refractory to the presence of the polyanion. In this context, "polyanionic refractory aptamer" is an aptamer that is capable of forming an aptamer/target complex that is less likely to dissociate in the solution that also contains the polyanionic refractory material than an aptamer/target complex that includes a nonpolyanionic refractory aptamer. In this manner, polyanionic refractory aptamers can be used in the performance of analytical methods to detect the presence or amount or concentration of a target in a sample, where the detection method includes the use of the polyanionic material (e.g. dextran sulfate) to which the aptamer is refractory.

Thus, in one embodiment, a method for producing a polyanionic refractory aptamer is provided. In this embodiment, after contacting a candidate mixture of nucleic acids with the target. The target and the nucleic acids in the candidate mixture are allowed to come to equilibrium. A polyanionic competitor is introduced and allowed to incubate in the solution for a period of time sufficient to insure that most of the fast off rate aptamers in the candidate mixture dissociate from the target molecule. Also, aptamers in the candidate mixture that may dissociate in the presence of the polyanionic competitor will be released from the target molecule. The mixture is partitioned to isolate the high affinity, slow off-rate aptamers that have remained in association with the target molecule and to remove any uncomplexed materials from the solution. The aptamer can then be released from the target molecule and isolated. The isolated aptamer can also be amplified and additional rounds of selection applied to increase the overall performance of the selected aptamers. This process may also be used with a minimal incubation time if the selection of slow off-rate aptamers is not needed for a specific application.

Thus, in one embodiment a modified SELEX process is provided for the identification or production of aptamers having slow (long) off rates wherein the target molecule and candidate mixture are contacted and incubated together for a period of time sufficient for equilibrium binding between the target molecule and nucleic acids contained in the candidate mixture to occur. Following equilibrium binding an excess of competitor molecule, e.g., polyanion competitor, is added to the mixture and the mixture is incubated together with the excess of competitor molecule for a predetermined period of time. A significant proportion of aptamers having off rates that are less than this predetermined incubation period will dissociate from the target during the predetermined incubation period. Re-association of these "fast" off rate aptamers with the target is minimized because of the excess of competitor molecule which can non-specifically bind to the target and occupy target binding sites. A significant proportion of aptamers having longer off rates will remain complexed to the target during the predetermined incubation period. At the end of the incubation period, partitioning nucleic acid-target complexes from the remainder of the mixture allows for the separation of a population of slow off-rate aptamers from those having fast off rates. A dissociation step can be used to dissociate the slow off-rate aptamers from their target and allows for isolation, identification, sequencing, synthesis and amplification of slow off-rate aptamers (either of individual aptamers or of a group of slow off-rate aptamers) that have high affinity and specificity for the target molecule. As with conventional SELEX the aptamer sequences identified from one round of the modified SELEX process can be used in the synthesis of a new candidate mixture such that the steps of contacting, equilibrium binding, addition of competitor molecule, incubation with competitor molecule and partitioning of slow off-rateaptamers can be iterated/repeated as many times as desired.

The combination of allowing equilibrium binding of the candidate mixture with the target prior to addition of competitor, followed by the addition of an excess of competitor and incubation with the competitor for a predetermined period of time allows for the selection of a population of aptamers having off rates that are much greater than those previously achieved.

In order to achieve equilibrium binding, the candidate mixture may be incubated with the target for at least about 5 minutes, or at least about 15 minutes, about 30 minutes, about 45 minutes, about 1 hour, about 2 hours, about 3 hours, about 4 hours, about 5 hours or about 6 hours.

The predetermined incubation period of competitor molecule with the mixture of the candidate mixture and target molecule may be selected as desired, taking account of the factors such as the nature of the target and known off rates (if any) of known aptamers for the target. Predetermined incubation periods may be chosen from: at least about 5 minutes, at least about 10 minutes, at least about 20 minutes, at least about 30 minutes, at least 45 about minutes, at least about 1 hour, at least about 2 hours, at least about 3 hours, at least about 4 hours, at least about 5 hours, at least about 6 hours.

In other embodiments a dilution is used as an off rate enhancement process and incubation of the diluted candidate mixture, target molecule/aptamer complex may be undertaken for a predetermined period of time, which may be chosen from: at least about 5 minutes, at least about 10 minutes, at least about 20 minutes, at least about 30 minutes, at least about 45 minutes, at least about 1 hour, at least about 2 hours, at least about 3 hours, at least about 4 hours, at least about 5 hours, at least about 6 hours.

Embodiments of the present disclosure are concerned with the identification, production, synthesis and use of slow off-rate aptamers. These are aptamers which have a rate of dissociation ($t_{1/2}$) from a non-covalent aptamer-target complex that is higher than that of aptamers normally obtained by conventional SELEX. For a mixture containing non-covalent complexes of aptamer and target, the $t_{1/2}$ represents the time taken for half of the aptamers to dissociate from the aptamer-target complexes. The $t_{1/2}$ of slow dissociation rate aptamers according to the present disclosure is chosen from one of: greater than or equal to about 30 minutes; between about 30 minutes and about 240 minutes; between about 30 minutes to about 60 minutes; between about 60 minutes to about 90 minutes, between about 90 minutes to about 120 minutes; between about 120 minutes to about 150 minutes; between about 150 minutes to about 180 minutes; between about 180 minutes to about 210 minutes; between about 210 minutes to about 240 minutes.

A characterizing feature of an aptamer identified by a SELEX procedure is its high affinity for its target. An aptamer will have a dissociation constant ($k_d$) for its target that is chosen from one of: less than about 1 µM, less than about 100 nM, less than about 10 nM, less than about 1 nM, less than about 100 pM, less than about 10 pM, less than about 1 pM.

Libraries of Oligonucleotides

In some embodiments, libraries of oligonucleotides comprising random sequences are provided. Such libraries may be useful, in some embodiments, for performing SELEX. In some embodiments, each oligonucleotide of a library of oligonucleotides comprises a number of randomized positions, such as at least 20, 25, 30, 35, 40, 45, or 50, or 20-100, 20-80, 20-70, 20-60, 20-50, 20-40, or 30-40 randomized positions. In some embodiments, each oligonucleotide of a library of oligonucleotides comprises fixed sequences flanking the randomized positions. Such fixed flanking sequences may be the same or different from one another (i.e., the 5' flanking sequence and the 3' flanking sequence may be the same or different), and may, in some embodiments, be the same for all members of the library (i.e., all members of the library may have the same 5' flanking sequence, and/or all members of the library may have the same 3' flanking sequence).

In some embodiments, the randomized positions may be made up of four or more different nucleotide bases, one or more of which is modified. In some embodiments, all of one type of nucleotide base is modified or unmodified (e.g., all of the cytidines in the randomized region or modified, or all are unmodified). In some embodiments, one type of nucleotide base in the randomized region is present in both modified and unmodified forms. In some such embodiments, the randomized positions are made up of two modified and two unmodified nucleotide bases. In some such embodiments, the randomized positions are made up of adenine, guanine, C5-modified cytidine, and C5-modified uridine. Nonlimiting exemplary C5-modified cytidines and C5-modified uridines are shown in FIGS. 19 to 21. Libraries of oligonucleotides and methods of making them are further described, e.g., in the Examples herein.

Exemplary Aptamers

In some embodiments, aptamers that bind a target molecule are provided. In some embodiments, the target molecule is a target protein. In some embodiments, aptamers that bind PCSK9 are provided. In some embodiments, an aptamer that binds PCSK9 inhibits binding of PCSK9 to LDL-R. In some such embodiments, the aptamer comprises the sequence 5'-yGpppG-3', wherein each y is a TyrdU and each p is a NapdC. In some embodiments, the aptamer further comprises the sequence 5'-yEAyGA$_n$pAp-3', wherein E is selected from y, A, and G; and n is 0 or 1. In some embodiments, n is 0. In some embodiments, the sequence 5'-yEAyGA$_n$pAp-3' is located 5' of the sequence 5'-yGpppG-3'. In some embodiments, E is y.

In some embodiments, an aptamer that binds PCSK9 is provided, wherein the aptamer comprises the sequence 5'-F$_n$pppAAGRJrpRppW$_m$-3' (SEQ ID NO: 81), wherein F is selected from r and G; each R is independently selected from G and A; J is selected from r and A; W is selected from r, G, and A; n is 0 or 1; m is 0 or 1; r is PpdC; and p is NapdU. In some embodiments, m is 1. In some embodiments, F is r. In some embodiments, J is r. In some embodiments, W is G.

In some embodiments, an aptamer that binds PCSK9 is provided, wherein the aptamer comprises the sequence 5'-TTppGGpp-3', wherein each p is a NapdC.

In some embodiments, an aptamer that binds PCSK9 is 20 to 100, or 20 to 90, or 20 to 80, or 20 to 70, or 20 to 60, or 20 to 50, or 30 to 100, or 30 to 90, or 30 to 80, or 30 to 70, or 30 to 60, or 30 to 50, or 40 to 100, or 40 to 90, or 40 to 80, or 40 to 70, or 40 to 60, or 40 to 50 nucleotides in length.

In some embodiments, the aptamer inhibits PCSK9 binding to LDL-R. In some embodiments, the aptamer inhibits PCSK9 binding to LDL-R with an IC$_{50}$ of less than 30 nM, less than 20 nM, or less than 15 nM.

In some embodiments, a method of lowering cholesterol in a subject is provided, comprising administering to a subject in need thereof an aptamer that binds PCSK9. In some embodiments, the aptamer that binds PCSK9 is an aptamer provided herein. In some embodiments, the cholesterol is low-density lipoprotein (LDL) cholesterol (LDL-C). In some embodiments, the subject has heterozygous familial hypercholesterolemia or clinical atherosclerotic cardiovascular disease (CVD).

Salts

It may be convenient or desirable to prepare, purify, and/or handle a corresponding salt of the compound, for example, a pharmaceutically-acceptable salt. Examples of pharmaceutically acceptable salts are discussed in Berge et al. (1977) "Pharmaceutically Acceptable Salts" J. Pharm. Sci. 66:1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^{X+}$, NH$_2$R$^X_2{}^+$, NHR$^X_3{}^+$, NR$^X_4{}^+$). Examples of some suitable substituted ammonium ions are those derived from: ethylamine, diethylamine, dicyclohexylamine, triethylamine, butylamine, ethylenediamine, ethanolamine, diethanolamine, piperizine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Certain Nonlimiting Exemplary Embodiments

Embodiment 1. An aptamer comprising at least one first 5-position modified pyrimidine and at least one second 5-position modified pyrimidine, wherein the first 5-position modified pyrimidine and the second 5-position modified pyrimidine are different 5-position modified pyrimidines.

Embodiment 2. The aptamer of embodiment 1, wherein the first 5-position modified pyrimidine is a 5-position modified uridine and wherein the second 5-position modified pyrimidine is a 5-position modified cytidine.

Embodiment 3. The aptamer of embodiment 1, wherein the first 5-position modified pyrimidine is a 5-position modified cytidine and wherein the second 5-position modified pyrimidine is a 5-position modified uridine.

Embodiment 4. The aptamer of embodiment 2 or embodiment 3, wherein the 5-position modified uridine comprises a moiety at the 5-position selected from a naphthyl moiety, a benzyl moiety, a tyrosyl moiety, an indole moiety and a morpholino moiety.

Embodiment 5. The aptamer of any one of embodiments 2 to 4, wherein the 5-position modified cytidine comprises a moiety at the 5-position selected from a naphthyl moiety, a benzyl moiety, a tyrosyl moiety, and a morpholino moiety.

Embodiment 6. The aptamer of any one of embodiments 2 to 5, wherein the 5-position modified cytidine is selected from a NapdC, a 2NapdC, a TyrdC, and a PPdC.

Embodiment 7. The aptamer of any one of embodiments 2 to 6, wherein the 5-position modified uridine is selected from a NapdU, a 2NapdU, a PPdU, a MOEdU, a TyrdU, a TrpdU, and a ThrdU.

Embodiment 8. The aptamer of embodiment 1, wherein the at least one first 5-position modified pyrimidine is a NapdC and the at least one second 5-position modified pyrimidine is selected from a NapdU, a 2NapdU, a PPdU, a MOEdU, a TyrdU, and a ThrdU.

Embodiment 9. The aptamer of embodiment 1, wherein the at least one first 5-position modified pyrimidine is a PPdC and the at least one second 5-position modified pyrimidine is selected from a NapdU, a 2NapdU, a PPdU, a MOEdU, a TyrdU, and a ThrdU.

Embodiment 10. The aptamer of embodiment 8 or embodiment 9, wherein the at least one second 5-position modified pyrimidine is a TyrdU.

Embodiment 11. The aptamer of any one of embodiments 1 to 10, wherein the aptamer binds a target protein selected from PCSK9, PSMA, ErbB1, ErbB2, FXN, KDM2A, IGF1R, pIGF1R, a1-Antritrypsin, CD99, MMP28 and PPIB.

Embodiment 12. The aptamer of any one of embodiments 1 to 11, wherein the aptamer comprises a region at the 5' end of the aptamer that is at least 10, at least 15, at least 20, at least 25 or at least 30 nucleotides in length, or 5 to 30, 10 to 30, 15 to 30, 5 to 20, or 10 to 20 nucleotides in length, wherein the region at the 5' end of the aptamer lacks 5-position modified pyrimidines.

Embodiment 13. The aptamer of any one of embodiments 1 to 12, wherein the aptamer comprises a region at the 3' end of the aptamer that is at least 10, at least 15, at least 20, at least 25 or at least 30 nucleotides in length, or 5 to 30, 10 to 30, 15 to 30, 5 to 20, or 10 to 20 nucleotides in length, wherein the region at the 3' end of the aptamer lacks 5-position modified pyrimidines.

Embodiment 14. The aptamer of any one of embodiments 1 to 13, wherein the aptamer is 20 to 100, or 20 to 90, or 20 to 80, or 20 to 70, or 20 to 60, or 20 to 50, or 30 to 100, or 30 to 90, or 30 to 80, or 30 to 70, or 30 to 60, or 30 to 50, or 40 to 100, or 40 to 90, or 40 to 80, or 40 to 70, or 40 to 60, or 40 to 50 nucleotides in length.

Embodiment 15. A composition comprising a plurality of polynucleotides, wherein each polynucleotide comprises at least one first 5-position modified pyrimidine and at least one second 5-position modified pyrimidine, wherein the first 5-position modified pyrimidine and the second 5-position modified pyrimidine are different 5-position modified pyrimidines.

Embodiment 16. The composition of embodiment 15, wherein each polynucleotide comprises a fixed region at the 5' end of the polynucleotide.

Embodiment 17. The composition of embodiment 16, wherein the fixed region at the 5' end of each polynucleotide is at least 10, at least 15, at least 20, at least 25 or at least 30 nucleotides in length, or 5 to 30, 10 to 30, 15 to 30, 5 to 20, or 10 to 20 nucleotides in length.

Embodiment 18. The composition of any one of embodiments 15 to 17, wherein each polynucleotide comprises a fixed region at the 3' end of the polynucleotide.

Embodiment 19. The composition of embodiment 18, wherein the fixed region at the 3' end of the polynucleotide is at least 10, at least 15, at least 20, at least 25 or at least 30 nucleotides in length, or 5 to 30, 10 to 30, 15 to 30, 5 to 20, or 10 to 20 nucleotides in length.

Embodiment 20. The composition of any one of embodiments 15 to 19, wherein the first 5-position modified pyrimidine is a 5-position modified uridine and wherein the second 5-position modified pyrimidine is a 5-position modified cytidine.

Embodiment 21. The composition of any one of embodiments 15 to 19, wherein the first 5-position modified pyrimidine is a 5-position modified cytidine and wherein the second 5-position modified pyrimidine is a 5-position modified uridine.

Embodiment 22. The composition of embodiment 20 or embodiment 21, wherein the 5-position modified uridine comprises a moiety at the 5-position selected from a naphthyl moiety, a benzyl moiety, a tyrosyl moiety, an indole moiety and a morpholino moiety.

Embodiment 23. The composition of any one of embodiments 20 to 22, wherein the 5-position modified cytidine comprises a moiety at the 5-position selected from a naphthyl moiety, a benzyl moiety, a tyrosyl moiety, and a morpholino moiety.

Embodiment 24. The composition of any one of embodiments 20 to 23, wherein the 5-position modified cytidine is selected from NapdC, 2NapdC, TyrdC, and PPdC.

Embodiment 25. The composition of any one of embodiments 20 to 24, wherein the 5-position modified uridine is selected from NapdU, 2NapdU, PPdU, MOEdU, TyrdU, TrpdU, and ThrdU.

Embodiment 26. The composition of embodiment 15, wherein the at least one first 5-position modified pyrimidine is a NapdC and the at least one second 5-position modified pyrimidine is selected from NapdU, 2NapdU, PPdU, MOEdU, TyrdU, TrpdU, and ThrdU.

Embodiment 27. The composition of embodiment 15, wherein the at least one first 5-position modified pyrimidine is a PPdC and the at least one second 5-position modified pyrimidine is selected from NapdU, 2NapdU, PPdU, MOEdU, TrydU, TrpdU, and ThrdU.

Embodiment 28. The composition of embodiment 26 or embodiment 27, wherein the at least one second 5-position modified pyrimidine is a TyrdU.

Embodiment 29. The composition of any one of embodiments 15 to 28, wherein each polynucleotide comprises a random region.

Embodiment 30. The composition of embodiment 29, wherein the random region is 20 to 100, or 20 to 90, or 20 to 80, or 20 to 70, or 20 to 60, or 20 to 50, or 20 to 40, or 30 to 100, or 30 to 90, or 30 to 70, or 30 to 60, or 30 to 50, or 30 to 40 nucleotides in length.

Embodiment 31. The composition of any one of embodiments 15 to 29, wherein each polynucleotide is 20 to 100, or 20 to 90, or 20 to 80, or 20 to 70, or 20 to 60, or 20 to 50, or 30 to 100, or 30 to 90, or 30 to 80, or 30 to 70, or 30 to 60, or 30 to 50, or 40 to 100, or 40 to 90, or 40 to 80, or 40 to 70, or 40 to 60, or 40 to 50 nucleotides in length.

Embodiment 32. A composition comprising a first aptamer, a second aptamer, and a target,
wherein the first aptamer comprises at least one first 5-position modified pyrimidine and at least one second 5-position modified pyrimidine;
wherein the second aptamer comprises at least one third 5-position modified pyrimidine;
wherein the first aptamer, second aptamer and the target are capable of forming a trimer complex; and
wherein the first 5-position modified pyrimidine and the second 5-position modified pyrimidine are different 5-position modified pyrimidines.

Embodiment 33. The composition of embodiment 32, wherein the first 5-position modified pyrimidine is a 5-position modified uridine and wherein the second 5-position modified pyrimidine is a 5-position modified cytidine.

Embodiment 34. The composition of embodiment 32, wherein the first 5-position modified pyrimidine is a 5-position modified cytidine and wherein the second 5-position modified pyrimidine is a 5-position modified uridine.

Embodiment 35. The composition of embodiment 33 or embodiment 34, wherein the 5-position modified uridine comprises a moiety at the 5-position selected from a naphthyl moiety, a benzyl moiety, a tyrosyl moiety, an indole moiety and a morpholino moiety.

Embodiment 36. The composition of any one of embodiments 33 to 35, wherein the 5-position modified cytidine comprises a moiety at the 5-position selected from a naphthyl moiety, a benzyl moiety, a tyrosyl moiety, and a morpholino moiety.

Embodiment 37. The composition of any one of embodiments 33 to 36, wherein the 5-position modified cytidine is selected from NapdC, 2NapdC, TyrdC, and PPdC.

Embodiment 38. The composition of any one of embodiments 33 to 37, wherein the 5-position modified uridine is selected from NapdU, 2NapdU, PPdU, MOEdU, TyrdU, TrpdU, and ThrdU.

Embodiment 39. The composition of embodiment 32, wherein the at least one first 5-position modified pyrimidine is a NapdC and the at least one second 5-position modified pyrimidine is selected from NapdU, 2NapdU, PPdU, MOEdU, TyrdU, TrpdU, and ThrdU.

Embodiment 40. The composition of embodiment 32, wherein the at least one first 5-position modified pyrimidine is a PPdC and the at least one second 5-position modified pyrimidine is selected from NapdU, 2NapdU, PPdU, MOEdU, TyrdU, TrpdU, and ThrdU.

Embodiment 41. The composition of embodiment 39 or embodiment 40, wherein the at least one second 5-position modified pyrimidine is a TyrdU.

Embodiment 42. The composition of any one of embodiments 32 to 41, wherein the third 5-position modified pyrimidine is selected from a 5-position modified cytidine and a 5-position modified pyrimidine.

Embodiment 43. The composition of embodiment 42, wherein the third 5-position modified pyrimidine is selected from BndC, PEdC, PPdC, NapdC, 2NapdC, NEdC, 2NEdC, TyrdC, BndU, NapdU, PEdU, IbdU, FBndU, 2NapdU, NEdU, MBndU, BFdU, BTdU, PPdU, MOEdU, TyrdU, TrpdU, and ThrdU.

Embodiment 44. The composition of any one of embodiments 32 to 43, wherein the target is selected from a protein, a peptide, a carbohydrate, a small molecule, a cell and a tissue.

Embodiment 45. A method comprising:
(a) contacting an aptamer capable of binding to a target molecule with a sample;
(b) incubating the aptamer with the sample to allow an aptamer-target complex to form;
(c) enriching for the aptamer-target complex in the sample and
(c) detecting for the presence of the aptamer, aptamer-target complex or target molecule, wherein the detection of the aptamer, aptamer-target complex or target molecule indicates that the target molecule is present in the sample, and wherein the lack of detection of the aptamer, aptamer-target complex or target molecule indicates that the target molecule is not present in the sample;
wherein the aptamer is an aptamer of any one of embodiments 1 to 14.

Embodiment 46. The method of embodiment 45, wherein the method comprises at least one additional step selected from: adding a competitor molecule to the sample; capturing the aptamer-target complex on a solid support; and adding a competitor molecule and diluting the sample; wherein the at least one additional step occurs after step (a) or step (b).

Embodiment 47. The method of embodiment 46, wherein the competitor molecule is selected from a polyanionic competitor.

Embodiment 48. The method of embodiment 47, wherein the polyanionic competitor is selected from an oligonucleotide, polydextran, DNA, heparin and dNTPs.

Embodiment 49. The method of embodiment 48, wherein polydextran is dextran sulfate; and DNA is herring sperm DNA or salmon sperm DNA.

Embodiment 50. The method of any one of embodiments 45 to 49, wherein the target molecule is selected from a protein, a peptide, a carbohydrate, a small molecule, a cell and a tissue.

Embodiment 51. The method of any one of embodiments 45 to 50, wherein the sample is selected from whole blood, leukocytes, peripheral blood mononuclear cells, plasma, serum, sputum, breath, urine, semen, saliva, meningial fluid, amniotic fluid, glandular fluid, lymph fluid, nipple aspirate, bronchial aspirate, synovial fluid, joint aspirate, cells, a cellular extract, stool, tissue, a tissue biopsy, and cerebrospinal fluid.

Embodiment 52. A method for detecting a target in a sample comprising
a) contacting the sample with a first aptamer to form a mixture, wherein the first aptamer is capable of binding to the target to form a first complex;
b) incubating the mixture under conditions that allow for the first complex to form;
c) contacting the mixture with a second aptamer, wherein the second aptamer is capable of binding the first complex to form a second complex;
d) incubating the mixture under conditions that allow for the second complex to form;
e) detecting for the presence or absence of the first aptamer, the second aptamer, the target, the first complex or the second complex in the mixture, wherein the presence of the first aptamer, the second aptamer, the target, the first complex or the second complex indicates that the target is present in the sample;

wherein the first aptamer comprises at least one first 5-position modified pyrimidine and at least one second 5-position modified pyrimidine;

wherein the second aptamer comprises at least one third 5-position modified pyrimidine;

wherein the first 5-position modified pyrimidine and the second 5-position modified pyrimidine are different 5-position modified pyrimidines.

Embodiment 53. The method of embodiment 52, wherein the first 5-position modified pyrimidine is a 5-position modified uridine and wherein the second 5-position modified pyrimidine is a 5-position modified cytidine.

Embodiment 54. The method of embodiment 53, wherein the first 5-position modified pyrimidine is a 5-position modified cytidine and wherein the second 5-position modified pyrimidine is a 5-position modified uridine.

Embodiment 55. The method of embodiment 53 or embodiment 54, wherein the 5-position modified uridine comprises a moiety at the 5-position selected from a naphthyl moiety, a benzyl moiety, a tyrosyl moiety, an indole moiety and a morpholino moiety.

Embodiment 56. The method of any one of embodiments 53 to 55, wherein the 5-position modified cytidine comprises a moiety at the 5-position selected from a naphthyl moiety, a benzyl moiety, a tyrosyl moiety, and a morpholino moiety.

Embodiment 57. The method of any one of embodiments 53 to 56, wherein the 5-position modified cytidine is selected from NapdC, 2NapdC, TyrdC, and PPdC.

Embodiment 58. The method of any one of embodiments 53 to 57, wherein the 5-position modified uridine is selected from NapdU, 2NapdU, PPdU, MOEdU, TyrdU, TrpdU, and ThrdU.

Embodiment 59. The method of embodiment 52, wherein the at least one first 5-position modified pyrimidine is a NapdC and the at least one second 5-position modified pyrimidine is selected from NapdU, 2NapdU, PPdU, MOEdU, TyrdU, TrpdU, and ThrdU.

Embodiment 60. The method of embodiment 52, wherein the at least one first 5-position modified pyrimidine is a PPdC and the at least one second 5-position modified pyrimidine is selected from NapdU, 2NapdU, PPdU, MOEdU, TyrdU, TrpdU, and ThrdU.

Embodiment 61. The method of embodiment 59 or embodiment 60, wherein the at least one second 5-position modified pyrimidine is a TyrdU.

Embodiment 62. The method of any one of embodiments 52 to 61, wherein the third 5-position modified pyrimidine is selected from a 5-position modified cytidine and a 5-position modified pyrimidine.

Embodiment 63. The method of embodiment 62, wherein the third 5-position modified pyrimidine is selected from BndC, PEdC, PPdC, NapdC, 2NapdC, NEdC, 2NEdC, TyrdC, BNdU, NapdU, PedU, IbdU, FbndU, 2NapdU, NedU, MbndU, BfdU, BtdU, PpdU, MOEdU, TyrdU, TrpdU, and ThrdU.

Embodiment 64. The method of any one of embodiments 52 to 63, wherein the target molecule is selected from a protein, a peptide, a carbohydrate, a small molecule, a cell and a tissue.

Embodiment 65. The method of any one of embodiments 52 to 64, wherein the first aptamer, second aptamer and the target are capable of forming a trimer complex.

Embodiment 66. A method for identifying one or more aptamers capable of binding to a target molecule comprising:

(a) contacting a library of aptamers with the target molecule to form a mixture, and allowing for the formation of an aptamer-target complex, wherein the aptamer-target complex forms when an aptamer has affinity for the target molecule;

(b) partitioning the aptamer-target complex from the remainder of the mixture (or enriching for the aptamer-target complex);

(c) dissociating the aptamer-target complex; and (d) identifying the one or more aptamers capable of binding to the target molecule;

wherein the library of aptamers comprises a plurality of polynucleotides, wherein each polynucleotide comprises at least one first 5-position modified pyrimidine and at least one second 5-position modified pyrimidine, wherein the first 5-position modified pyrimidine and the second 5-position modified pyrimidine are different 5-position modified pyrimidines.

Embodiment 67. The method of embodiment 66, wherein each polynucleotide comprises a fixed region at the 5' end of the polynucleotide.

Embodiment 68. The method of embodiment 67, wherein the fixed region at the 5' end of each polynucleotide is at least 10, at least 15, at least 20, at least 25 or at least 30 nucleotides in length, or 5 to 30, 10 to 30, 15 to 30, 5 to 20, or 10 to 20 nucleotides in length.

Embodiment 69. The method of any one of embodiments 66 to 68, wherein each polynucleotide comprises a fixed region at the 3' end of the polynucleotide.

Embodiment 70. The method of embodiment 69, wherein the fixed region at the 3' end of the polynucleotide is at least 10, at least 15, at least 20, at least 25 or at least 30 nucleotides in length, or 5 to 30, 10 to 30, 15 to 30, 5 to 20, or 10 to 20 nucleotides in length.

Embodiment 71. The method of any one of embodiments 66 to 70, wherein the first 5-position modified pyrimidine is a 5-position modified uridine and wherein the second 5-position modified pyrimidine is a 5-position modified cytidine.

Embodiment 72. The method of any one of embodiments 66 to 71, wherein the first 5-position modified pyrimidine is a 5-position modified cytidine and wherein the second 5-position modified pyrimidine is a 5-position modified uridine.

Embodiment 73. The method of embodiment 71 or embodiment 72, wherein the 5-position modified uridine comprises a moiety at the 5-position selected from a naphthyl moiety, a benzyl moiety, a tyrosyl moiety, an indole moiety and a morpholino moiety.

Embodiment 74. The method of any one of embodiments 71 to 73, wherein the 5-position modified cytidine comprises a moiety at the 5-position selected from a naphthyl moiety, a benzyl moiety, a tyrosyl moiety and a morpholino moiety.

Embodiment 75. The method of any one of embodiments 71 to 74, wherein the 5-position modified cytidine is selected from NapdC, 2NapdC, TyrdC, and PPdC.

Embodiment 76. The method of any one of embodiments 71 to 75, wherein the 5-position modified uridine is selected from NapdU, PPdU, MOEdU, TyrdU, TrpdU, and ThrdU.

Embodiment 77. The method of embodiment 66, wherein the at least one first 5-position modified pyrimidine is a NapdC and the at least one second 5-position modified pyrimidine is selected from NapdU, 2NapdU, PPdU, MOEdU, TrydU, TrpdU and ThrdU.

Embodiment 78. The method of embodiment 66, wherein the at least one first 5-position modified pyrimidine is a PPdC and the at least one second 5-position modified pyrimidine is selected from NapdU, 2NapdU, PPdU, MOEdU, TyrdU, TrpdU, and ThrdU.

Embodiment 79. The method of embodiment 77 or embodiment 78, wherein the at least one second 5-position modified pyrimidine is a TyrdU.

Embodiment 80. The method of any one of embodiments 66 to 79, wherein each polynucleotide comprises a random region.

Embodiment 81. The method of embodiment 80, wherein the random region is 20 to 100, or 20 to 90, or 20 to 80, or 20 to 70, or 20 to 60, or 20 to 50, or 20 to 40, or 30 to 100, or 30 to 90, or 30 to 70, or 30 to 60, or 30 to 50, or 30 to 40 nucleotides in length.

Embodiment 82. The method of any one of embodiments 66 to 81, wherein each polynucleotide is 20 to 100, or 20 to 90, or 20 to 80, or 20 to 70, or 20 to 60, or 20 to 50, or 30 to 100, or 30 to 90, or 30 to 80, or 30 to 70, or 30 to 60, or 30 to 50, or 40 to 100, or 40 to 90, or 40 to 80, or 40 to 70, or 40 to 60, or 40 to 50 nucleotides in length.

Embodiment 83. The method of any one of embodiments 66 to 82, wherein each polynucleotide is an aptamer that binds a target, and wherein the library comprises at least 1000 aptamers, wherein each aptamer comprises a different nucleotide sequence.

Embodiment 84. The method of any one of embodiments 66 to 83, wherein steps (a), (b) and/or (c) are repeated at least one time, two times, three times, four times, five times, six times, seven times, eight times, nine times or ten times.

Embodiment 85. The method of any one of embodiments 66 to 84, wherein the one or more aptamers capable of binding to the target molecule are amplified.

Embodiment 86. The method of any one of embodiments 66 to 85, wherein the mixture comprises a polyanionic competitor molecule.

Embodiment 87. The method of embodiment 86, wherein the polyanionic competitor is selected from an oligonucleotide, polydextran, DNA, heparin and dNTPs.

Embodiment 88. The method of embodiment 87, wherein polydextran is dextran sulfate; and DNA is herring sperm DNA or salmon sperm DNA.

Embodiment 89. The method of any one of embodiments 66 to 88, wherein the target molecule is selected from a protein, a peptide, a carbohydrate, a small molecule, a cell and a tissue.

Embodiment 90. The aptamer of any one of embodiments 1 to 14, wherein the first 5-position modified pyrimidine and the second 5-position modified pyrimidine are capable of being incorporated by a polymerase enzyme.

Embodiment 91. The composition of any one of embodiments 15 to 44, wherein the first 5-position modified pyrimidine and the second 5-position modified pyrimidine are capable of being incorporated by a polymerase enzyme.

Embodiment 92. The method of any one of embodiments 45 to 89, wherein the first 5-position modified pyrimidine and the second 5-position modified pyrimidine are capable of being incorporated by a polymerase enzyme.

Embodiment 93. The aptamer of any one of embodiments 1 to 14 and 90, wherein the aptamer has improved nuclease stability compared to an aptamer of the same length and nucleobase sequence that comprises an unmodified pyrimidine in place of each of the first 5-position modified pyrimidines or an unmodified pyrimidine in place of each of the second 5-position modified pyrimidine.

Embodiment 94. The aptamer of any one of embodiments 1 to 14, 90, and 93, wherein the aptamer has a longer half-life in human serum compared to an aptamer of the same length and nucleobase sequence that comprises an unmodified pyrimidine in place of each of the first 5-position modified pyrimidines or an unmodified pyrimidine in place of each of the second 5-position modified pyrimidine.

EXAMPLES

The following examples are presented in order to more fully illustrate some embodiments of the invention. They should, in no way be construed, however, as limiting the broad scope of the invention. Those of ordinary skill in the art can readily adopt the underlying principles of this discovery to design various compounds without departing from the spirit of the current invention.

Example 1

Aptamers Comprising Two Modified Bases

To compare the relative efficiency of SELEX with two modified bases, five single modifications on dU (Nap-dU, PP-dU, MOE-dU, Tyr-dU and Thr-dU) with unmodified dT as a control, and combinations with modifications on dC (Nap-dC and PP-dC) with unmodified dC as a control, were analyzed, for a total of 18 starting libraries (FIG. 1). The types of modifications tested included hydrophobic aromatic side chains analogous to hydrophobic side chains on amino acids. Hydrophilic side chains on dU (MOE-dU and Thr-dU) were also tested. Each of the 18 libraries contained 30 randomized nucleotides, allowing for $\geq 10^{15}$ different sequences. The libraries were enzymatically synthesized using natural and/or modified nucleotide triphosphates using KOD DNA polymerase, Exo- (data not shown).

Thirty nucleotide (30N) randomized libraries were used instead of the previous 40N randomized libraries with single modified dUs. Without intending to be bound by any particular theory, it was postulated that increasing the density of modified bases would allow for shorter high affinity aptamers. Further, shorter oligonucleotide libraries give higher yields. The ratio of each nucleotide was 1:1:1:1 for dA/dC/dG/dT (25% each). In each case, the random region was flanked with fixed sequences for hybridizing PCR amplification primers (Table 2), with additional spacers at the 5' end and at the 3' end. The master synthetic template was used to generate modified libraries with all dU and or dC positions uniformly modified in replacement primer extension reactions.

A total of 18 enzymatically synthesized libraries comprising single modified dU (Nap-dU, PP-dU, MOE-dU, Tyr-dU and /Thr-dU) with unmodified dT as a control; single modified dC (Nap-dC and PP-dC) with unmodified dC as a control; and combination of two modified bases: either Nap-dC or PP-dC, with all possible modified dUs (Nap-dU, PP-dU, MOE-dU, Tyr-dU and Thr-dU). The qualitative primer extension reactions (in triplicates) were carried out using antisense template, radio-labeled 5' primer with natural or modified nucleotide tri-phosphates and KOD polymerase (Exo-) in solution, as follows. In a 60 μL primer extension reaction, 20 pmoles of biotinylated anti-sense library was mixed with 40 pmoles of 5' cold primer (2×) and trace amounts of $^{32}$P labeled 5' primer, 0.5 mM natural or modified dNTP in 1× SQ20 buffer (120 mM Tris-HCl, pH 7.8; 10 mM KCl; 6 mM $(NH_4)_2SO_4$; 7 mM $MgSO_4$, 0.1% Triton X-100 and 0.1 mg/mL BSA) and 0.25 U/mL KOD Polymerase (Exo-). The mixture was heat cooled before adding DNA polymerase and the reaction was carried out at 68° C. for 2 hr, then cooled at 10° C. The fraction from each of the library reactions were ran on 10% TBU Urea gel along with free labeled primer. Small aliquot was run on denaturing gels which were exposed to phosphor screens and imaged with Fuji phosphorimager, bands were quantitated using ImageGauge 4.0 software and results were plotted in Graph pad Prism software 6.05. For making initial libraries large scale primer extension reactions were carried out using master biotinylated antisense random library captured on PierceTM High Capacity Streptavidin Agarose beads (Life Technologies). Lower library yields were obtained for certain two modified nucleoside combinations, for example, 28±1.3% for Nap-dC/Nap-dU, 40±5.2% for Nap-dC/MOE-dU, and 43±2.7% for PP-dC/Nap-dU, compared to 100% unmodified DNA (dC/dT) library control. The frequency of each nucleotide was calculated from the sequencing results obtained from the initial library and the master antisense random template used to generate each of the single and two base modified libraries. The master random antisense template (30N) was chemically synthesized with 1:1:1:1 ratio of dA:dG:dC:dT (TriLink Biotechnologies) at 1 µM scale. The initial random single base and two base modified libraries were enzymatically synthesized in large scale reaction and used in selection experiments. These libraries were sequenced along with the enriched pools and nucleotide frequencies were plotted with total 100% for all four bases in 30N random region. No significant bias was observed in the nucleotide frequencies when base composition of libraries was determined using deep sequencing compared with starting synthetic natural DNA template library and enzymatically synthesized unmodified DNA control initial library (data not shown).

The libraries were used to select aptamers that bind PCSK9. The selections were carried out substantially as reported previously using dextran sulphate as polyanionic competitor for a total of six rounds applying incremental target dilution during each successive rounds of selection. See Table 1 (R1=round 1, R2=round 2, etc.). Selection was started by mixing modified random libraries (or control unmodified) (≥1000 pmol) and a human recombinant His-tagged target protein, PCSK9, which was present at 0.5 µM concentration, in 100 µL volume. The selected complexes were partitioned on magnetic His-tag capture Dynabeads®, unbound sequences were washed, selected aptamers were eluted and PCR amplified using all natural nucleotides and 3' biotin-primer. The natural double-stranded DNA biotinylated at 3' end was captured on Dynabeads® MyOne™ Streptavidin C1 beads, sense strands eliminated by alkali denaturation and replaced with modified dC and or dU in primer extension reactions to regenerate enriched pool and selection cycle was repeated with diluted protein. The concentration of protein for the next round of SELEX was determined based on signal to background ratio calculated from critical cycle time (Ct) value for each sample.

TABLE 1

In vitro selection conditions

| Library composition | R1 DNA [nM] | R2-R6 DNA [nM] | PCSK9 [nM] | | | | | |
|---|---|---|---|---|---|---|---|---|
| | | | R1 | R2 | R3 | R4 | R5 | R6 |
| dC/dT (Control DNA) | 10,000 | 100 | 500 | 100 | 50 | 50 | 50 | 50 |
| Nap-dC/dT | 10,000 | 100 | 500 | 100 | 100 | 10 | 10 | 0.1 |
| PP-dC/dT | 10,000 | 100 | 500 | 100 | 100 | 100 | 100 | 10 |
| dC/Nap-dU | 10,000 | 100 | 500 | 100 | 50 | 50 | 5 | 0.5 |
| dC/PP-dU | 10,000 | 100 | 500 | 100 | 100 | 100 | 10 | 1 |
| dC/MOE-dU | 10,000 | 100 | 500 | 100 | 100 | 100 | 100 | 100 |
| dC/Tyr-dU | 10,000 | 100 | 500 | 100 | 100 | 100 | 50 | 5 |
| dC/Thr-dU | 10,000 | 100 | 500 | 100 | 100 | 100 | 100 | 10 |
| Nap-dC/ Nap-dU | 10,000 | 100 | 500 | 100 | 50 | 10 | 1 | 0.1 |
| Nap-dC/ PP-dU | 10,000 | 100 | 500 | 100 | 100 | 10 | 1 | 0.1 |
| Nap-dC/ MOE-dU | 10,000 | 100 | 500 | 100 | 100 | 100 | 10 | 1 |
| Nap-dC/ Tyr-dU | 10,000 | 100 | 500 | 100 | 100 | 10 | 1 | 0.1 |
| Nap-dC/ Thr-dU | 10,000 | 100 | 500 | 100 | 100 | 100 | 10 | 1 |
| PP-dC/ PP-dU | 10,000 | 100 | 500 | 100 | 100 | 100 | 10 | 1 |
| PP-dC/ Nap-dU | 10,000 | 100 | 500 | 100 | 100 | 100 | 10 | 1 |
| PP-dC/ MOE-dU | 10,000 | 100 | 500 | 100 | 100 | 100 | 100 | 100 |
| PP-dC/ Tyr-dU | 10,000 | 100 | 500 | 100 | 50 | 10 | 1 | 0.1 |
| PP-dC/ Thr-dU | 10,000 | 100 | 500 | 100 | 100 | 100 | 10 | 1 |

The 5' primer for amplification comprised a (AT4)-tail and the 3' primer comprised a (A-biotin)2-T8-tail (SEQ ID NO: 82), which avoids addition of modified dC or dU when modified libraries are synthesized.

TABLE 2

Sequence of natural DNA template, primers used in SELEX

| Name | Sequence |
|---|---|
| Anti-AB2-30N41.36 SEQ ID NO: 1 | (Ab2)TTTTTTTTCTCTTTCTCTTCTCTCTTTCTCC30NGACCCACCCAGCGTGG |
| (AT)4-5P41 SEQ ID NO: 2 | ATATATATCCACGCTGGGTGGGTC |
| (AB)2(T)8-3P3 SEQ ID NO: 3 | (Ab2)TTTTTTTTCTCTTTCTCTTCTCTCTTTCTCC |

Figure 2:
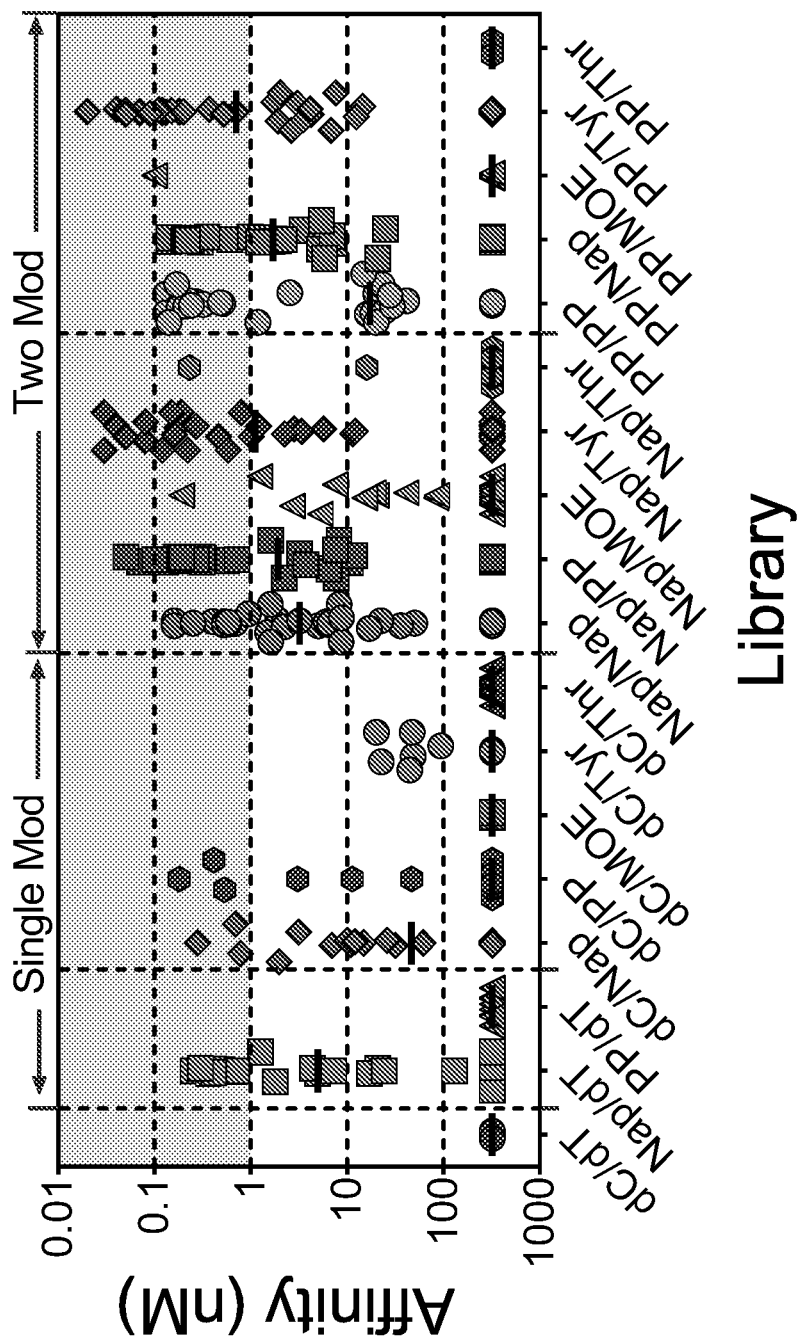
FIG. 2. Binding affinities of 40 mer (30N+5+5) aptamers to PCSK9 generated using various modified libraries. Aptamers with affinities≥1 nM are highlighted in gray shade and aptamers shown at 320 nM affinity represent no detectable binding at 32 nM top concentration on binding curve. Black line on each of the library indicates median value for the all aptamers in that library.
Figure 3:
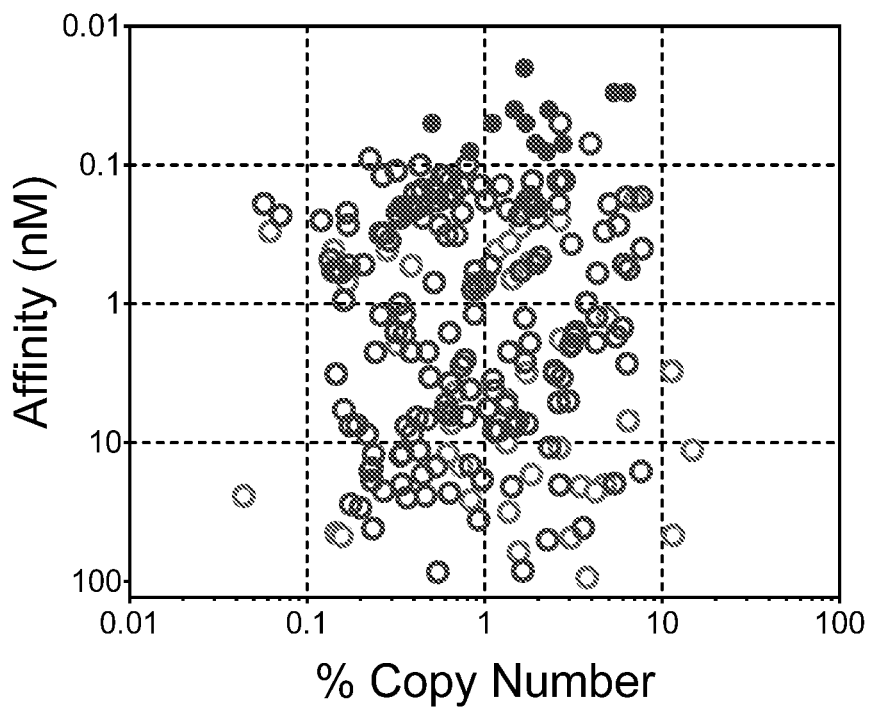
FIG. 3. The affinity and percent copy number for single modified, either dU or dC vs two modified dC with dU. Each dot represents one of the aptamers with affinity values shown on Y-axis and their percent copy number on X-axis. Red dots are single modified aptamers and green dots (open and filled) are two modified aptamers. Filled green dots represent some Nap-dC/Tyr-dU and PP-dC/Tyr-dU aptamers.

After six rounds of selections, aptamers containing natural nucleotides were deep sequenced using Ion Torrent PGM instrument. Sequence analysis was performed using custom software using local batch alignment. The data from sequence analysis of all the enriched pools demonstrated that the two modified library combinations resulted in higher diversity in enriched sequences compared with single modified libraries (data not shown). To test binding affinity of aptamers, an extensive set of sequences was chose representing not just high copy unique sequences but also low copy sequences from distinct families (data not shown). All the aptamers were chemically synthesized by standard solid phase phosphoramidite chemistry using modified/unmodified phoshoramidites reagents. All aptamers were initially screened as truncated 40 mers containing 30 nucleotide random region and additional 5 nucleotides from fixed primer regions from 5' and 3' ends for their PCSK9 binding affinities in solution with radio-labeled filter-binding assays. The truncated aptamers (40 mers) comprised 10 nucleotides from the fixed regions. The unmodified control DNA library (dC/dT) did not result in any active sequences ($K_d$<32 nM), which was expected as pool affinity for this library was flat (data not shown) and also deep sequencing data did not yield any enriched multi-copy sequences (data not shown). The single modified libraries, with Nap (naphthyl) modification either on dC or dU resulted in aptamers having affinity for the target, however, the aptamers having the greatest affinity for the target were obtained with Nap (naphthyl moiety) or PP (benzyl moiety) modified dC with Tyr (tyrosyl moiety) modified dU (FIG. 2). The replacement of Tyr-dU's with dT's abolished binding to the target, which indicates importance of tyrosyl moieties for binding interactions to target surface of PCSK9 (data not shown). The affinity datademonstrated that two modified nucleotide aptamers, in general, had greater affinity than single modified nucleotide aptamers, and also provided a greater number of aptamers than bound to PCSK9 when compared with single modified nucleotide aptamers (FIG. 3). Further, high copy single modified nucleotide aptamers have average affinities between 0.1-100 nM, while high copy two modified nucleotide aptamers have average affinities≤0.1 nM.

A summary of the data comparing single modified aptamers (40-mers) and dual-modified aptamers (40-mers) for PCSK9 is shown in the table 3 below.

TABLE 3

Binding Data Summary for Single and Dual Modified Aptamers for PCSK9
PCSK9 Target

| Category | 5-Position Modification Of Aptamer | % of Aptamers Tested with a Kd ≤ 10 nM | Total # of Aptamers Tested | Kd for Aptamer with Greatest Affinity for Target | Total # of Aptamers with no Binding | % of Aptamers with no Binding |
|---|---|---|---|---|---|---|
| Control (unmodified) | dC/dT | 0% | 19 | N/A | 19 | 100% |
| Single Mod. | NapdC/dT | 57% | 23 | 0.25 nM | 6 | 26% |
| | PPdC/dT | 0% | 8 | N/A | 8 | 100% |
| | dC/NapdU | 29% | 24 | 0.28 nM | 11 | 46% |
| | dC/PPdU | 22% | 18 | 0.18 nM | 12 | 67% |
| | dC/MOEdU | 0% | 7 | N/A | 7 | 100% |
| | dC/TyrdU | 0% | 15 | 20 nM | 9 | 60% |
| | dC/ThrdU | 0% | 18 | N/A | 18 | 100% |
| Two Mod. | NapdC/NapdU | 70% | 37 | 0.16 nM | 7 | 19% |
| | NapdC/PPdU | 72% | 32 | 0.05 nM | 7 | 22% |
| | NapdC/MOEdU | 20% | 25 | 0.19 nM | 14 | 56% |
| | NapdC/TyrdU | 65% | 34 | 0.03 nM | 10 | 29% |
| | NapdC/ThrdU | 3% | 40 | 0.23 nM | 38 | 95% |
| | PPdC/PPdU | 44% | 34 | 0.13 nM | 9 | 26% |
| | PPdCNapdU | 78% | 32 | 0.14 nM | 5 | 16% |
| | PPdC/MOEdU | 17% | 6 | 0.1 nM | 5 | 83% |
| | PPdC/TyrdU | 80% | 35 | 0.04 nM | 5 | 14% |
| | PPdC/ThrdU | 0% | 35 | N/A | 35 | 100% |

Based on the information in table 3, the percent of all single modified aptamers assayed that showed no binding was 62%. No binding is defined as an aptamer having a Kd of 320 nM or greater. The percent of all single modified aptamers with a Kd≤10 nM was less than 21%, and the average Kd for all single modified aptamers was 5,2 nM. In contrast, the percent of all two modified (dual mod.) aptamers assayed that showed no binding was 43%. Further, the percent of all two modified aptamers with a Kd≤10 nM was 47%, and the average Kd for all two modified aptamers was 0.12 nM.

Example 2

Truncation of Dual-Modified Aptamers

Figure 4A:
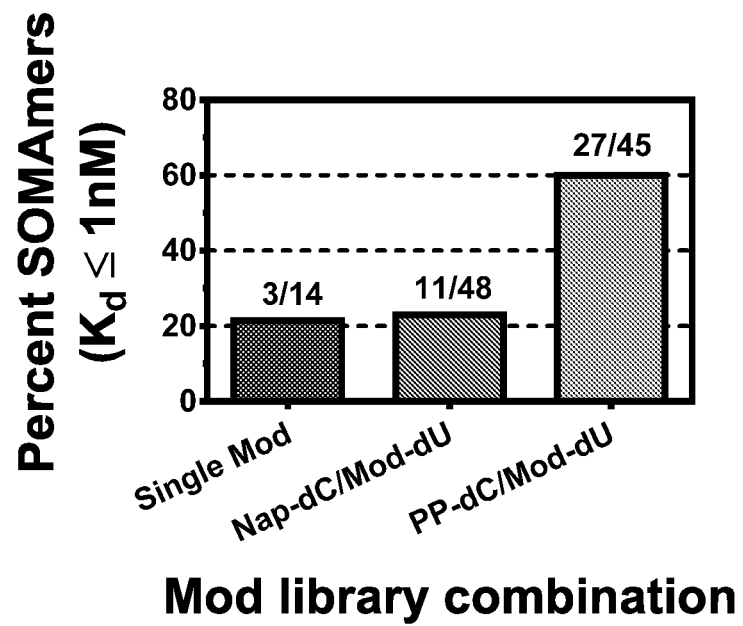
FIG. 4A-B. Truncability of single base modified and two base modified aptamers. (A) All high affinity 40 mer sequences were further truncated to 30 mer to their random region length only removing 5 nucleotides from each of the 5' and 3' ends. The percentage of aptamers that retain or have improved binding affinity to PCSK9 is plotted on Y-axis. (B) Affinity comparisons and truncability of single base modified and two base modified aptamers from each individual library. Aptamers with affinities≥1 nM are highlighted in gray shade, the highest average affinities were for aptamers with two modified base combinations of PP-dC with PP-dU, Nap-dU and Tyr-dU.
Figure 4B:
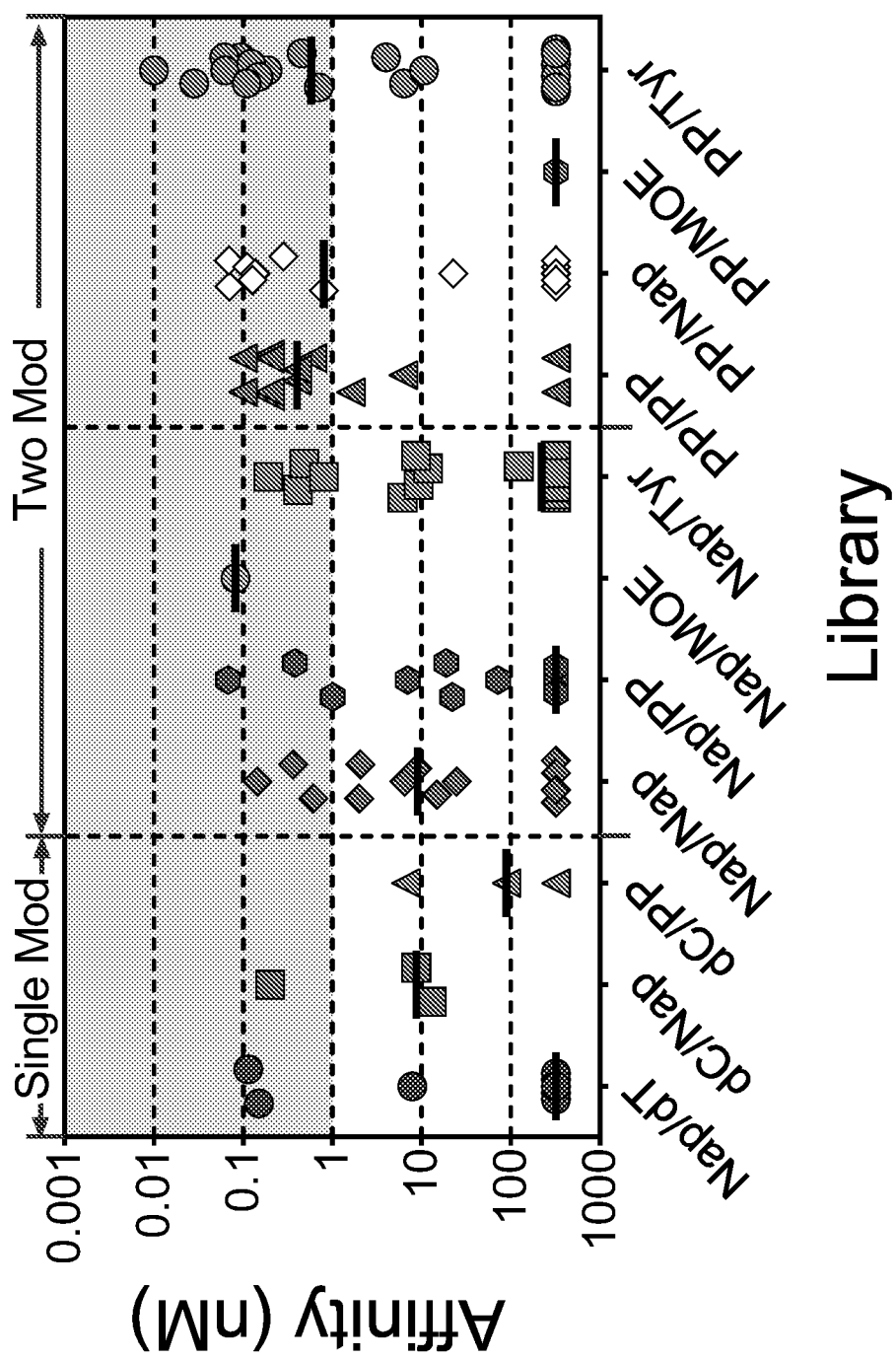

The effect of further truncation on high-affinity ($K_d$<1 nM) aptamer binding was investigated. Aptamers were truncated to 30 mers, which is a 25% reduction in length. The PP-dC/Tyr-dU combination had the highest number of aptamers that could be truncated to 30 mers, while still retaining binding affinity (FIG. 4A). Single base modified aptamers showed truncability of 21.5% (blue bar, 3/14), two base modified Nap-dC aptamers with modified dU's showed truncability of ~23% (red bar, 11/48), while two base modified PP-dC with other modified dU's showed enhanced truncability of 60% (green bar, 27/45). The percentage and the number of 40 mers that could be truncated to 30 mers were also higher for two base modified combinations of PP-dC with PP-dU, Nap-dU, or Tyr-dU compared with other libraries (FIG. 4B). Fewer aptamers from single base modified libraries were tested because there were only 14 aptamers with affinity≤1 nM from the three libraries (40 mers, in gray area in FIG. 4B for single mod). In contrast, the number of aptamers from two base modified libraries with high affinity was 93 (40 mers, in gray area of FIG. 4B for two mod), 48 for Nap-dC with modified dU's and 45 for PP-dC with modified dU's. Black horizontal line on each of the libraries indicates median value for the all aptamers in that library. Without intending to be bound by any particular theory, it is possible that extended carbon chain in the PP modified base (compared with other modifications) helps to reach inaccessible epitopes on the target surface and does not need fixed primer regions for the structural folding and effective protein binding interactions.

Figure 5:
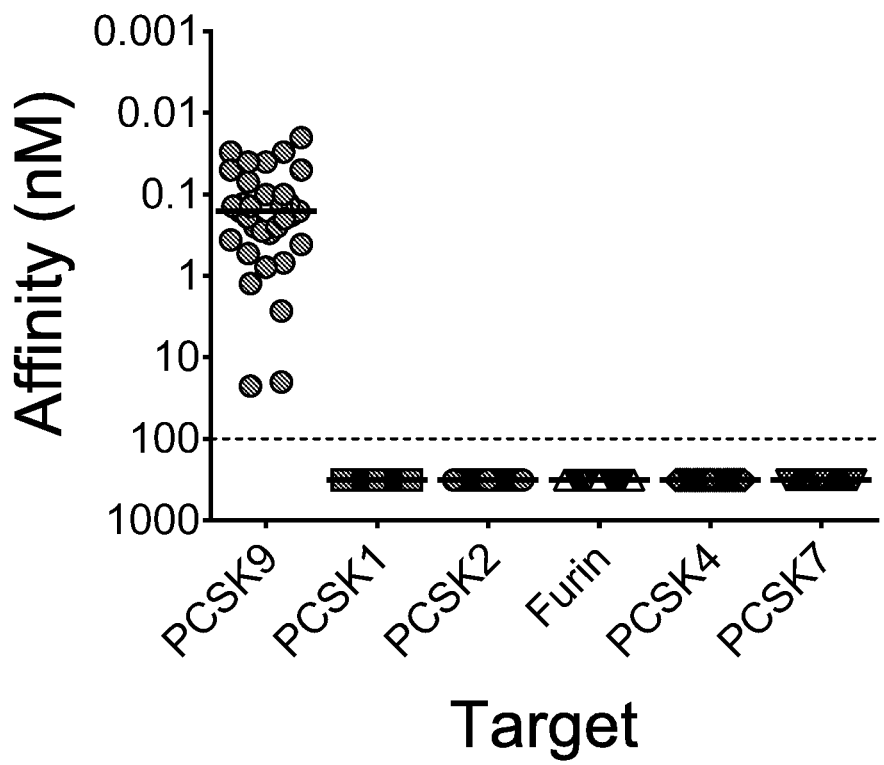
FIG. 5. Target binding specificity of three high affinity aptamers from each library to other proprotein convertases (PCs). The solution affinity measurements were carried out for thirty-three aptamers (40 mers) total, with eleven aptamers having a single modified base (i.e., three aptamers having Nap-dC/dT; three aptamers having dC/Nap-dU; three aptamers having dC/Pp-dU and two aptamers having dC/Ty-dU) and twenty-two aptamers having double modified base (i.e., three aptamers having Nap-dC/Nap-dU; three aptamers having Nap-dC/Pp-dU; three aptamers having Nap-dC/Moe-dU; three aptamers having Nap-dC/Tyr-dU; three aptamers having Pp-dC/Pp-dU; three aptamers having Pp-dC/Nap-dU; three aptamers having Pp-Ty-dU, and one aptamer having Pp-dC/Moe-dU). The aptamers below dotted line at 100 nM affinity indicates no detectable binding at 100 nM concentration. The affinities to remaining PCs (PCSK5, PCSK6 and PCSK8) were not tested.

The specificity of PCSK9 aptamers to various other proprotein convertases (PCs) was also evaluated. The three highest affinity aptamers from each library were selected (n=33, 40 mers; none from unmodified DNA control library, only two aptamers from dC/Tyr-dU library and one aptamer from PP-dC/MOE-dU library) and tested for their specificity to other PCs. The results demonstrated that the aptamers were specific to PCSK9 and no detectable binding was observed with other PCs (FIG. 5) at 100 nM concentrations.

Figure 6:
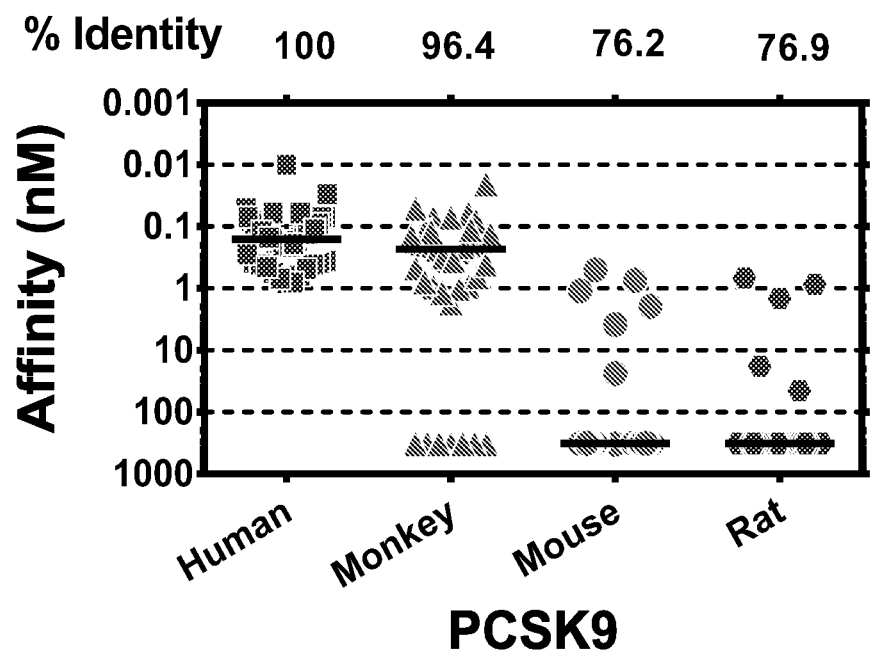
FIG. 6. Species cross-reactivity of single base and two base modified aptamers. Affinity of single modified (three aptamers) and two modified (38 aptamers) truncated 30-mer aptamers ($K_d$ value≤1 nM) to PCSK9 from human, monkey, mouse and rat. The single modified aptamers bound to the human and monkey PSCKS9, but not to the mouse or rate PSKC9. In contrast, the two modified aptamers bound to human, monkey, mouse and rat. The percent identity of the PCSK9 protein from each species is provided relative to the human PSCK9.

The cross-species reactivity of truncated aptamers (n=41, 30 mers) with $K_d$ values of ≤1 nM was tested for rodent (mouse and rat) and Rhesus monkey PCSK9 (see Table 4). The percent identity between PCSK9 from various species is shown at the top of the graph in FIG. 6. The mouse/rat PCSK9 is about 76% identical with monkey and human proteins. Most of the aptamers bound to Rhesus monkey PCSK9 with similar affinities (identity 96.4%), however, few aptamers from two modified libraries (PP-dC/Nap-dU and PP-dC/Tyr-dU) bound to rat and mouse PCSK9 (identity ~76%). These results demonstrated that certain two base modified libraries (e.g., PP-dC/Nap-dU and PP-dC/Tyr-dU) generated aptamers that can bind to both rodent and human/monkey PCSK9 with similar affinities (FIG. 6).

TABLE 4

Cross-species binding activity of single and double modified aptamers

| Library | Human PCSK9 Kd (pM) | Monkey PCSK9 Kd (pM) | Mouse PCSK9 Kd (pM) | Rat PCSK9 Kd (pM) |
|---|---|---|---|---|
| Nap-dC/dT | 150 | 149 | — | — |
| Nap-dC/dT | 114 | 56 | — | — |
| dC/Nap-dU | 223 | 174 | — | — |
| Nap-dC/Nap-dU | 362 | 461 | — | — |
| Nap-dC/Nap-dU | 609 | 1710 | — | — |
| Nap-dC/Nap-dU | 144 | 351 | — | — |
| Nap-dC/Pp-dU | 379 | 934 | — | — |
| Nap-dC/Pp-dU | 68 | 924 | — | — |
| Nap-dC/Moe-dU | 82 | 83 | — | — |
| Nap-dC/Moe-dU | 172 | 169 | — | — |
| Nap-dC/Tyr-dU | 411 | 177 | — | — |
| Nap-dC/Tyr-dU | 484 | 70 | — | — |
| Nap-dC/Tyr-dU | 191 | 193 | — | — |
| Nap-dC/Tyr-dU | 805 | 987 | — | — |
| Pp-dC/Pp-dU | 186 | 189 | — | — |
| Pp-dC/Pp-dU | 162 | 198 | — | — |
| Pp-dC/Pp-dU | 220 | 1150 | — | — |
| Pp-dC/Pp-dU | 564 | 638 | — | — |
| Pp-dC/Pp-dU | 53 | 106 | — | — |
| Pp-dC/Pp-dU | 213 | 229 | — | — |
| Pp-dC/Pp-dU | 378 | 306 | — | — |
| Pp-dC/Pp-dU | 93 | 204 | — | — |
| Pp-dC/Pp-dU | 413 | 402 | — | — |
| Pp-dC/Nap-dU | 283 | 247 | 23800 | — |
| Pp-dC/Nap-dU | 70 | 74 | 742 | 1440 |
| Pp-dC/Nap-dU | 69 | 117 | — | — |
| Pp-dC/Nap-dU | 111 | 140 | 500 | 680 |
| Pp-dC/Nap-dU | 136 | 205 | 3820 | 18100 |
| Pp-dC/Nap-dU | 800 | 780 | — | — |
| Pp-dC/Nap-dU | 127 | 128 | 1950 | 45000 |

TABLE 4-continued

Cross-species binding activity of single and double modified aptamers

| Library | Human PCSK9 Kd (pM) | Monkey PCSK9 Kd (pM) | Mouse PCSK9 Kd (pM) | Rat PCSK9 Kd (pM) |
|---|---|---|---|---|
| Pp-dC/Tyr-dU | 701 | — | — | — |
| Pp-dC/Tyr-dU | 187 | 109 | — | — |
| Pp-dC/Tyr-dU | 93 | — | — | — |
| Pp-dC/Tyr-dU | 61 | 45 | — | — |
| Pp-dC/Tyr-dU | 62 | — | — | — |
| Pp-dC/Tyr-dU | 451 | 350 | 1090 | 858 |
| Pp-dC/Tyr-dU | 12 | 21 | — | — |
| Pp-dC/Tyr-dU | 122 | — | — | — |
| Pp-dC/Tyr-dU | 28 | — | — | — |
| Pp-dC/Tyr-dU | 148 | — | — | — |
| Pp-dC/Tyr-dU | 109 | — | — | — |

—indicates that no binding was detected in the assay

Example 3

Aptamer Binding in Sandwich Assays

Figure 7A:
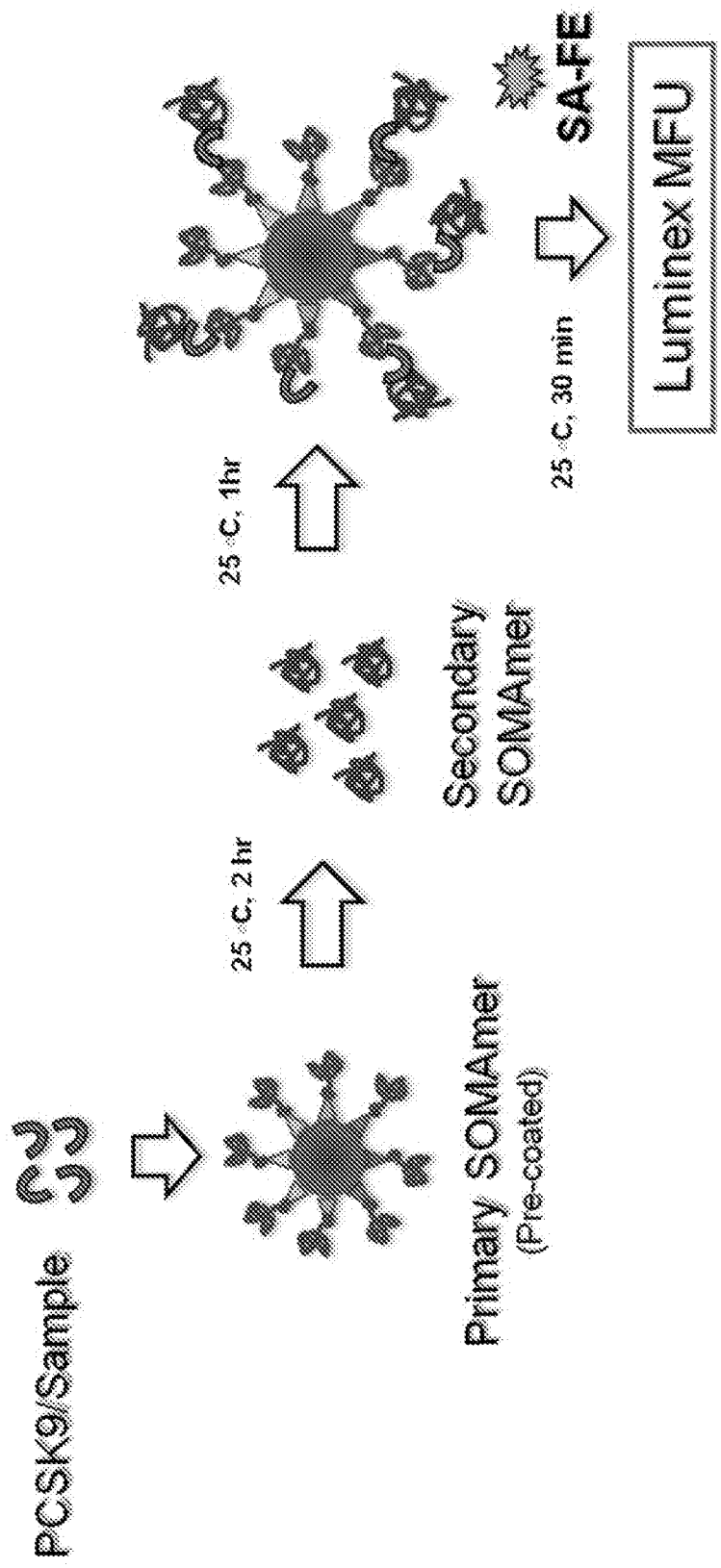
FIG. 7A-C. Sandwich pair screening in bead-based Luminex® assay. (A) Schematics of aptamer sandwic$_h$ pair screening. (B) Sandwich pairs showing signal of greater than or equal to 50-fold at 10 nM PCSK9 concentration compared with no protein in buffer. All the aptamers tested in the sandwich assay were 40 mers having a Kd≤1 nM. A total of 70 pairs showed signals of ≥50-fold. Three sandwich pairs were identified when each aptamer of the pair were selected from single modified libraries (3 sandwich aptamer pairs/3 single base modified libraries). In contrast, 22 sandwich pairs were identified when one aptamer of the pair was selected from three single base modified libraries and the other aptamer of the pairs was selected from four double base modified libraries (i.e., 22 sandwich aptamer pairs/3 single base modified libraries, and 4 double base modified libraries), and 45 sandwich pairs were identified when both aptamers of the pairs were selected from dual modified libraries (45 sandwich aptamer pairs/5 double base modified libraries). (C) Comparison of the number of sandwich pairs for the target protein PCSK9 derived from the capture aptamer library having a single base modified aptamer and the detection aptamer library having a single base modified aptamer; the capture aptamer library having a single base modified aptamer and the detection aptamer library having two base modified aptamer; and the capture aptamer library having two base modified aptamer and the detection aptamer library having two base modified aptamer.

SELEX method sometimes yields aptamers that preferentially bind to a dominant "aptagenic" epitopes on the target surface. Therefore, reports on aptamer sandwich pairs are limited in the literature. Modifications in the selection method may be employed to search for the aptamers that can bind to different epitopes on the target protein, such as multivalent aptamer isolation (MAI-SELEX), array-based discovery platform for multivalent aptamer (AD-MAP) sandwich selections, in which primary aptamer is used in excess to block the first epitope in an effort to discover second aptamer binding to a non-competing signaling epitope. To demonstrate if expanded chemical diversity generated by multiplicity in the modifications on dC and dU together in selecting aptamers that can bind to different epitopes on the target surface, bead-based sandwich pair screening assays were developed in which Luminex® MagPlex® avidin coupled magnetic beads were used to capture biotinylated primary aptamer (FIG. 7A). The capture beads with individual aptamers were used mixed together to search for second binding partner in a multiplex pair-wise combination (FIG. 7A). For this experiment, 40 mer aptamers (n=96, 9216 pairs) with affinity $K_d$≤1 nM from single and two base modified libraries were used. Briefly, individual aptamers (0.05 pmoles per sample) with were captured on single MagPlex Avidin bead type and mixed together (24 beads in one experiment, 1000 beads per sample) and captured for 20 min at room temperature with shaking at 1850 rpm. Beads were washed with 1× SBT for 2 min followed with 0.5 mM free biotin wash for 5 min in 1XSBT, followed by 3 washes of 1× SBT for 2 min each. Beads were blocked with free Streptavidin for 5 min and washed again for 2 min with 1× SBT. The 24 different bead types with individual aptamers were mixed together for screening of sandwich partner for each of the capture aptamer. A detection or secondary aptamer was diluted to 500 nM in 1XSBT, heat-cooled and mixed with PCSK9 (final 10 nM), incubated at 25° C. for 1 hr. 1000 capture beads were added and incubated further for 1 hr with shaking. Beads were then captured on a magnet, washed three times with 1× SBT for 2 min each and re-suspended in 75 μL 1× SBT with 0.1% BSA and 100 uM DxSO4. To this 75 μL of Streptavidin phycoerythrin (final 5 μg/mL) was added and incubated at 25° C. for 20 min with shaking. Beads were finally washed again for 2 min with 1× SBT and read on Luminex 3D xMAP machine.

Figure 7B:
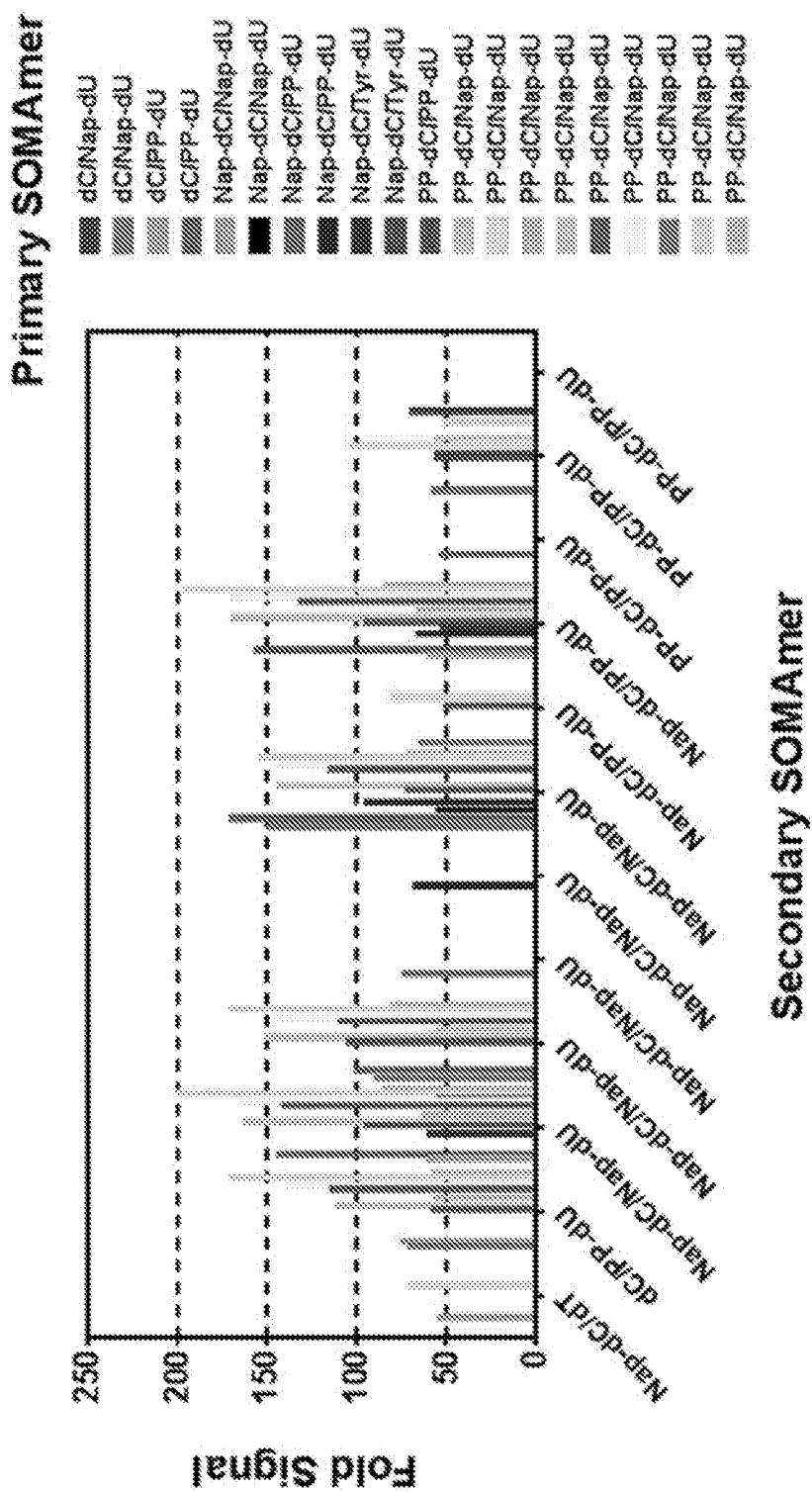

The single base modified libraries generated few sandwich pairs (three), while adding aptamers from two base modified libraries in combination with single base modified aptamers resulted in more sandwich pairs (22 pairs). Moreover, the number of sandwich pairs per library was dramatically increased when both partners (capture and detection) aptamers came from the two base modified libraries (45 pairs, FIG. 7C, FIG. 7B).

Figure 7C:
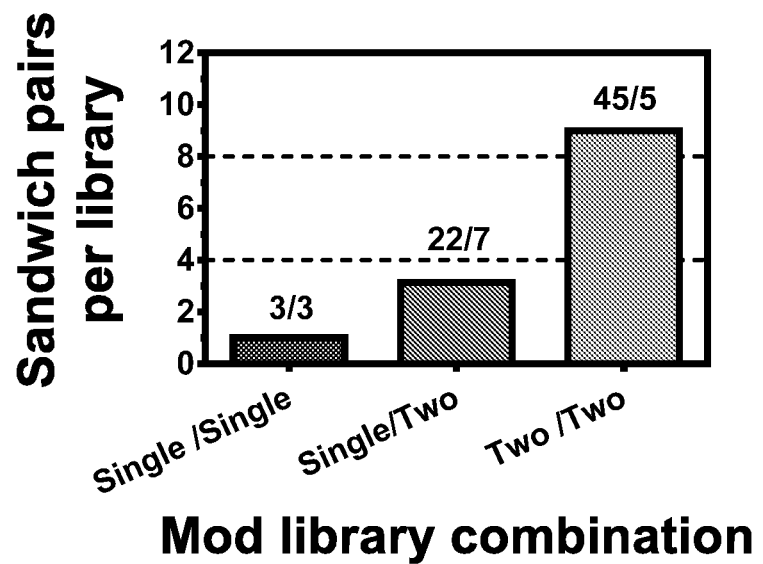
Figure 8A:
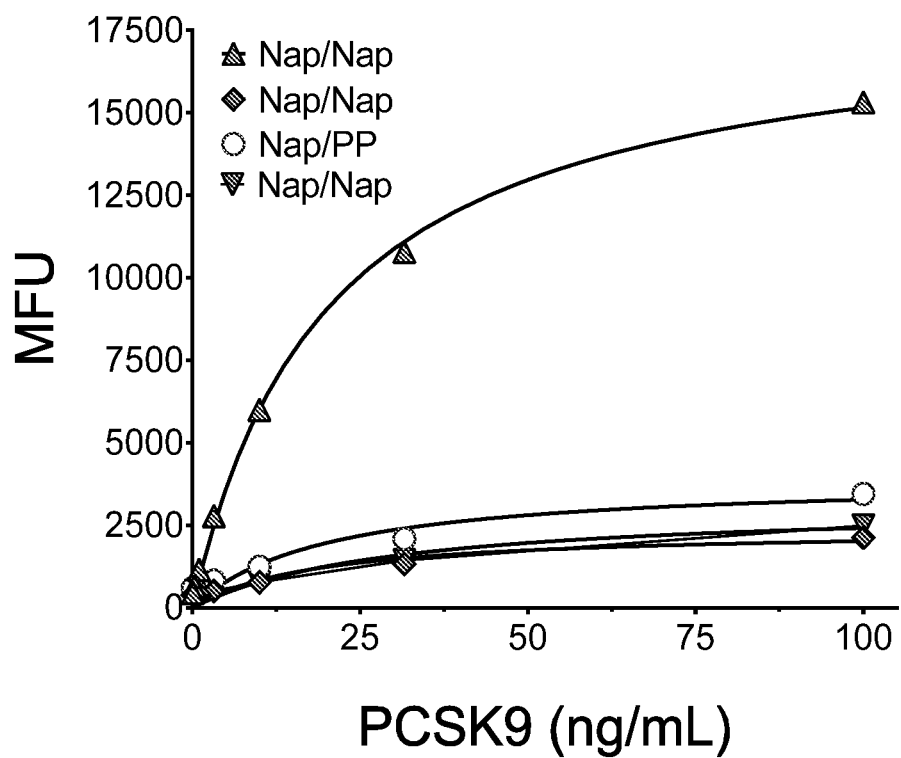
FIG. 8A-D. Sandwich pairs showing PCSK9 concentration dependent signals in bead-based Luminex® assays. (A) The concentration dependent signals were observed with best performing capture or primary aptamer paired with select secondary or detection aptamers. (B) The concentration dependent signals were observed with best performing secondary or detection aptamer with select primary or capture aptamers. (C) Lead sandwich pair, dC/PP-dU aptamer (primary) and Nap-dC/Nap-dU aptamer (secondary), showing signals when orientation of the aptamers is switched. (D) The standard curve obtained with recombinant wild type PCSK9 and the gain-of-function mutant PCSK9 D374Y. The linear concentration dependent signals were obtained with sandwich pair detecting wild-type PCSK9 (circles) and the gain-of-function mutant PCSK9 D374Y (triangles) protein.
Figure 8B:
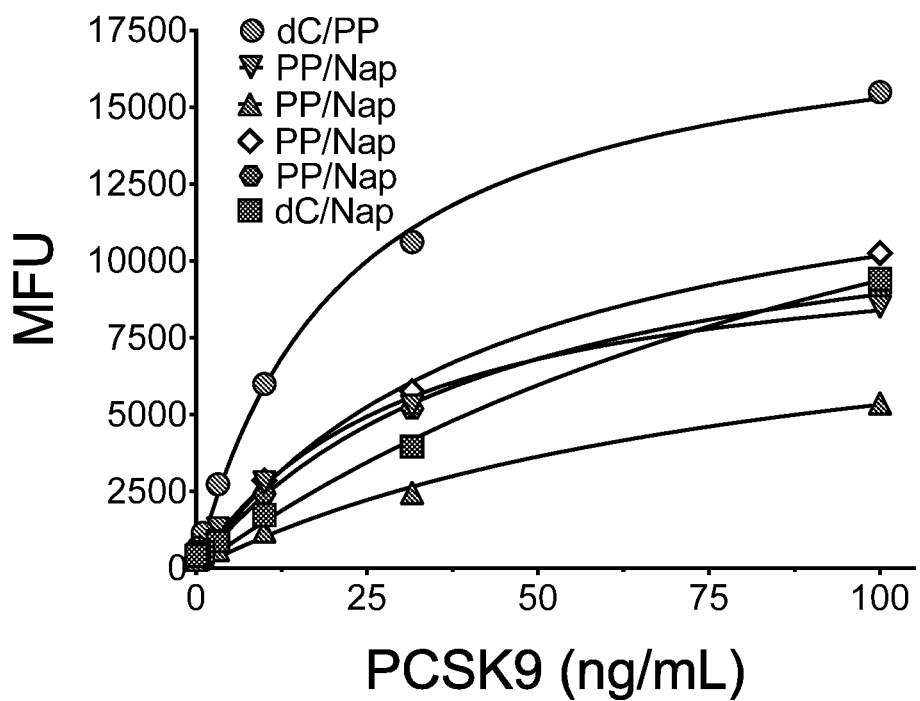
Figure 8C:
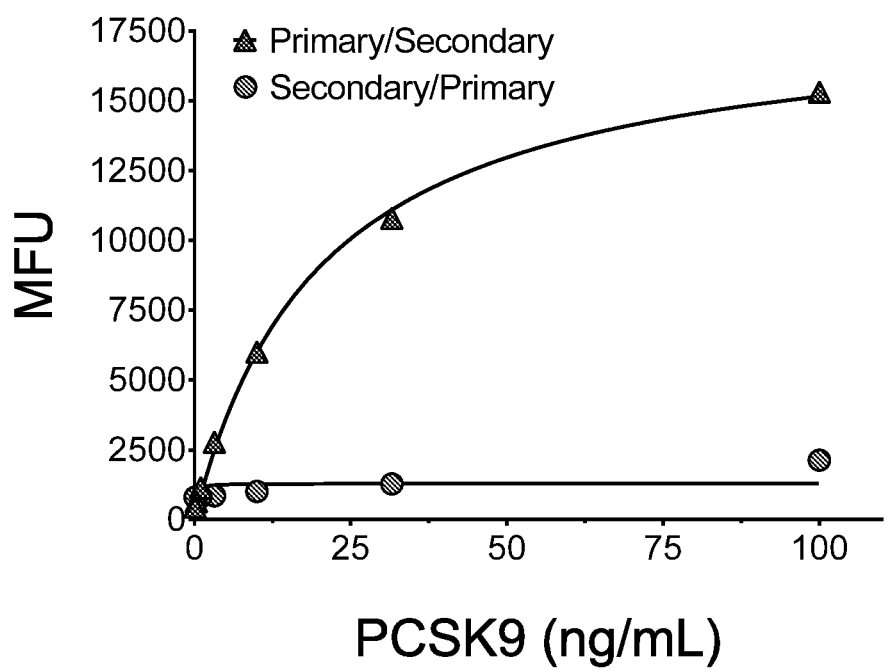
Figure 8D:
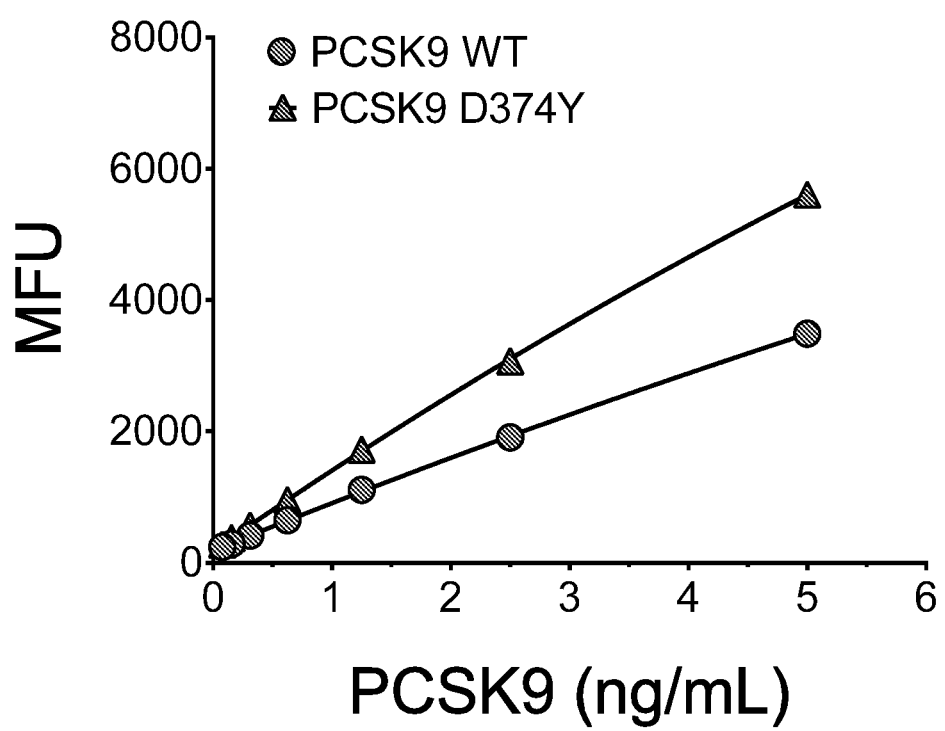

The multiple epitope binding results from the sandwich screening suggested that the increase in the chemical diversity in initial random library resulted in modified aptamers that can bind to non-competing sites on the target surface. Next, the sandwich pairs that resulted in highest signals (10 nM PCSK9 concentration; 0.75% of all pairs tested, 70 pairs out of 9216; FIG. 7C) were measured for PCSK9 concentration dependent responses with a subset of results shown in FIGS. 8A (the concentration dependent signals are shown for the single base modified primary aptamer dC/PP-dU and the best secondary that worked well was the two base modified aptamer Nap-dC/Nap-dU [triangles]) and 8B (the concentration dependent signals are shown for the two base modified secondary aptamer Nap-dC/Nap-dU and the best primary that worked well was the single base modified aptamer dC/PP-dU [closed squares]). Interestingly, one specific pair, constituting a single base modified primary (PP-dU, affinity, Kd of 175 pM) and a two base modified secondary (Nap-dU/Nap-dC, affinity, Kd of 531 pM), resulted in the robust signal that was much higher than any other pairs in one orientation (FIG. 8C). However, when this single base modified primary aptamer was switched to a secondary aptamer, signal was lost, which indicated that the orientation of the aptamers was important for this sandwich pair. This aptamer sandwich pair can also measure activity of a gain-of-function mutant protein, PCSK9 D374Y (FIG. 8D), which has higher affinity for LDL-R than wild type PCSK9 and is reported to be over-expressed in patients with severe form of familial hypercholesterolemia (FH). The sensitivity and MFU values were higher for the mutant PCSK9 D374Y than the wild type protein.

The specificity of an aptamer sandwich pair was also measured by lack of endogenous signal when recombinant human PCSK9 was spiked into newborn calf serum (NBCS) compared to human plasma (data not shown).

Figure 9A:
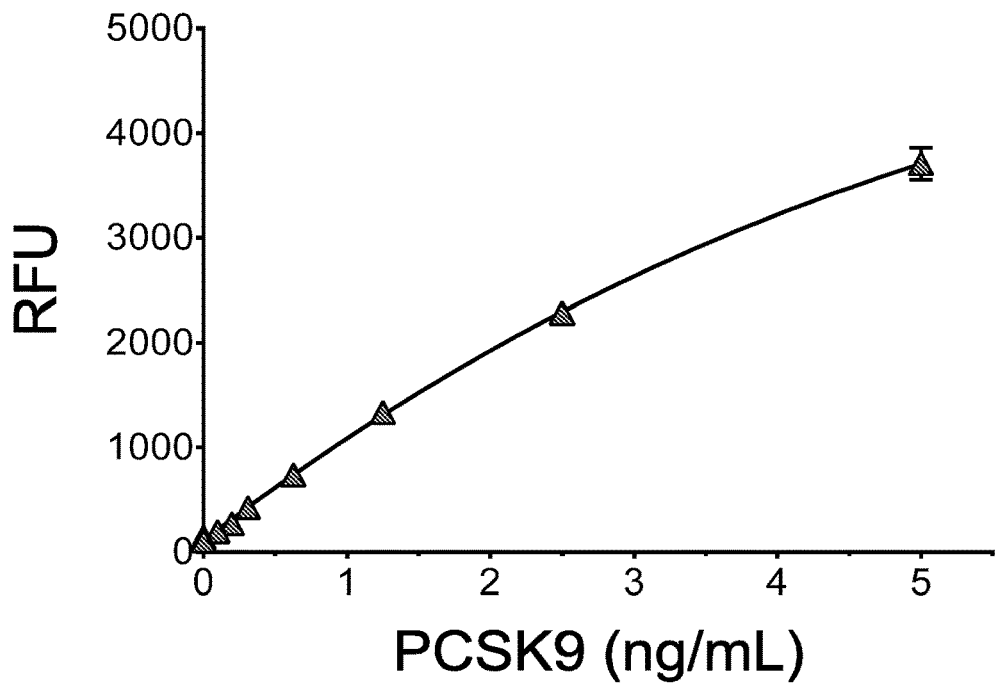
FIG. 9A-B. Sensitivity of sandwich assay: performance of aptamer sandwich assay (dC/PP-dU aptamer (primary) and Nap-dC/Nap-dU aptamer (secondary)) showing limits of detection of PCSK9 concentrations in buffer. (A) The linear concentration dependent signals were observed with aptamer sandwich assay with lower limit of quantification ~80 pg/mL (LLOQ) (B) The linear concentration dependent signals were observed with aptamer sandwich assay with upper limit of quantification ~10 ng/mL (ULOQ).
Figure 9B:
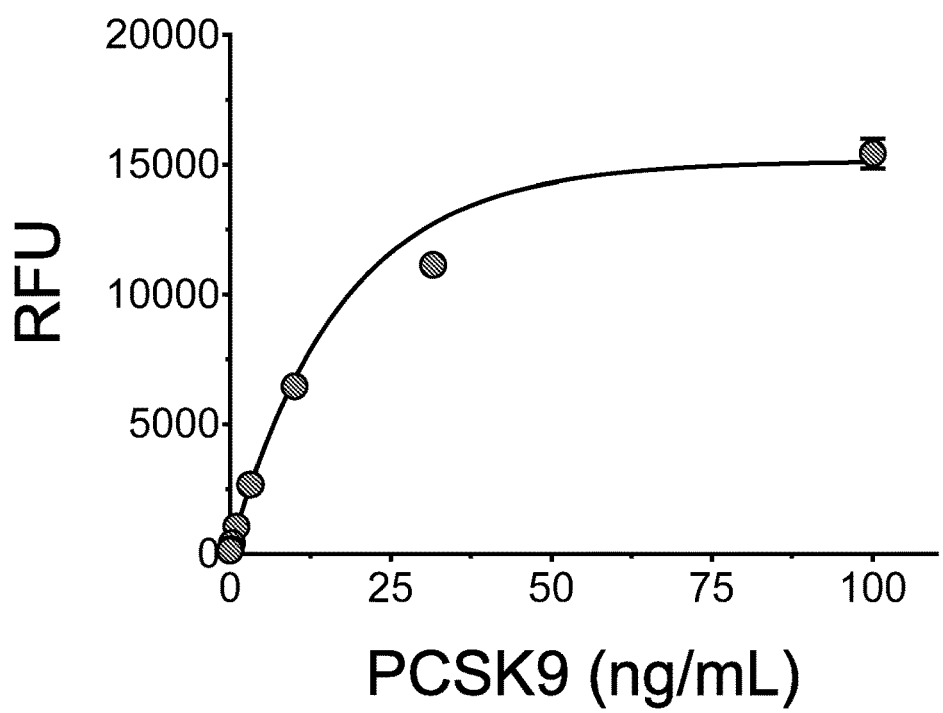
Figure 10:
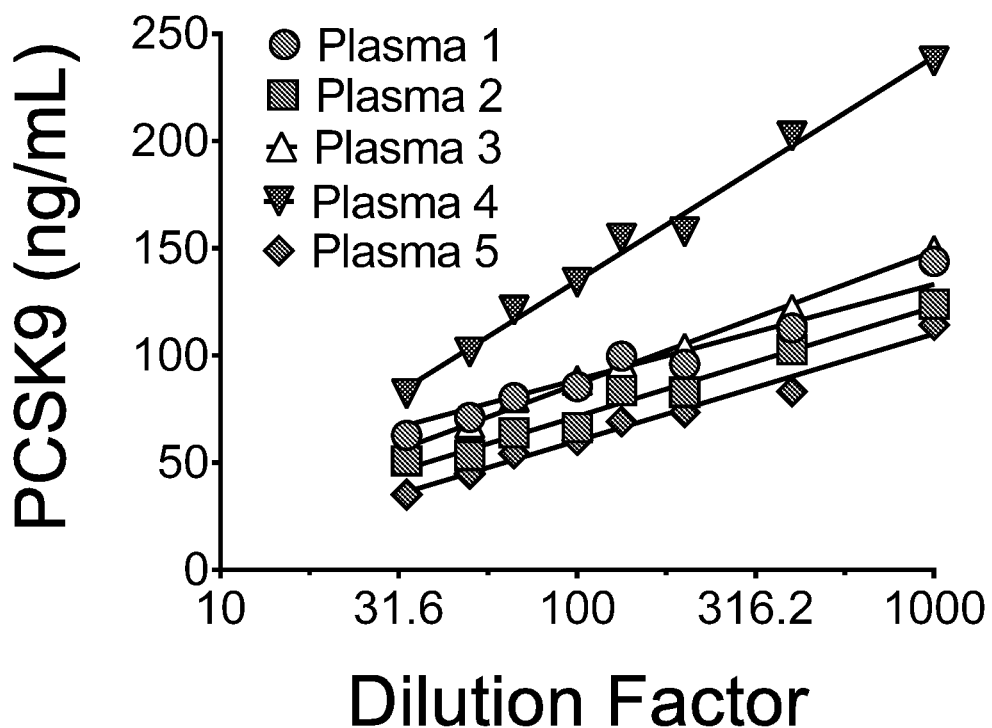
FIG. 10. Dilution linearity of the sandwich assay using dC/PP-dU aptamer (primary) and Nap-dC/Nap-dU aptamer (secondary).

This sandwich pair was further characterized to develop an aptamer sandwich assay to detect circulating concentrations of plasma PCSK9 in human clinical samples. The performance of the sandwich assay was evaluated by conducting studies such as sensitivity (FIG. 9A and 9B and Tables 5 and 6), precision (Tables 7 and 8), accuracy (Table 9) and plasma dilution linearity measurements (FIG. 10), all of which confirmed a robust assay window. To assess the sample dilution linearity of the assay, a sandwich assay was performed with samples containing and/or spiked with high concentrations of PCSK9. The plasma samples (n=5) were serially diluted with the assay buffer to fit the values within the dynamic range of the assay.

The limit of detection (LLoD), defined as the concentration of PCSK9 (40 pg/mL) giving an RFU value higher than the mean RFU of blank (dilution buffer) plus 3 standard deviations, is shown in Table 5. The lower limit of quantification (LLoQ) and upper limit of quantification (ULoQ), defined as lowest and highest concentrations of PCSK9 that can be quantitated using 4 parameter logistic (4PL) fit applied to the standard curves resulting in 80-120% recovery of the known target concentrations, are shown in Table 6. To determine intra-assay variability, five plasma samples of known concentrations were tested 16 times in single plate. See Table 7. Coefficients of variability (CVs) within the assay ranged from 4.3% to 6%. To determine inter-assay variability, five plasma samples of known concentrations were measured in five separate assays. See Table 8. CVs between the assays ranged from 2.3% to 9.8%. Finally, to determine the accuracy in target measurement, five plasma samples were spiked with different amounts of PCSK9 and measured. The recovery of spiked PCSK9 levels throughout the range of the assay was evaluated. See Table 9. The percent recovery of samples averaged from 83.1% to 137.5% of the spiked target.

A set of plasma samples obtained from two groups of individuals, one control group (n=42) and other study group in which subjects were on Lipitor® statin therapy (n=42, by self-report) was evaluated in order to determine if the assay can statistically differentiate between these two groups, because it is known that use of statins increases plasma concentrations of PCSK9. The sandwich assay was developed using a capture or primary SOMAmer (11723-5) as a single base modified aptamer (PP-dU/dC) and a secondary or detection aptamer (11727-20) as a two base modified aptamer (Nap-dC/Nap-dU).

Figure 11:
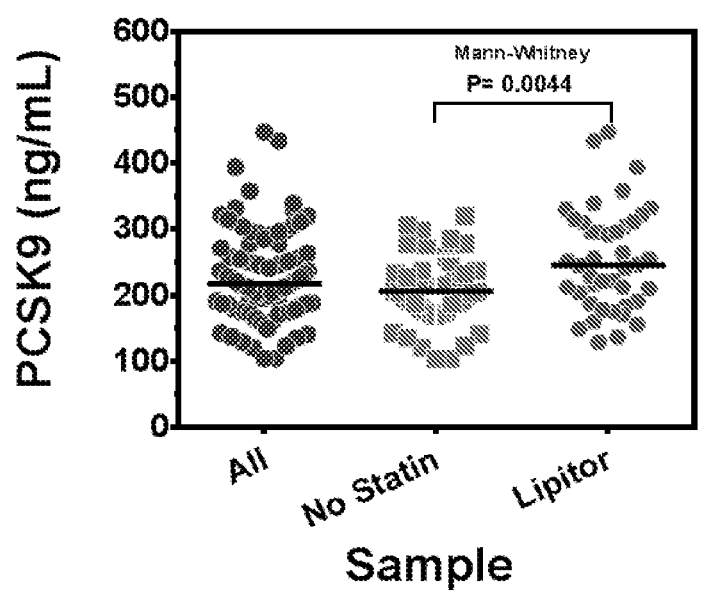
FIG. 11. The sandwich assay comprising primary single base modified aptamer and secondary two base modified aptamer (dC/PP-dU aptamer (primary) and Nap-dC/Nap-dU aptamer (secondary)).

These results indicated that aptamer sandwich assay can statistically differentiate between the two groups with P value of 0.0044 (FIG. 11) by Mann-Whitney analysis and that this assay could have use in identifying people who could benefit from anti-PCSK9 therapy due to their high plasma concentrations of PCSK9.

Figure 12:
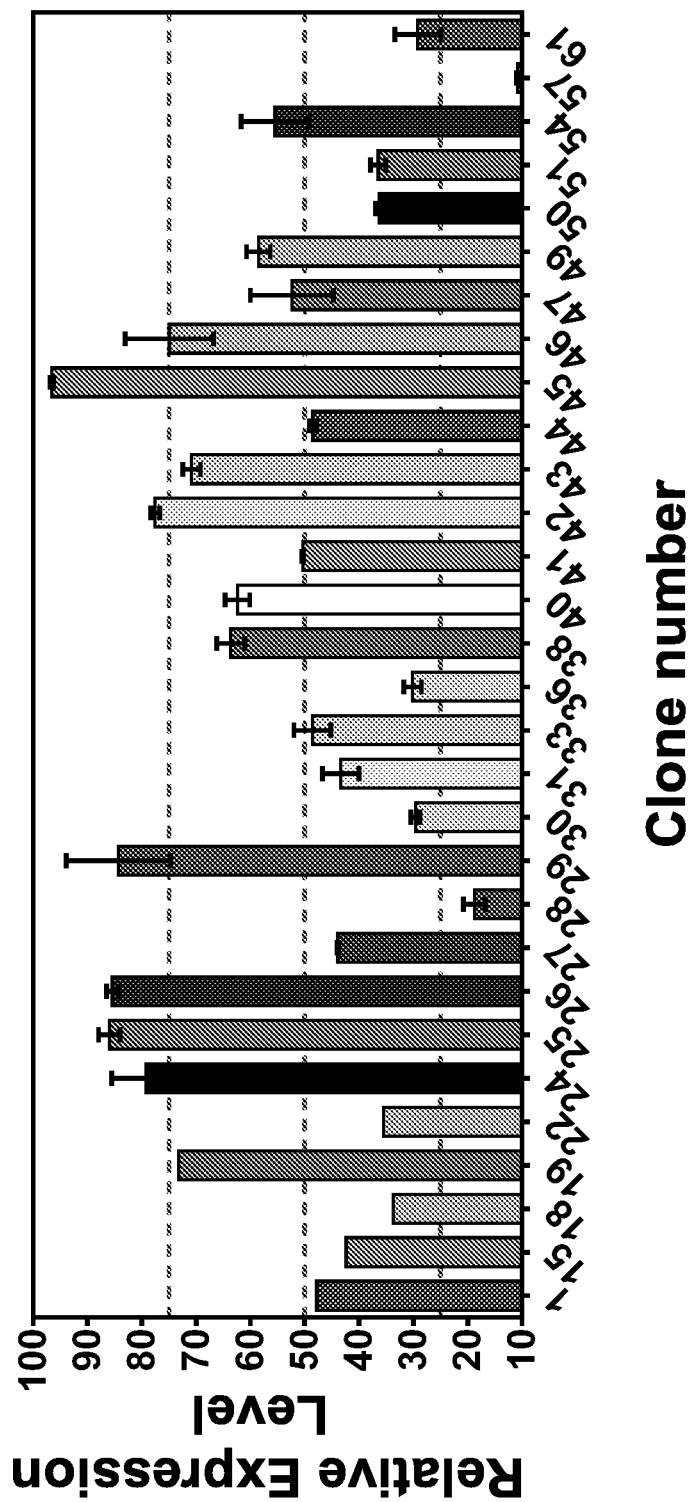
FIG. 12. Over expression of PCSK9 in wild-type HepG2 cells.

An aptamer sandwich assay was also used to measure PCSK9 concentrations in cell-free supernatants from PCSK9 over-expressing HepG2 cells to identify the over-expressing clones and to demonstrate the research utility of the assay (FIG. 12). PCSK9 was over-expressed in HepG2 cells using the SBI System Biosciences LentiViral system (LV300A-1). The HepG2 cell line was transduced with lentiviral expression clone for wild type human PCSK9 obtained from Origene (RC220000L1) for the generation of stable cell line. A total of 96 individual clones were screened for their ability to secrete PCSK9. The relative amount of PCSK9 secreted in the medium was measured by the aptamer sandwich assay for each clone and was compared with expression from wild-type HepG2 cells. The number of cells used to produce recombinant protein was normalized using the Cell Titer-Glo® Luminescent cell viability assay. Clone number 45 secreted ~100-fold more PCSK9 than wild-type HepG2 cells.

TABLE 5

Sensitivity of sandwich assay (lower limit of detection) LLoD Quantitation

| No. | Blank | PCSK9 (40 pg/mL) |
| --- | --- | --- |
| 1 | 127.5 | 175.5 |
| 2 | 124 | 175.5 |
| 3 | 122 | 179 |
| 4 | 129 | 181.5 |
| 5 | 136 | 189.5 |
| 6 | 125.5 | 185.5 |
| 7 | 117 | 174.5 |
| 8 | 127.5 | 170 |
| 9 | 115.5 | 173.5 |
| 10 | 121 | 179.5 |
| 11 | 128 | 166 |
| 12 | 120.5 | 181.5 |
| 13 | 120.5 | 181.5 |
| 14 | 130.5 | 170.5 |
| 15 | 115.5 | 172 |

TABLE 5-continued

Sensitivity of sandwich assay (lower limit of detection)
LLoD Quantitation

| No. | Blank | PCSK9 (40 pg/mL) |
|---|---|---|
| 16 | 130 | 164 |
| CV (%) | 4.73 | 3.93 |

TABLE 6

Sensitivity of sandwich assay (lower limit of quantification)

| | ULoQ Quantitation Logistic 4PL ($R^2$ = 0.99) | | LLoQ Quantitation Logistic 4PL ($R^2$ = 0.99) | |
|---|---|---|---|---|
| | PCSK9 (ng/mL) | % Std Recovery | PCSK9 (ng/mL) | % Std Recovery |
| Std 1 | 100 | Out of range | 5 | 100.1 |
| Std 2 | 31.6000 | 72.3 | 2.5 | 99.3 |
| Std 3 | 9.9856 | 94.5 | 1.25 | 102.6 |
| Std 4 | 3.1554 | 102.2 | 0.625 | 100.2 |
| Std 5 | 0.9971 | 112.1 | 0.3125 | 98.0 |
| Std 6 | 0.3151 | 108.9 | 0.156 | 98.8 |
| Std 7 | 0.0996 | 89.1 | 0.078 | 105.5 |
| Std 8 | 0.0315 | 54.6 | 0.039 | 79.9 |
| Std 9 | 0.0099 | Out of range | 0.020 | 82.6 |
| Std 10 | 0.0031 | Out of range | 0.010 | 67.2 |
| Std 11 | 0.0010 | Out of range | 0.005 | Out of range |

TABLE 7

Precision within assays
PCSK9 (ng/mL)

| No. | Plasma 1 | Plasma 2 | Plasma 3 | Plasma 4 | Plasma 5 |
|---|---|---|---|---|---|
| 1 | 139.4 | 118.8 | 196.1 | 220.8 | 104.4 |
| 2 | 149.4 | 120.7 | 164.4 | 208.5 | 84.7 |
| 3 | 142 | 115.9 | 186.4 | 224.9 | 102.3 |
| 4 | 151.4 | 125.8 | 196.7 | 227.1 | 102 |
| 5 | 147.7 | 125.6 | 193.9 | 226.3 | 96.7 |
| 6 | 146.6 | 125.3 | 183.2 | 235.2 | 98.5 |
| 7 | 148.4 | 123.7 | 179.4 | 237.8 | 100.9 |
| 8 | 133.8 | 127.6 | 172 | 245.1 | 94.3 |
| 9 | 154.7 | 130.2 | 191.3 | 240.3 | 100.3 |
| 10 | 147 | 117.5 | 181.7 | 228.3 | 104.2 |
| 11 | 133 | 121.3 | 190.6 | 229.5 | 89.3 |
| 12 | 150.9 | 127.9 | 189.8 | 231.3 | 98 |
| 13 | 146 | 121.1 | 193.2 | 218.5 | 91.4 |
| 14 | 152.9 | 125.8 | 195.2 | 232.5 | 100.5 |
| 15 | 126.8 | 117.7 | 173.1 | 220.4 | 88.2 |
| 16 | 153.6 | 109 | 172.9 | 235.6 | 93.8 |
| CV (%) | 5.4 | 4.3 | 5.3 | 3.9 | 6 |

TABLE 8

Precision between assays
PCSK9 (ng/mL)

| No. | Plasma 1 | Plasma 2 | Plasma 3 | Plasma 4 | Plasma 5 |
|---|---|---|---|---|---|
| Run 1 | 143.8 | 111.6 | 187.0 | 210.7 | 99.5 |
| Run 2 | 130.2 | 99.6 | 176.7 | 199.3 | 93.0 |
| Run 3 | 117.3 | 106.2 | 164.4 | 200.8 | 83.2 |
| Run 4 | 141.7 | 111.8 | 192.2 | 206.1 | 90.7 |
| Run 5 | 151.5 | 112.6 | 197.1 | 206.9 | 91.8 |
| CV (%) | 9.8 | 5.1 | 7.1 | 2.3 | 6.4 |

TABLE 9

Accuracy of target measurement

| Sample | | None (unspiked) | +300 (ng/mL) | +100 (ng/mL) | +30 (ng/mL) |
|---|---|---|---|---|---|
| Plasma 1 | PCSK9 (ng/mL) | 92.4 | 359.0 | 192.2 | 133.7 |
| | Recovery (%) | — | 88.9 | 99.8 | 137.5 |
| Plasma 2 | PCSK9 (ng/mL) | 76.9 | 351.7 | 179.8 | 109.2 |
| | Recovery (%) | — | 91.6 | 102.9 | 107.6 |
| Plasma 3 | PCSK9 (ng/mL) | 137.4 | 454.5 | 256.9 | 172.9 |
| | Recovery (%) | — | 105.7 | 119.5 | 118.3 |
| Plasma 4 | PCSK9 (ng/mL) | 172.0 | 474.8 | 275.5 | 202.3 |
| | Recovery (%) | — | 100.9 | 103.5 | 101.1 |
| Plasma 5 | PCSK9 (ng/mL) | 70.1 | 334.5 | 190.6 | 95.0 |
| | Recovery (%) | — | 88.1 | 120.5 | 83.1 |

Example 4

Target Activity Inhibition by Dual-Modified Aptamers

Figure 13:
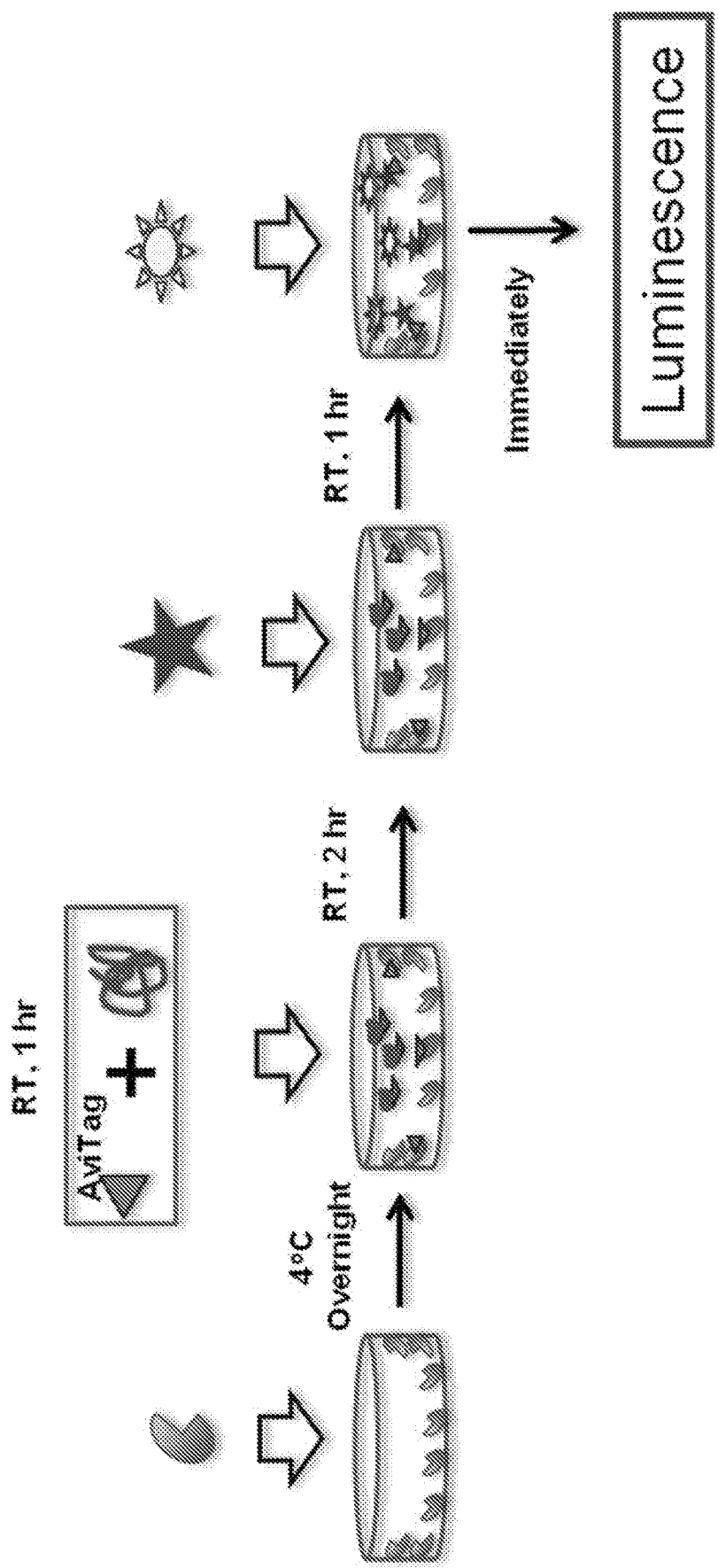
FIG. 13. Plate-based in vitro PCSK9 inhibition assays: schematics of inhibition of PCSK9 with aptamers.

To find inhibitors of PCSK9 that block binding of PCSK9 to LDL-R, 41 truncated 30 mer aptamers with $K_d \leq 1$ nM were screened in a plate-based assay in which plates were coated with LDL-R and binding of biotinylated PCSK9 was detected using streptavidin-HRP conjugate by chemiluminescent reagents (FIG. 13). The recombinant LDL-R (Acro Biosystems) was coated on the ELISA plates (2.5 µg/mL) overnight at 4° C., and then wells were washed and blocked with Super Block (Invitrogen) for 1 hr at room temperature. The biotinylated PCSK9 (Acro Biosystems, Avi-tagged) and aptamer were mixed together and incubated at room temperature for 1 hr, then added to the ELISA plate and further incubated for 2 hrs at room temperature with shaking. The top PCSK9 concentration was 0.5 nM and the top concentration for aptamer was 100 nM, and these were then serially diluted by ½ log for the inhibition curve. Streptavidin conjugated HRP (Invitrogen, 1 µg/ml) was added to the wells and incubated for 30 min at room temperature with shaking, Pico-sensitive chemiluminescence substrates (Invitrogen) were added, luminescence was measured in Luminometer (Hidex Plate Chameleon), and data were plotted in Graph Pad Prism 6.0 software to calculate the $EC_{50}$ values. A PCSK9 neutralizing antibody (BPS Bioscience) was used as the control.

Figure 14:
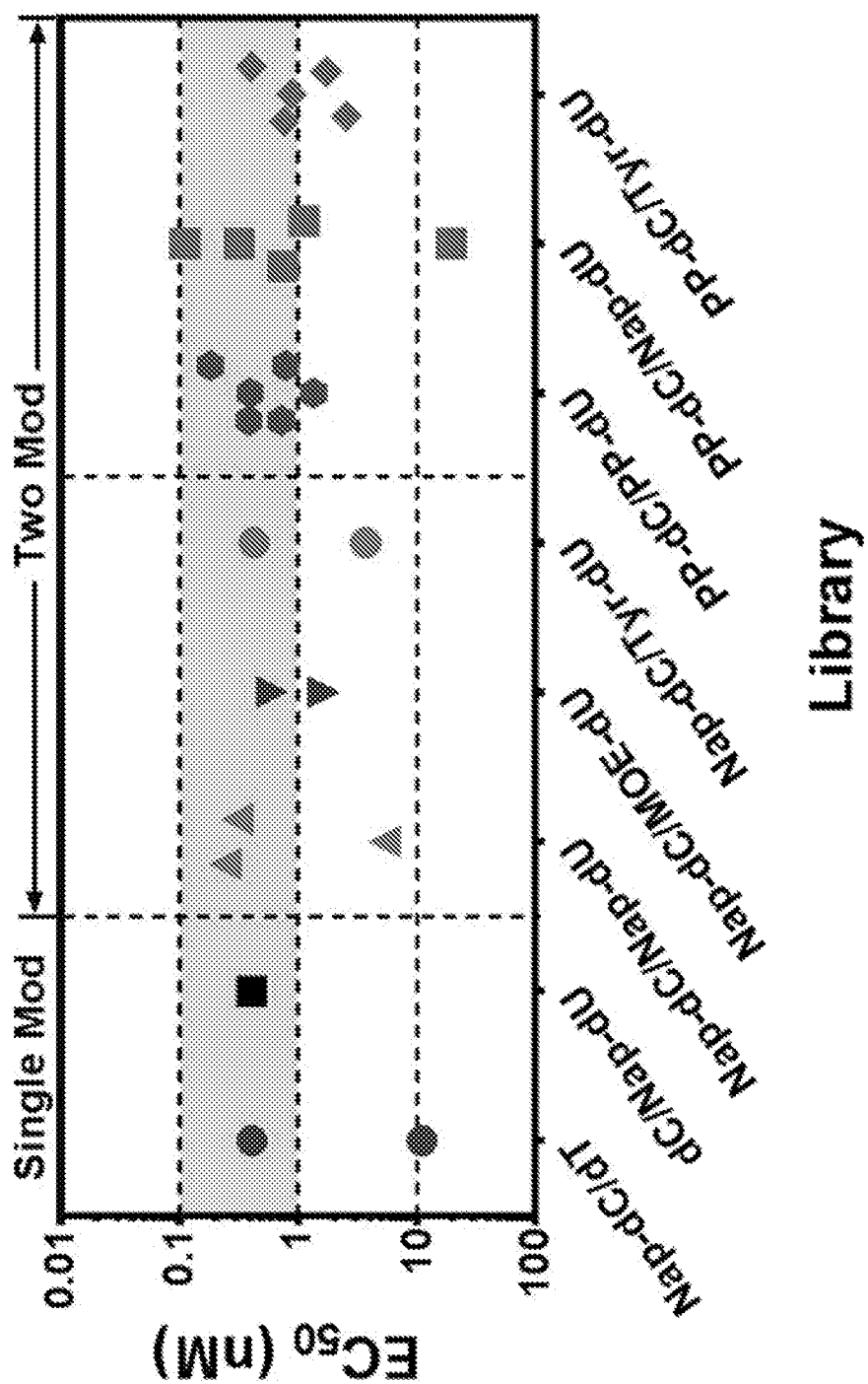
FIG. 14. Inhibition screen for single base or two base modified aptamers.
Figure 15A:
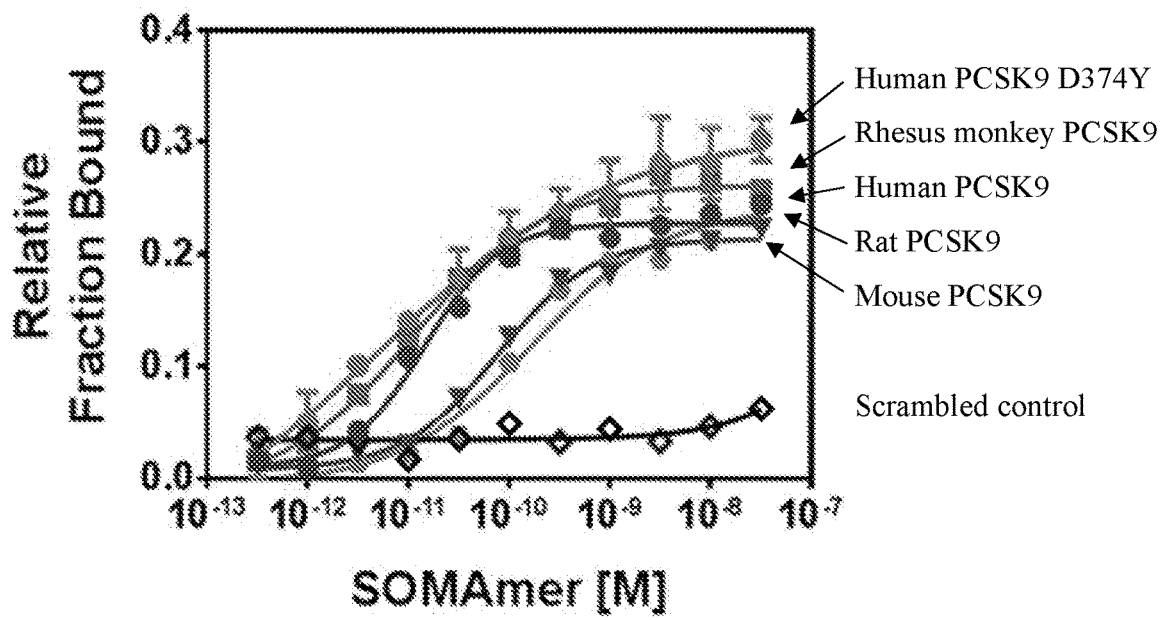
FIG. 15A-B. Species cross-reactive potential therapeutic two base modified aptamers. (A) The 30 mer two base modified (PP-dC/Nap-dU) rodent cross-reactive aptamer (11733-44, SEQ ID No: 44) affinities to human PCSK9 (filled blue circle), human gain-of-function mutant PCSK9 D374Y (filled red circle), Rhesus monkey PCSK9 (filled green square), rat PCSK9 (filled pink hexagon), mouse PCSK9 (filled inverted triangle) and scrambled control aptamer (open black diamond). (B) Species cross-reactive potential therapeutic two base modified aptamer showing inhibition of PCSK9 interaction with LDL-R. aptamer potently inhibiting PCSK9 interaction with LDL-R at $EC_{50}$ value of 2.1 nM (blue filled circle) and PCSK9 D374Y at $EC_{50}$ value of 3.6 nM (red filled triangle) and the scrambled control aptamer showing no inhibition of wild type PCSK9 (green filled squares) and gain-of-function mutant PCSK9 D374Y (open black squares).
Figure 15B:
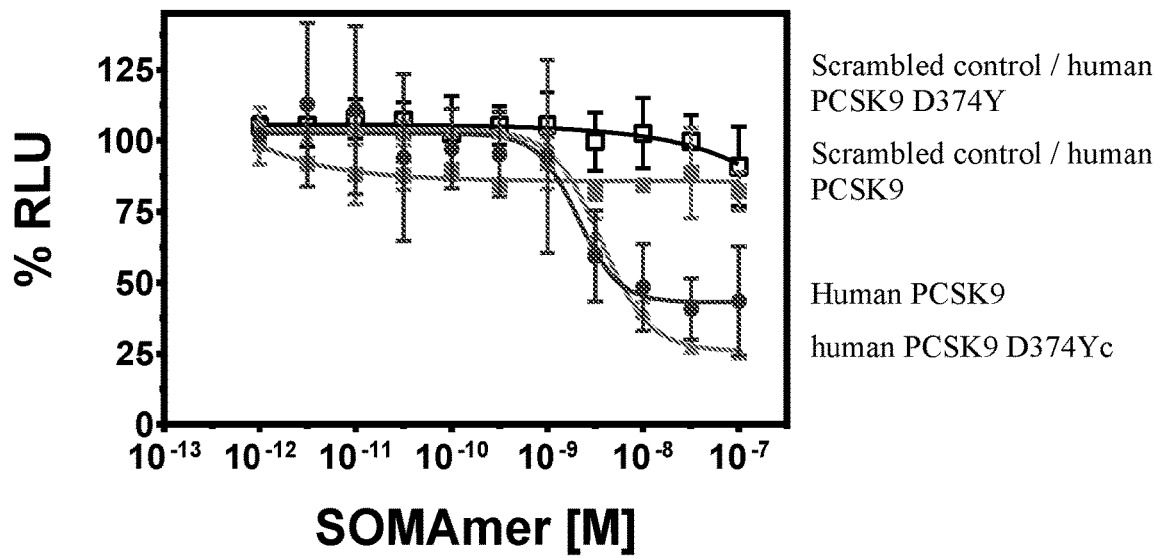

The results from the inhibition assay (testing concentrations of aptamers at 100 nM and PCSK9 at 1 nM) showed that 70% of the aptamers were inhibitors (over 90% inhibition) and that some of the two modified aptamers potently inhibited PCSK9 interactions with LDL-R (data not shown). Aptamers were further evaluated for dose-response curves to determine their EC50 values for inhibition. The results indicated that many of inhibitors potently inhibited the PCSK9 interaction with LDL-R with an $EC_{50}$ in the 0.1-1 nM range (FIG. 14). To demonstrate potential therapeutic value in two modified aptamers, one species cross-reactive PCSK9 aptamer (30 mer, Seq ID. 11733-91_5 (11733-198)) was chosen for measurement of target affinity to PCSK9's from various species. This aptamer had affinity of 14.7, 11.3, 5.2, 77 and 165 pM to human (wild-type), rhesus monkey, human (GOF mutant D374Y), mouse, and rat PCSK9, respectively (FIG. 15A). This aptamer also blocked the wild-type human PCSK9 LDL-R interaction with an $EC_{50}$ of 2.1 nM and the GOF mutant PCSK9 D374Y LDL-R interaction with an $EC_{50}$ of 3.6 nM (FIG. 15B). The specificity of this aptamer for PCSK9 compared with other PCs was evaluated, and results showed that this aptamer bound to only PCSK9 and not to other PCs (data not shown).

Figure 16:
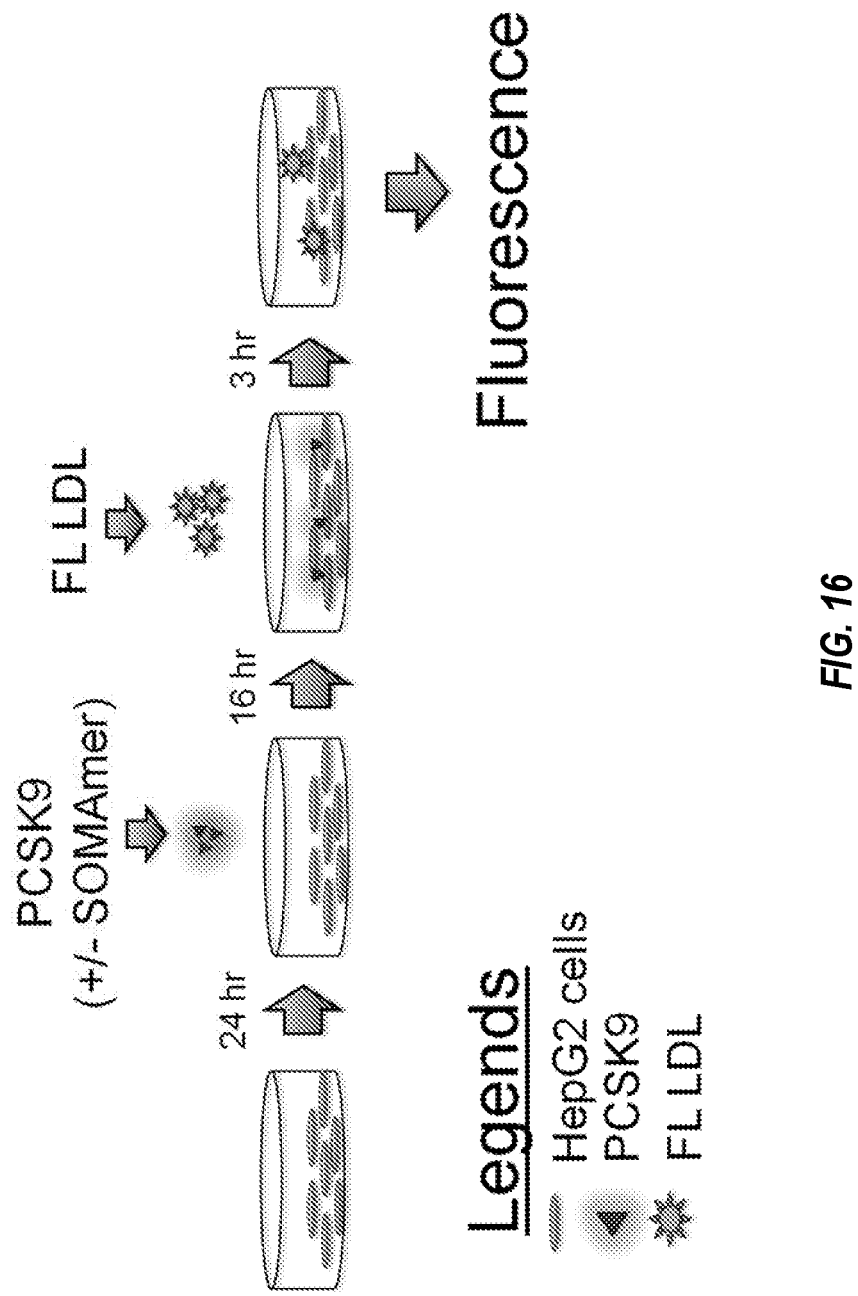
FIG. 16. Schematics of LDL-uptake reversal assay.
Figure 17:
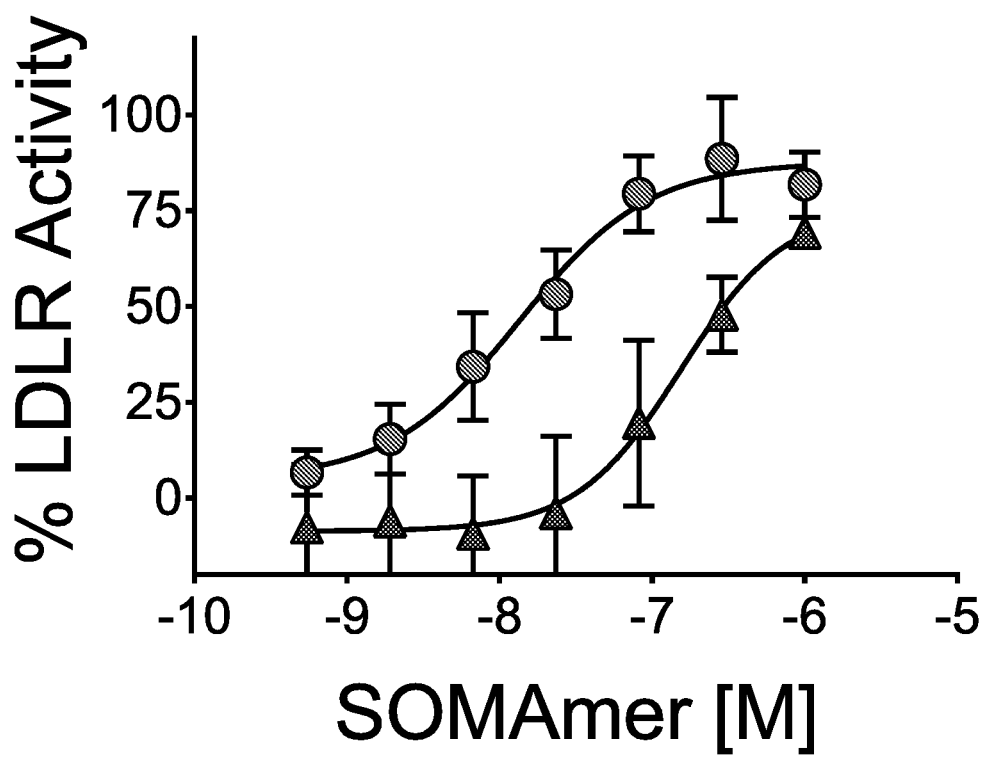
FIG. 17. Species cross-reactive PP-dC/Nap-DU aptamer inhibited LDL-R degradation by blocking PCSK9 interaction with LDL-R and increases LDL-R levels on the surface of HepG2 cells. The $EC_{50}$ value for the LDL-uptake reversal is 13.5 nM by active SOMAmer (red circle) which was not observed with scrambled control of the same sequence (blue triangle).

To test the neutralizing effect of the PCSK9 aptamer in blocking LDLR degradation, a PP-dC/Nap-dU aptamer was tested in an LDL uptake reversal assay in which wild-type HepG2 cells were incubated for 16 hrs with recombinant PCSK9, and then cells were washed and fluorescently-labeled LDL was added for 3 hrs. The results showed that the aptamer can reverse LDL-uptake with an $EC_{50}$ of 159 nM (FIG. 16 and FIG. 17). Further, aptamer treatment can increase the LDL-R levels in PCSK9 over-expressing HepG2 cells as measured by FACS (FIG. 17. These results with a species cross-reactive, high-affinity, truncated, specific and highly potent aptamer suggest that the potential therapeutic value of a two base modified aptamer could be further optimized for length and bio-stability by post-SELEX modification.

Example 5

Serum Stability of Dual-Modified Aptamers

To determine the serum-stability of the dual-modified aptamers in human serum, 1 µM gel-purified aptamer was incubated in 90% pooled human serum in PBS buffer in a total volume of 200 µL at 37° C. At various time points, 20 µL aliquots were collected and an equal volume of EDTA/formamide/dye mix (Formamide 87.7%, SDS, 0.03%, Sodium EDTA, 20 mM, Xylene Cyanol, 0.05%, Bromophenol Blue, 0.05%, Orange G, 0.1%) was added. The aliquot mixes were then stored at −20° C. Prior to analysis, the 40 µL aliquot mix was diluted with 100 µL H₂O and extracted with 150 µL 25:24:1 phenol:chloroform:isoamyl alcohol. The samples were centrifuged and 16,100 xg for 15 minutes, and the aptamer-containing aqueous phase was removed and stored at −20° C. until gel analysis.

The aptamer samples were loaded on a 15% TBE PAGE denaturing gel (8 M urea), and the aptamer stained with 1× (~2 µM) SYBR Gold for 10 minutes. The amount of full-length aptamer at each time point was quantified using FluorChemQ analysis software (Alphalnnotech).

Figure 18:
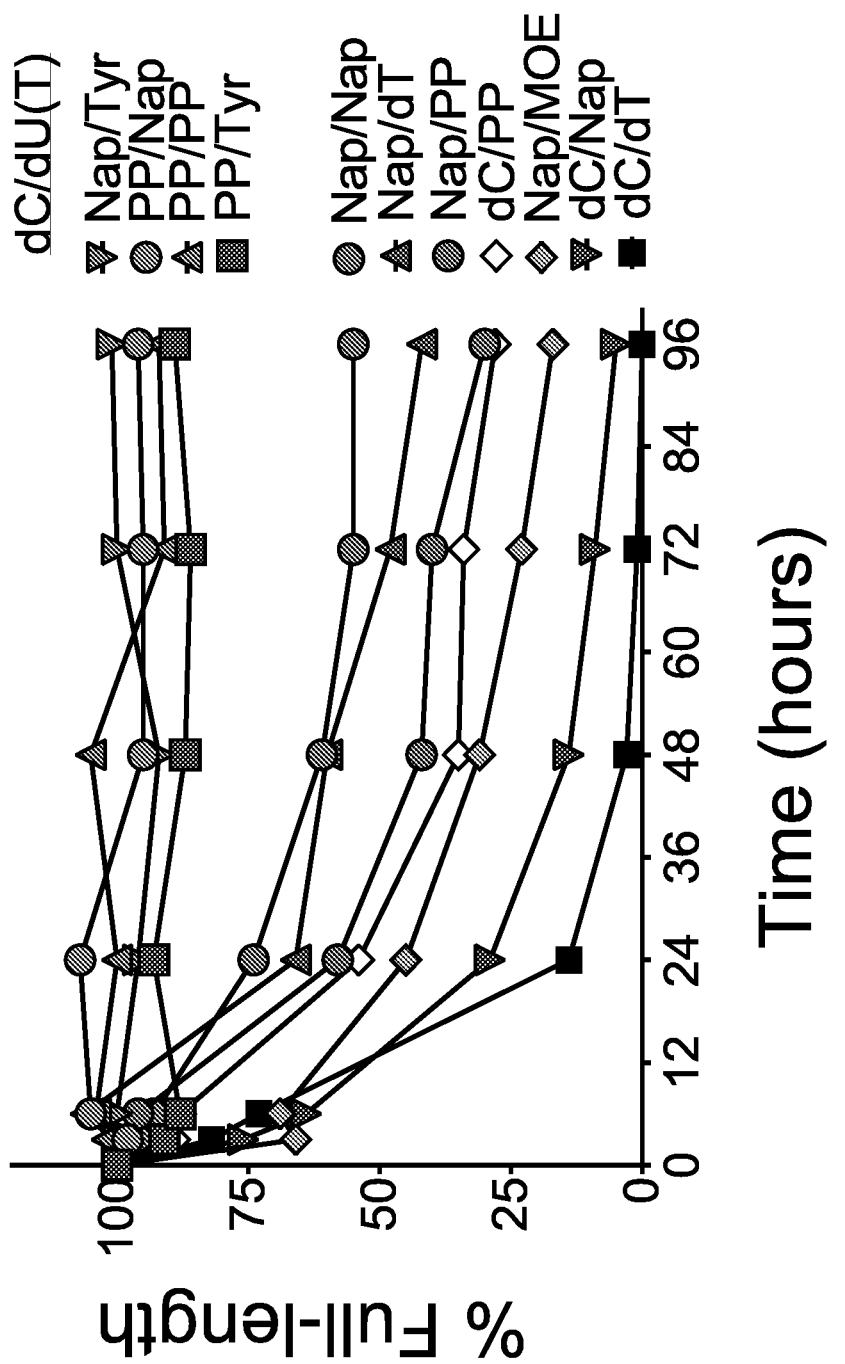
FIG. 18. Stability of single modified and dual modified aptamers in 90% human serum over time. The modification pattern of single C-5 modified or dual C-5 modified aptamers is provided with the figure legend (e.g., X/Y where X represents a dC (non-modified nucleotide), NapdC (Nap), or PPdC (PP); and Y represents a dU or dT (non-modified nucleotide, TyrdU (Tyr), NapdU (Nap), PPdU (PP) or MOEdU (MOE)).

The results of that experiment are shown in Table 10 and FIG. 18. Table 10 shows the composition of the aptamers tested in that experiment, the percentage of full-length aptamer remaining after 96 hours in 90% human serum and the half-life of each aptamer, which was calculated by linear regression fit using gel quantified data in GraphPad Prism 7 software. FIG. 18 shows the percentage of full-length aptamer remaining over time. In general, dual modified aptamers demonstrated greater stability in human serum over time than the single modified aptamers.

TABLE 10

Aptamer composition.

| Aptamer | length | dC mod | dU mod | #dC mod (%) | #dU mod (%) | #A (% A) | #C (% C) | #G (% G) | #T (% T) | % FL at 96 hours | Half-Life (hours) |
|---|---|---|---|---|---|---|---|---|---|---|---|
| dC/dT | 29 | none | none | none | none | 7 (24%) | 4 (14%) | 8 (28%) | 10 (34%) | 0 | 11 |
| NapdC/dT | 30 | Nap-dC | none | 12 (40%) | none | 4 (13.3%) | none | 9 (30%) | 5 (16.7%) | 39 | 72 |
| dC/NapdU | 30 | none | Nap-dU | none | 5 (16.7%) | 10 (33.3%) | 6 (20.0%) | 9 (30%) | none | 17 | 23 |
| dC/PPdU | 30 | none | PP-dU | none | 11 (36.7%) | 7 (23.3%) | 6 (20.0%) | 6 (20.0%) | none | 57 | 53 |
| NapdC/NapdU | 30 | Nap-dC | Nap-dU | 5 (16.7%) | 4 (13.3%) | 9 (30%) | none | 12 (40%) | none | 65 | 101 |
| NapdC/PPdU | 30 | Nap-dC | PP-dU | 7 (23.3%) | 8 (26.7%) | 5 (16.7%) | none | 10 (33.3%) | none | 44 | 53 |
| NapdC/MOEdU | 30 | Nap-dC | MOE-dU | 12 (40%) | 3 (10.0%) | 6 (20.0%) | none | 9 (30%) | none | 40 | 43 |
| NapdC/TyrdU | 30 | Nap-dC | Tyr-dU | 11 (36.7%) | 6 (20.0%) | 3 (10.0%) | none | 10 (33.3%) | none | 104 | 690 |
| PPdC/PPdU | 30 | PP-dC | PP-dU | 7 (23.3%) | 8 (26.7%) | 6 (20.0%) | none | 9 (30%) | none | 108 | 633 |
| PPdC/NapdU | 30 | PP-dC | Nap-dU | 7 (23.3%) | 9 (30%) | 6 (20.0%) | none | 8 (26.7%) | none | 86 | 847 |
| PPdC/TyrdU | 30 | PP-dC | Tyr-dU | 6 (20.0%) | 12 (40%) | 7 (23.3%) | none | 5 (16.7%) | none | 75 | 907 |

Example 6

Aptamers Comprising Two Modified Bases

The libraries described in Example 1 were used to select aptamers that bind to ErbB2, ErbB3, and PSMA. The selections were carried out for each target substantially as described in Example 1. For ErbB2 and ErbB3, the single-modified Nap-dC/dT; PP-dC/dT; and dC/Tyr-dU libraries; and the dual-modified Nap-dC/Tyr-dU, and PP-dC/ Tyr-dU libraries were used. For PSMA, the unmodified dC/dT library; the single-modified Nap-dC/dT; PP-dC/dT; dC/Nap-dU, dC-PP-dU, dC-MOE-dU, and dC/Tyr-dU libraries; and the dual-modified Nap-dC/Nap-dU, Nap-dC/PP-dU, Nap-dC/MOE-dU, Nap-dC/Tyr-dU, PP-dC/ PP-dU, PP-dC/Nap-dU, and PP-dC/Tyr-dU libraries were used.

Figure 19A:
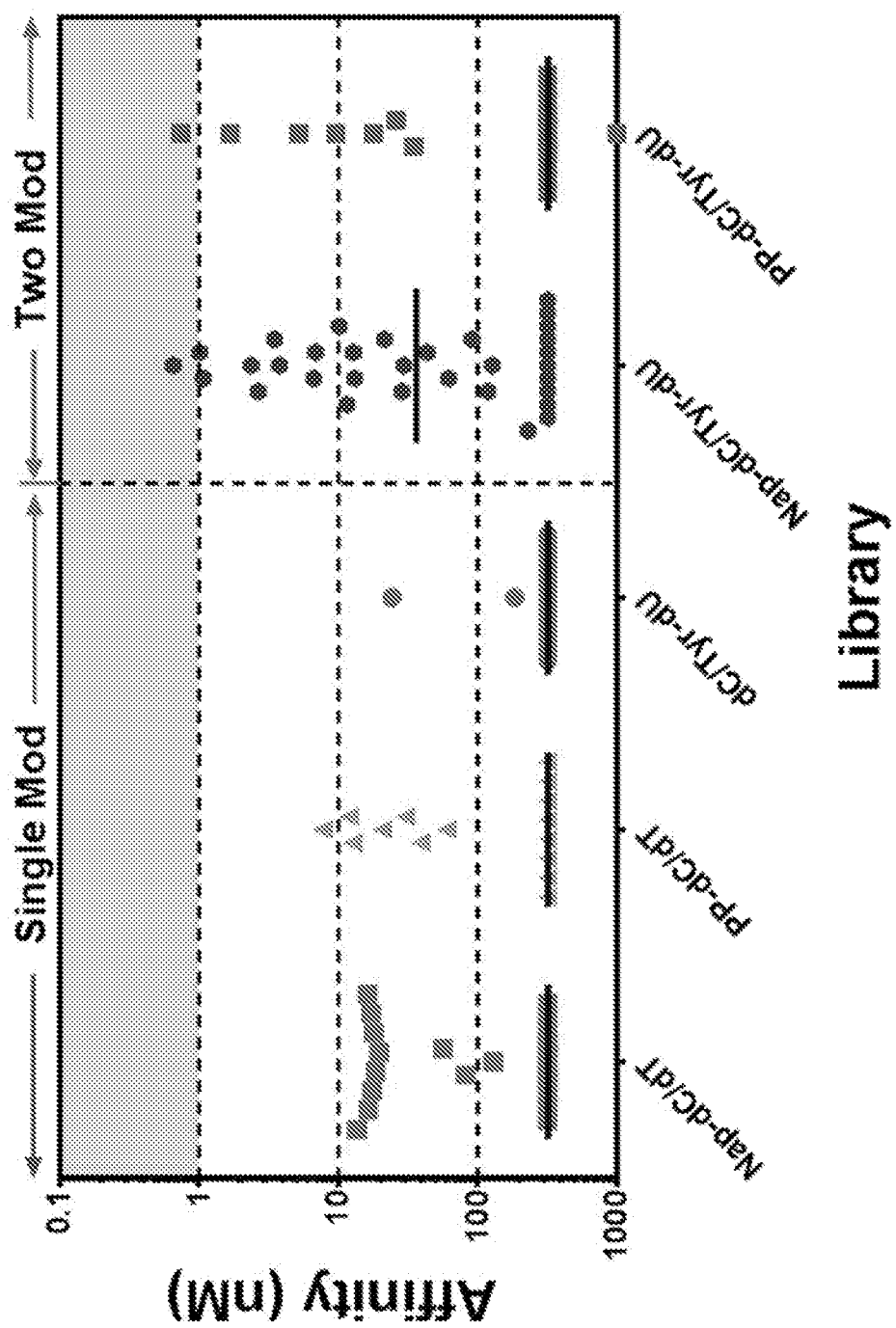
FIG. 19A-C. Binding affinities of 40 mer (30N+5+5) aptamers to ErbB2 (A), ErbB3 (B), and PSMA (C) generated using various modified libraries. Aptamers with affinities ≥1 nM are highlighted in gray shade and aptamers shown at 320 nM affinity represent no detectable binding at 32 nM top concentration on binding curve. Black line on each of the library indicates median value for the all aptamers in that library.
Figure 19B:
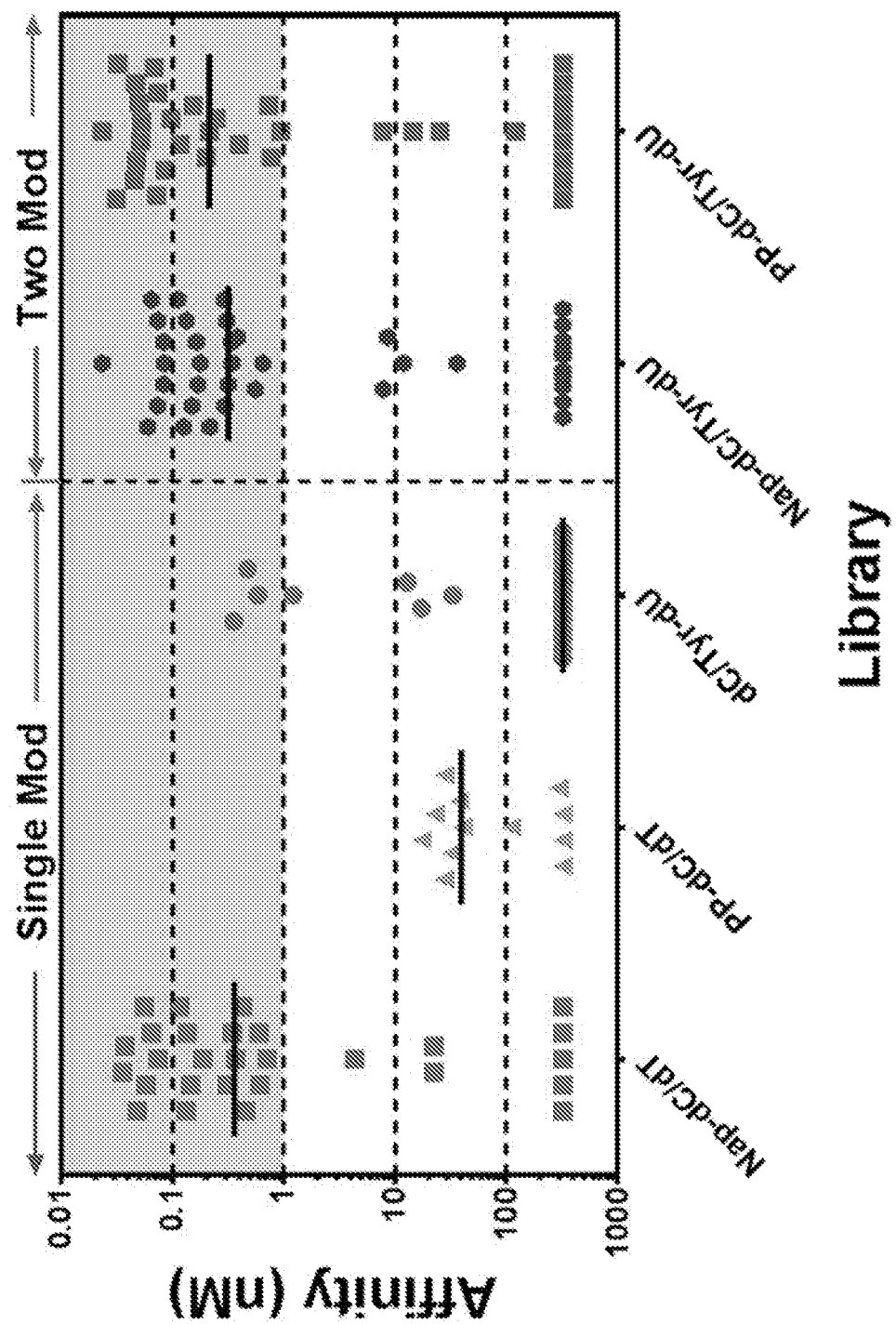
Figure 19C:
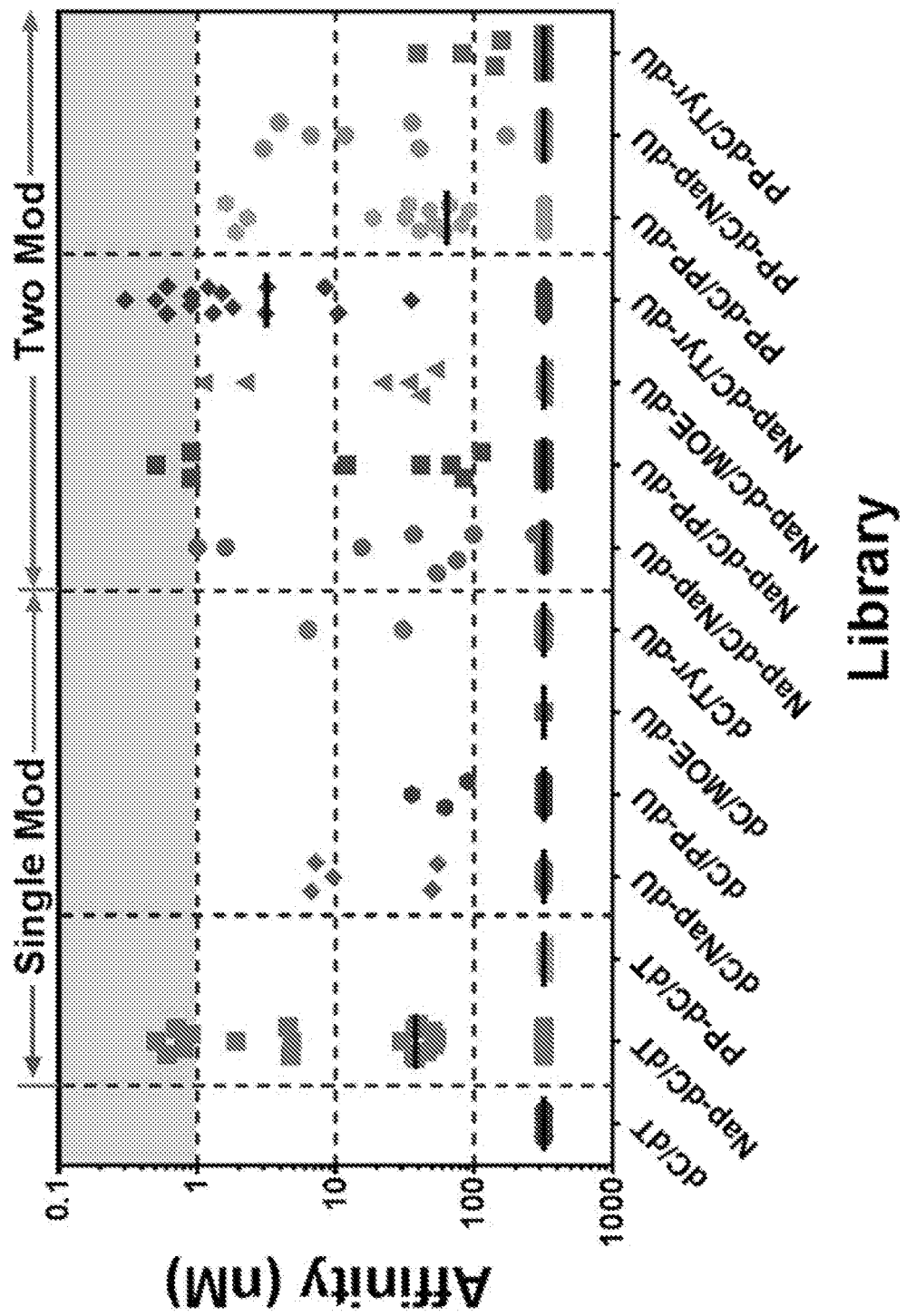

As before, the unmodified control DNA library (dC/dT), which was used for PSMA, did not result in any aptamers that bound to PSMA. The single modified libraries, with Nap modification (naphthyl moiety) either on dC or dU resulted in binders for all three targets, however, the dual-modified libraries provided aptamers with greater affinity relative to the single-modified libraries (FIG. 19A-C).

A summary of the data comparing the single modified aptamers (40-mers) and dual-modified aptamers (40-mers) for each of PSMA, ErbB2 and ErbB3 are shown in tables 11, 12 and 13 respectively.

TABLE 11

Binding Data Summary for Single and Dual Modified Aptamers for PSMA
PSMA Target

| Category | 5-Position Modification Of Aptamer | % of Aptamers Tested with a Kd ≤ 10 nM | Total # of Aptamers Tested | Kd for Aptamer with Greatest Affinity for Target | Total # of Aptamers with no Binding | % of Aptamers with no Binding |
|---|---|---|---|---|---|---|
| Control (unmodified) | dC/dT | 0% | 6 | N/A | 6 | 100% |
| Single Mod. | NapdC/dT | 36% | 25 | 0.5 nM | 7 | 28% |
| | PPdC/dT | 0% | 7 | N/A | 7 | 100% |
| | dC/NapdU | 13% | 24 | 6.7 nM | 19 | 79% |
| | dC/PPdU | 0% | 20 | 35.5 nM | 17 | 85% |
| | dC/MOEdU | 0% | 1 | N/A | 1 | 100% |
| | dC/TyrdU | 5% | 21 | 6.3 nM | 19 | 90% |
| | dC/ThrdU | N.T. | N.T. | N.T. | N.T. | N.T. |
| Two Mod. | NapdC/NapdU | 12% | 17 | 1 nM | 9 | 53% |
| | NapdC/PPdU | 12% | 17 | 0.5 nM | 9 | 53% |
| | NapdC/MOEdU | 15% | 13 | 1.1 nM | 7 | 54% |
| | NapdC/TyrdU | 58% | 26 | 0.3 nM | 9 | 35% |
| | NapdC/ThrdU | N.T. | N.T. | N.T. | N.T. | N.T. |
| | PPdC/PPdU | 15% | 20 | 1.6 nM | 8 | 40% |
| | PPdC/NapdU | 18% | 17 | 3 nM | 10 | 59% |
| | PPdC/MOEdU | N.T. | N.T. | N.T. | N.T. | N.T. |
| | PPdC/TyrdU | 0% | 24 | 38.9 nM | 20 | 83% |
| | PPdC/ThrdU | N.T. | N.T. | N.T. | N.T. | N.T. |

Based on the information in table 11, the percent of all single modified aptamers assayed that showed no binding was 71%. No binding is defined as an aptamer having a Kd of 320 nM or greater. The percent of all single modified aptamers with a Kd≤10 nM was 12%, and the average Kd for all single modified aptamers was 12.3 nM. In contrast, the percent of all two modified (dual mod.) aptamers assayed that showed no binding was 54%. Further, the percent of all two modified aptamers with a Kd≤10 nM was 20%, and the average Kd for all two modified aptamers was 6.6 nM.

TABLE 12

Binding Data Summary for Single and Dual Modified Aptamers for ERBB2
ERBB2 Target

| Category | 5-Position Modification Of Aptamer | % of Aptamers Tested with a Kd ≤ 10 nM | Total # of Aptamers Tested | Kd for Aptamer with Greatest Affinity for Target | Total # of Aptamers with no Binding | % of Aptamers with no Binding |
|---|---|---|---|---|---|---|
| Control (unmodified) | dC/dT | N.T. | N.T. | N.T. | N.T. | N.T. |
| Single Mod. | NapdC/dT | 0% | 23 | 13.5 nM | 12 | 52% |
| | PPdC/dT | 7% | 15 | 7.8 nM | 8 | 53% |
| | dCNapdU | N.T. | N.T. | N.T. | N.T. | N.T. |
| | dC/PPdU | N.T. | N.T. | N.T. | N.T. | N.T. |
| | dC/MOEdU | N.T. | N.T. | N.T. | N.T. | N.T. |
| | dC/TyrdU | 0% | 29 | 24.1 nM | 27 | 93% |
| | dC/ThrdU | N.T. | N.T. | N.T. | N.T. | N.T. |
| Two Mod. | NapdC/NapdU | N.T. | N.T. | N.T. | N.T. | N.T. |
| | NapdC/PPdU | N.T. | N.T. | N.T. | N.T. | N.T. |
| | NapdC/MOEdU | N.T. | N.T. | N.T. | N.T. | N.T. |
| | NapdC/TyrdU | 28% | 32 | 0.65 nM | 10 | 31% |
| | NapdC/ThrdU | N.T. | N.T. | N.T. | N.T. | N.T. |
| | PPdC/PPdU | N.T. | N.T. | N.T. | N.T. | N.T. |
| | PPdC/NapdU | N.T. | N.T. | N.T. | N.T. | N.T. |
| | PPdC/MOEdU | N.T. | N.T. | N.T. | N.T. | N.T. |
| | PPdC/TyrdU | 20% | 20 | 0.74 nM | 13 | 65% |
| | PPdC/ThrdU | N.T. | N.T. | N.T. | N.T. | N.T. |

Based on the information in table 12, the percent of all single modified aptamers assayed that showed no binding was 70%. No binding is defined as an aptamer having a Kd of 320 nM or greater. The percent of all single modified aptamers with a Kd≤10 nM was less than 2%, and the average Kd for all single modified aptamers was 15.1 nM. In contrast, the percent of all two modified (dual mod.) aptamers assayed that showed no binding was 44%. Further, the percent of all two modified aptamers with a Kd≤10 nM was 25%, and the average Kd for all two modified aptamers was 0.7 nM.

TABLE 13

Binding Data Summary for Single and Dual Modified Aptamers for ERBB3 ERB133 Target

| Category | 5-Position Modification Of Aptamer | % of Aptamers Tested with a Kd ≤ 10 nM | Total # of Aptamers Tested | Kd for Aptamer with Greatest Affinity for Target | Total # of Aptamers with no Binding | % of Aptamers with no Binding |
|---|---|---|---|---|---|---|
| Control (unmodified) | dC/dT | N.T. | N.T. | N.T. | N.T. | N.T. |
| Single Mod. | NapdC/dT | 75% | 28 | 0.035 nM | 5 | 18% |
| | PPdC/dT | 0% | 12 | 17.5 nM | 3 | 25% |
| | dC/NapdU | N.T. | N.T. | N.T. | N.T. | N.T. |
| | dC/PPdU | N.T. | N.T. | N.T. | N.T. | N.T. |
| | dC/MOEdU | N.T. | N.T. | N.T. | N.T. | N.T. |
| | dC/TyrdU | 17% | 23 | 0.35 nM | 16 | 70% |
| | dC/ThrdU | N.T. | N.T. | N.T. | N.T. | N.T. |
| Two Mod. | NapdC/NapdU | N.T. | N.T. | N.T. | N.T. | N.T. |
| | NapdC/PPdU | N.T. | N.T. | N.T. | N.T. | N.T. |
| | NapdC/MOEdU | N.T. | N.T. | N.T. | N.T. | N.T. |
| | NapdC/TyrdU | 69% | 39 | 0.02 nM | 10 | 26% |
| | NapdC/ThrdU | N.T. | N.T. | N.T. | N.T. | N.T. |
| | PPdC/PPdU | N.T. | N.T. | N.T. | N.T. | N.T. |
| | PPdC/NapdU | N.T. | N.T. | N.T. | N.T. | N.T. |
| | PPdC/MOEdU | N.T. | N.T. | N.T. | N.T. | N.T. |
| | PPdC/TyrdU | 69% | 35 | 0.02 nM | 8 | 23% |
| | PPdC/ThrdU | N.T. | N.T. | N.T. | N.T. | N.T. |

Based on the information in table 13, the percent of all single modified aptamers assayed that showed no binding was 38%. No binding is defined as an aptamer having a Kd of 320 nM or greater. The percent of all single modified aptamers with a Kd≤10 nM was 40%, and the average Kd for all single modified aptamers was 6 nM. In contrast, the percent of all two modified (dual mod.) aptamers assayed that showed no binding was 24%. Further, the percent of all two modified aptamers with a Kd≤10 nM was 69%, and the average Kd for all two modified aptamers was 0.02 nM.

Example 7

Further Aptamers Comprising Two Modified Bases

Libraries comprising each of the modification pairs shown in Table 14 are made as follows. In some embodiments, each library contains 40 or more randomized nucleotides. In some embodiments, each library contains 30 randomized nucleotides, allowing for ≥$10^{15}$ different sequences. The libraries may be enzymatically synthesized using natural and/or modified nucleotide triphosphates using KOD DNA polymerase, Exo-. In some embodiments, the random region is flanked with fixed sequences for hybridizing PCR amplification primers, with or without additional spacers at the 5' end and at the 3' end. In some instances, the master synthetic template is used to generate modified libraries with all dU and or dC positions uniformly modified in replacement primer extension reactions. The library synthesis may be performed substantially as described in Example 1.

TABLE 14

Dual modified aptamer libraries

| | Library |
|---|---|
| 1 | dC/dT (DNA Control) |
| 2 | Nap-dC/dT |
| 3 | 2Nap-dC/dT |

TABLE 14-continued

Dual modified aptamer libraries

| | Library |
|---|---|
| 4 | PP-dC/dT |
| 5 | Tyr-dC/dT |
| 6 | dC/Nap-dU |
| 7 | dC/2Nap-dU |
| 8 | dC/PPdU |
| 9 | dC/Trp-dU |
| 10 | dC/Tyr-dU |
| 11 | Nap-dC/Nap-dU |
| 12 | Nap-dC/2Nap-dU |
| 13 | Nap-dC/PP-dU |
| 14 | Nap-dC/Trp-dU |
| 15 | Nap-dC/Tyr-dU |
| 16 | 2Nap-dC/Nap-dU |
| 17 | 2Nap-dC/2Nap-dU |
| 18 | 2Nap-dC/PP-dU |
| 19 | 2Nap-dC/Trp-dU |
| 20 | 2Nap-dC/Tyr-dU |
| 21 | PP-dC/Nap-dU |
| 22 | PP-dC/2Nap-dU |
| 23 | PP-dC/PP-dU |
| 24 | PP-dC/Trp-dU |
| 25 | PP-dC/Tyr-dU |
| 26 | Tyr-dC/Nap-dU |
| 27 | Tyr-dC/2Nap-dU |
| 28 | Tyr-dC/PP-dU |
| 29 | Tyr-dC/Trp-dU |
| 30 | Tyr-dC/Tyr-dU |

One or more of the libraries in Table 14 may be used to select aptamers that bind to a target, such as a protein target. The libraries comprising two modified bases typically yield aptamers having greater specificity and/or affinity for the target.

Example 8

Exemplary Dual-Modified Aptamers

PCSK9-binding aptamers of the conserved sequence family from pool 11720 (Nap-dC/dT) are shown in Table 15. Only the random region of each sequence is shown. The number of copies of each sequence (identical or equivalent with up to 5 mismatches) out of 11,380 total sequences is indicated. All Aaptamers in this family share the conserved sequence element TTppGGpp, where p=Nap-dC. Aptamer 11730-6 (SEQ ID No: 4, Kd=0.1 nM) was the representative chosen from this pool for the metabolic stability assay.

TABLE 15

Aptamers from pool 11720

| SEQ ID No | Copies | Random Region Sequence |
|---|---|---|
| 4 | 401 | AAG TTppGGpp GppTpGGGGTpppTGppAA |
| 5 | 21 | ATAppTGGGA TTppGGpp ATTTGpGpAGTT |
| 6 | 4 | TGAAG TTppGGpp GTGpGpATGGTApppAT |
| 7 | 3 | TTTGTGp TTppGGpp TAGpGpAGATATppT |
| 8 | 1 | ATAGG TTppGGpp TTGpGpTGTTTAGApA |
| 9 | 1 | TAGATGppTGGTAT TTppGGpp TTGpGpAT |
| 10 | 2 | TAGTGpppTGATpTA TTppGGpp AAGpppA |
| 11 | 3 | TTTGppppTGGTTApG TTppGGpp TGGpGpA |
| 12 | 2 | ATGppG TTppGGpp TAGpGpTpGTTApppA |
| 13 | 1 | TGAppAppTGTppAA TTppGGpp TAGpGpA |
| 14 | 1 | TAppAGGTA TTppGGpp GAGpGpTGpTATA |
| 15 | 1 | GAGpppAGTTAp TTppGGpp TTGpATTGTA |
| 16 | 1 | AAGAGT TTppGGpp TAppGpATTpApppT |
| 17 | 1 | ApAGTpppApAGTTTAA TTppGGpp GTAGppGpT |
| 18 | 1 | ATAppAGGGTpG TTppGGpp AAGpGpTGTT |
| 19 | 1 | GAG TTppGGpp TAGpGpAGAAGpppTGGAT |
| 20 | 1 | TTTTppAGGAA TTppGGpp AAGpGpTGTGA |
| 21 | 1 | AATTAppTGAGGA TTppGGpp AAGpGpAGA |
| 22 | 1 | pTGpGTTApGpp TTppGGpp TGGpTGATAG |
| 23 | 1 | TAppTGAGTTATGTA TTppGGpp GTGpGpA |
| 24 | 1 | pAAAGpA TTppGGpp TTGpGpAGTAGpppT |
| 25 | 1 | GTAGTTppAGATTGA TTppGGpp TTGpGpT |
| 26 | 1 | AATApTppAGGTGAG TTppGGpp AAGpGpT |

PCSK9-binding aptamers of the conserved sequence family from pool 11730 (Nap-dC/Tyr-dU) are shown in Table 16. Only the random region of each sequence is shown. The number of copies of each sequence (identical or equivalent with up to 5 mismatches) out of 17,695 total sequences is indicated. All aptamers in this family share the conserved sequence element yGpppG, where p=Nap-dC and Y=Tyr-dU. Many sequences also contained the conserved sequence element yyAyGpAp. Aptamer 11730-19 (SEQ ID No: 27, $K_d$=0.2 nM) was the representative chosen from this pool for the metabolic stability assay.

TABLE 16

Aptamers from pool 11730

| SEQ ID No | Copies | Random Region Sequence | | |
|---|---|---|---|---|
| 27 | 680 | GyyAypGpAAyGyGpGpppGGG | yGpppG | pp |
| 28 | 163 | yG | yGpppG | GAyAyyAApyGyyppGAGpAGy |
| 29 | 56 | yGyyyAyGpApA | yGpppG | pGAyGApAGyAA |
| 30 | 44 | AGyGyGAyyAyGpApy | yGpppG | pAyyyGGy |
| 31 | 15 | yAyAGAApAyAAyGpApA | yGpppG | pAyApy |
| 32 | 15 | yAypAGyyyAyGpApG | yGpppG | pGAyGApy |
| 33 | 13 | GApyApGAGGGAyGAyGpApA | yGpppG | pAy |
| 34 | 11 | AyAAyGAyyAyGpApA | yGpppG | pAyGypAy |
| 35 | 4 | GGpAypGyG | yGpppG | AyyyypyAAppGGGA |
| 36 | 4 | GppGAAyyyAyGpApp | yGpppG | pAyGAyyp |
| 37 | 2 | ppAAypAyGApApA | yGpppG | GAyGAyApy |
| 38 | 1 | yApGA | yGpppG | GAyAyyGApyGyyppGypG |
| 39 | 1 | pGyAGpGApGGGpGyGGpA | yGpppG | Gppppp |
| 40 | 1 | yGGyGAGAG | yGpppG | GAyAyyAApyGyypp |
| 41 | 1 | ypAAAGGppGyG | yGpppG | AyyyypyAAppG |
| 42 | 1 | yyypGAAGyyGAGpGyGGpAAyApy | yGppp | |
| 43 | 1 | pGyGyyyAyGpApy | yGpppG | pGAyyApApp |

PCSK9-binding aptamers of the conserved sequence family from pool 11733 (Pp-dC/Nap-dU) are shown in Table 17. Only the random region of each sequence is shown. The number of copies of each sequence (identical or equivalent with up to 5 mismatches) out of 16,118 total sequences is indicated. All aptamers in this family share the conserved sequence element rPPPAAGGrrPAPPG (SEQ ID NO: 83), where r=Pp-dC and P=Nap-dU. Aptamer 11733-44 (SEQ ID NO: 44, SL1063) was the most potent 30-mer inhibitor of wild-type human PCSK9 ($IC_{50}$=2.8 nM). Aptamer 11733-198 (SEQ ID No: 46, $K_d$=0.07 nM) was the representative chosen from this pool for the metabolic stability assay.

TABLE 17 aptamers from pool 11733

| SEQ ID No | Copies | Random Region Sequence | | |
|---|---|---|---|---|
| 44 | 1041 | AArGpA | rpppAAGGrrpAppG | AGGAAArpr |
| 45 | 969 | rA | rpppAAGArrpAppG | rGGAGArrrpGGG |
| 46 | 340 | rGpG | rpppAAGArrpGppG | AGApGrGrprA |
| 47 | 204 | A | rpppAAGArrpGppG | AGGGrrprGGGAAp |

TABLE 17-continued aptamers from pool 11733

| SEQ ID No | Copies | Random Region Sequence |
|---|---|---|
| 48 | 158 | GrrGGp GpppAAGAArpGppG GGGrArppr |
| 49 | 154 | GrGrA rpppAAGArrpAppG GGGAGAArpr |
| 50 | 127 | pppAAGGrrpGppG AGGArrprGGrApGAA |
| 51 | 105 | rAA rpppAAGGrrpGppG GGAGAGrrrppG |
| 52 | 51 | GAApArrArG rpppAAGArrpAppG GAprG |
| 53 | 23 | GAGAA rpppAAGArrpAppG AGGGrrprpG |
| 54 | 13 | rGA rpppAAGGrrpAppG GGGGArprGAr |
| 55 | 11 | GAArA rpppAAGArrpGppG GGAAGrGprp |
| 56 | 10 | A rpppAAGGrrpGppG AGGAAArrGprpGA |
| 57 | 10 | AG rpppAAGArrpGppG AGAApprGArAAA |
| 58 | 8 | AG rpppAAGArrpGppG AGrAGrrprGArr |
| 59 | 7 | GAAGGprAAGpGGrA rpppAAGGrrpGppr |
| 60 | 7 | AAArrA rpppAAGArrpGppG GGGrArprp |
| 61 | 6 | AAAr rpppAAGArrpAppG AGGpGGGrprA |
| 62 | 6 | pAGGrG rpppAAGArrpAppG AGGGArprr |
| 63 | 4 | GpGArG rpppAAGArrpAppA GGGrArppr |
| 64 | 3 | GAAArrA rpppAAGArrpAppG AGAGArpr |
| 65 | 3 | GAAA rpppAAGArrpAppG AGrAGGAArpr |
| 67 | 3 | rGA rpppAAGArrpGppG AAAGprGrGGGG |
| 68 | 3 | A rpppAAGArrpGppG AGArrGGrprGGArAp |
| 69 | 2 | GAA rpppAAGArrpGppG AGGArrAprArG |
| 70 | 2 | ArGpGGAGprGGArA rpppAAGGrrpGppr |
| 71 | 2 | prGrGA rpppAAGGrrpAppG pGGGArprp |
| 72 | 2 | G rpppAAGGrrpAppG AGAprGGrpGGGp |
| 73 | 2 | GA rpppAAGGrrpGppG AAGGprGAGAGpp |
| 74 | 2 | AArGAp rpppAAGGrrpGppA GGGGrppr |
| 75 | 2 | rAAGrpGrrprGrA rpppAAGArGpGppG G |
| 76 | 2 | ArrGp GpppAAGAArpGppG GGGGGAArpr |
| 77 | 1 | GAApArrArG rpppAAGArrpAppG AGApGrGrprA |
| 78 | 1 | pAAGrrpGAGAAArrA rpppAAGArrpppp |
| 79 | 1 | rGAA rpppAAGArrpGppG AGrAGrprppr |
| 80 | 1 | AGAAp rpppAAGGrrpGprG AGArrprGAG |

The invention claimed is:

1. An aptamer comprising at least one first 5-position modified pyrimidine and at least one second 5-position modified pyrimidine, wherein the first 5position modified pyrimidine and the second 5-position modified pyrimidine are different 5position modified pyrimidines;

wherein the first 5position modified pyrimidine is a 5position modified uridine and wherein the second 5position modified pyrimidine is a 5position modified cytidine; or wherein the first 5position modified pyrimidine is a 5position modified cytidine and wherein the second 5position modified pyrimidine is a 5position modified uridine;

wherein the 5position modified uridine comprises a moiety at the 5position selected from a naphthyl moiety, a benzyl moiety, a tyrosyl moiety, an indole moiety and a morpholino moiety; and wherein the 5-position modified cytidine comprises a moiety at the 5position selected from a naphthyl moiety, a benzyl moiety, a tyrosyl moiety, and a morpholino moiety.

2. The aptamer of claim 1, wherein the 5-position modified cytidine is selected from a NapdC, a 2NapdC, a TyrdC, and a PPdC.

3. The aptamer of claim 1, wherein the 5-position modified uridine is selected from a NapdU, a 2NapdU, a PPdU, a MOEdU, a TyrdU, a TrpdU, and a ThrdU.

4. The aptamer of claim 1, wherein the 5-position modified cytidine is a NapdC and the 5-position modified uridine is selected from a NapdU, a 2NapdU, a PPdU, a MOEdU, a TyrdU, and a ThrdU.

5. The aptamer of claim 1, wherein the 5-position modified cytidine is a PPdC and the 5-position modified uridine is selected from a NapdU, a 2NapdU, a PPdU, a MOEdU, a TyrdU, and a ThrdU.

6. The aptamer of claim 4, wherein the 5-position modified uridine is a TyrdU.

7. The aptamer of claim 1, wherein the aptamer is 20 to 100, or 20 to 90, or 20 to 80, or 20 to 70, or 20 to 60, or 20 to 50, or 30 to 100, or 30 to 90, or 30 to 80, or 30 to 70, or 30 to 60, or 30 to 50, or 40 to 100, or 40 to 90, or 40 to 80, or 40 to 70, or 40 to 60, or 40 to 50 nucleotides in length.

8. A composition comprising a plurality of polynucleotides, wherein each polynucleotide comprises at least one first 5-position modified pyrimidine and at least one second 5-position modified pyrimidine, wherein the first 5-position modified pyrimidine and the second 5-position modified pyrimidine are different 5-position modified pyrimidines;
wherein the first 5-position modified pyrimidine is a 5-position modified uridine and wherein the second 5-position modified pyrimidine is a 5-position modified cytidine; or
wherein the first 5-position modified pyrimidine is a 5-position modified cytidine and wherein the second 5-position modified pyrimidine is a 5-position modified uridine;
wherein the 5-position modified uridine comprises a moiety at the 5-position selected from a naphthyl moiety, a benzyl moiety, a tyrosyl moiety, an indole moiety and a morpholino moiety; and
wherein the 5-position modified cytidine comprises a moiety at the 5-position selected from a naphthyl moiety, a benzyl moiety, a tyrosyl moiety, and a morpholino moiety.

9. The composition of claim 8, wherein each polynucleotide comprises a fixed region at the 5' end and/or the 3' end of the polynucleotide.

10. The composition of claim 8, wherein the 5-position modified cytidine is selected from NapdC, 2NapdC, TyrdC, and PPdC.

11. The composition of claim 8, wherein the 5-position modified uridine is selected from NapdU, 2NapdU, PPdU, MOEdU, TyrdU, TrpdU, and ThrdU.

12. The composition of any one of claim 8, wherein each polynucleotide comprises a random region.

13. A composition comprising an aptamer and a target, wherein the aptamer and the target are capable of forming a complex, and wherein the aptamer is an aptamer of claim 1.

14. A composition comprising a first aptamer, a second aptamer, and a target,
wherein the first aptamer comprises at least one first 5-position modified pyrimidine and at least one second 5-position modified pyrimidine;
wherein the second aptamer comprises at least one third 5-position modified pyrimidine or wherein the second aptamer comprises at least one third 5-position modified pyrimidine and at least one fourth 5-position modified pyrimidine;
wherein the first aptamer, second aptamer and the target are capable of forming a trimer complex; and
wherein the first 5-position modified pyrimidine and the second 5-position modified pyrimidine are different 5-position modified pyrimidines; and
wherein the first aptamer is an aptamer of any one of claim 1.

15. The composition of claim 14, wherein the target is selected from a protein, a peptide, a carbohydrate, a small molecule, a cell and a tissue.

16. A method comprising:
(a) contacting an aptamer capable of binding to a target molecule with a sample;
(b) incubating the aptamer with the sample to allow an aptamer-target complex to form;
(c) enriching for the aptamer-target complex in the sample and
(c) detecting for the presence of the aptamer, aptamer-target complex or target molecule, wherein the detection of the aptamer, aptamer-target complex or target molecule indicates that the target molecule is present in the sample, and wherein the lack of detection of the aptamer, aptamer-target complex or target molecule indicates that the target molecule is not present in the sample;
wherein the aptamer is an aptamer of claim 1.

17. The method of claim 16, wherein the sample is selected from whole blood, leukocytes, peripheral blood mononuclear cells, plasma, serum, sputum, breath, urine, semen, saliva, meningial fluid, amniotic fluid, glandular fluid, lymph fluid, nipple aspirate, bronchial aspirate, synovial fluid, joint aspirate, cells, a cellular extract, stool, tissue, a tissue biopsy, and cerebrospinal fluid.

18. A method for detecting a target in a sample comprising
a) contacting the sample with a first aptamer to form a mixture, wherein the first aptamer is capable of binding to the target to form a first complex;
b) incubating the mixture under conditions that allow for the first complex to form;
c) contacting the mixture with a second aptamer, wherein the second aptamer is capable of binding the first complex to form a second complex;
d) incubating the mixture under conditions that allow for the second complex to form;
e) detecting for the presence or absence of the first aptamer, the second aptamer, the target, the first complex or the second complex in the mixture, wherein the presence of the first aptamer, the second aptamer, the target, the first complex or the second complex indicates that the target is present in the sample;
wherein the first aptamer is an aptamer of any one of claim 1;
wherein the second aptamer comprises at least one third 5-position modified pyrimidine, or wherein the second aptamer comprises at least one third 5-position modified pyrimidine and at least one fourth 5-position modified pyrimidine.

19. The method of claim 18, wherein the first aptamer, second aptamer and the target are capable of forming a trimer complex.

* * * * *

UNITED STATES PATENT AND TRADEMARK OFFICE
CERTIFICATE OF CORRECTION

PATENT NO. : 10,927,380 B2  
APPLICATION NO. : 16/307520  
DATED : February 23, 2021  
INVENTOR(S) : Jeff Carter et al.

Page 1 of 1

It is certified that error appears in the above-identified patent and that said Letters Patent is hereby corrected as shown below:

In the Claims

In Claim 1, at Column 85, Line 60, "5position" should read --5-position--;

In Claim 1, at Column 85, Line 62, "5position" should read --5-position--;

In Claim 1, at Column 85, Line 64, both instances of "5position" should read --5-position--;

In Claim 1, at Column 85, Line 65, "5position" should read --5-position--;

In Claim 1, at Column 85, Line 66, "5position" should read --5-position--;

In Claim 1, at Column 86, Line 56, both instances of "5position" should read --5-position--;

In Claim 1, at Column 86, Line 57, "5position" should read --5-position--;

In Claim 1, at Column 86, Line 58, "5position" should read --5-position--;

In Claim 1, at Column 86, Line 60, "5position" should read --5-position--;

In Claim 1, at Column 86, Line 61, "5position" should read --5-position--;

In Claim 1, at Column 86, Line 65, "5position" should read --5-position--;

In Claim 4, at Column 87, Line 7, "5 -position" should read --5-position--;

In Claim 14, at Column 88, Line 9, delete "any one of";

In Claim 18, at Column 88, Line 54, delete "any one of".

Signed and Sealed this  
Eleventh Day of May, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 83

<210> SEQ ID NO 1
<211> LENGTH: 79

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (34)..(63)
<223> OTHER INFORMATION: a, c, t, g, unknown or other

<400> SEQUENCE: 1 aattttttt  ctctttctct  tctctctttc  tccnnnnnnn  nnnnnnnnnn  nnnnnnnnnn    60
nnngacccac  ccagcgtgg                                                    79

<210> SEQ ID NO 2
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
atatatatcc  acgctgggtg  ggtc                                             24

<210> SEQ ID NO 3
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3 aattttttt  ctctttctct  tctctctttc  tcc                                   33

<210> SEQ ID NO 4
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
aagttccggc  cgcctcgggg  tccctgccaa                                       30

<210> SEQ ID NO 5
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
atacctggga  ttccggccat  ttgcgcagtt                                       30

<210> SEQ ID NO 6
<211> LENGTH: 30
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 6
tgaagttccg gccgtgcgca tggtacccat                                            30

<210> SEQ ID NO 7
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
tttgtgcttc cggcctagcg cagatatcct                                            30

<210> SEQ ID NO 8
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
ataggttccg gccttgcgct gtttagaca                                             29

<210> SEQ ID NO 9
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
tagatgcctg gtatttccgg ccttgcgcat                                            30

<210> SEQ ID NO 10
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
tagtgccctg atctattccg gccaagccca                                            30

<210> SEQ ID NO 11
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
tttgcccctg gttacgttcc ggcctggcgc a                                          31
```

-continued

```
<210> SEQ ID NO 12
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
atgccgttcc ggcctagcgc tcgttaccca                                    30

<210> SEQ ID NO 13
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
tgaccacctg tccaattccg gcctagcgca                                    30

<210> SEQ ID NO 14
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
taccaggtat tccggccgag cgctgctata                                    30

<210> SEQ ID NO 15
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
gagcccagtt acttccggcc ttgcattgta                                    30

<210> SEQ ID NO 16
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
aagagtttcc ggcctaccgc attcaccct                                     29

<210> SEQ ID NO 17
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 17
acagtcccac agtttaattc cggccgtagc cgct                                34

<210> SEQ ID NO 18
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ataccagggt cgttccggcc aagcgctgtt                                     30

<210> SEQ ID NO 19
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
gagttccggc ctagcgcaga agccctggat                                     30

<210> SEQ ID NO 20
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
ttttccagga attccggcca agcgctgtga                                     30

<210> SEQ ID NO 21
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
aattacctga ggattccggc caagcgcaga                                     30

<210> SEQ ID NO 22
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
ctgcgttacg ccttccggcc tggctgatag                                     30

<210> SEQ ID NO 23
<211> LENGTH: 30
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 23
tacctgagtt atgtattccg gccgtgcgca                                              30

<210> SEQ ID NO 24
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
caaagcattc cggccttgcg cagtagccct                                              30

<210> SEQ ID NO 25
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
gtagttccag attgattccg gccttgcgct                                              30

<210> SEQ ID NO 26
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
aatactccag gtgagttccg gccaagcgct                                              30

<210> SEQ ID NO 27
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
guuaucgcaa ugugcgcccg ggugcccgcc                                              30

<210> SEQ ID NO 28
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ugugcccgga uauuaacugu uccgagcagu                                              30
```

```
<210> SEQ ID NO 29
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
uguuuaugca caugcccgcg augacaguaa                                           30

<210> SEQ ID NO 30
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
agugugauua ugcacuugcc cgcauuuggu                                           30

<210> SEQ ID NO 31
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
uauagaacau aaugcacaug cccgcauacu                                           30

<210> SEQ ID NO 32
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
uaucaguuua ugcacgugcc cgcgaugacu                                           30

<210> SEQ ID NO 33
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
gacuacgagg gaugaugcac augcccgcau                                           30

<210> SEQ ID NO 34
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 34
auaaugauua ugcacaugcc cgcaugucau                                    30

<210> SEQ ID NO 35
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
ggcaucgugu gcccgauuuu cuaaccggga                                    30

<210> SEQ ID NO 36
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
gccgaauuua ugcaccugcc cgcaugauuc                                    30

<210> SEQ ID NO 37
<211> LENGTH: 29
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
ccaaucauga cacaugcccg gaugauacu                                     29

<210> SEQ ID NO 38
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
uacgaugccc ggauauugac uguuccgucg                                    30

<210> SEQ ID NO 39
<211> LENGTH: 31
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
cguagcgacg ggcguggcau gcccggcccc c                                  31

<210> SEQ ID NO 40
<211> LENGTH: 30
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
uggugagagu gcccggauau uaacuguucc                                      30

<210> SEQ ID NO 41
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
ucaaaggccg ugugcccgau uuucuaaccg                                      30

<210> SEQ ID NO 42
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
uuucgaaguu gagcguggca auacuugccc                                      30

<210> SEQ ID NO 43
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
cguguuuaug cacuugcccg cgauuacacc                                      30

<210> SEQ ID NO 44
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
aacguacuuu aaggccuauu gaggaaacuc                                      30

<210> SEQ ID NO 45
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
cacuuuaaga ccuauugcgg agacccuggg                                      30
```

<210> SEQ ID NO 46
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 46
cgugcuuuaa gaccuguuga gaugcgcuca                                            30

<210> SEQ ID NO 47
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 47
acuuuaagac cuguugaggg ccucgggaau                                            30

<210> SEQ ID NO 48
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 48
gccgguguuu aagaacuguu ggggcacuuc                                            30

<210> SEQ ID NO 49
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 49
gcgcacuuua agaccuauug gggagaacuc                                            30

<210> SEQ ID NO 50
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 50
uuuaaggccu guugaggacc ucggcaugaa                                            30

<210> SEQ ID NO 51
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 51
caacuuuaag gccuguuggg agagcccuug                              30

<210> SEQ ID NO 52
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
gaauaccacg cuuuaagacc uauuggaucg                              30

<210> SEQ ID NO 53
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
gagaacuuua agaccuauug agggccucug                              30

<210> SEQ ID NO 54
<211> LENGTH: 29
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
cgacuuuaag gccuauuggg ggacucgac                               29

<210> SEQ ID NO 55
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
gaacacuuua agaccuguug ggaagcgucu                              30

<210> SEQ ID NO 56
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
acuuuaaggc cuguugagga aaccgucuga                              30

<210> SEQ ID NO 57
<211> LENGTH: 30

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
agcuuuaaga ccuguugaga auucgacaaa                                    30

<210> SEQ ID NO 58
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
agcuuuaaga ccuguugagc agccucgacc                                    30

<210> SEQ ID NO 59
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
gaaggucaag uggcacuuua aggccuguuc                                    30

<210> SEQ ID NO 60
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
aaaccacuuu aagaccuguu ggggcacucu                                    30

<210> SEQ ID NO 61
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
aaaccuuuaa gaccuauuga ggugggcuca                                    30

<210> SEQ ID NO 62
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
```
uaggcgcuuu aagaccuauu gagggacucc            30

<210> SEQ ID NO 63
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
gugacgcuuu aagaccuauu agggcacuuc            30

<210> SEQ ID NO 64
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
gaaaccacuu uaagaccuau ugagagacuc            30

<210> SEQ ID NO 65
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
gaaacuuuaa gaccuauuga gcaggaacuc            30

<210> SEQ ID NO 66

<400> SEQUENCE: 66

000

<210> SEQ ID NO 67
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
cgacuuuaag accuguugaa agucgcgggg            30

<210> SEQ ID NO 68
<211> LENGTH: 32
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
acuuuaagac cuguugagac cggcucggac au          32

<210> SEQ ID NO 69
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
gaacuuuaag accuguugag gaccaucacg                                    30

<210> SEQ ID NO 70
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
acguggaguc ggacacuuua aggccuguuc                                    30

<210> SEQ ID NO 71
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ucgcgacuuu aaggccuauu gugggacucu                                    30

<210> SEQ ID NO 72
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
gcuuuaaggc cuauugagau cggcucgggu                                    30

<210> SEQ ID NO 73
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
gacuuuaagg ccuguugaag gucgagaguu                                    30

<210> SEQ ID NO 74
<211> LENGTH: 29
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 74
aacgaucuuu aaggccuguu aggggcuuc                                29

<210> SEQ ID NO 75
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
caagcugccu cgcacuuuaa gacguguugg                               30

<210> SEQ ID NO 76
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
accguguuua agaacuguug gggggaacuc                               30

<210> SEQ ID NO 77
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
gaauaccacg cuuuaagacc uauugagaug cgcuca                        36

<210> SEQ ID NO 78
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
uaagccugag aaaccacuuu aagaccuuuu                               30

<210> SEQ ID NO 79
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
cgaacuuuaa gaccuguuga gcagcucuuc                               30

<210> SEQ ID NO 80
<211> LENGTH: 30
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
agaaucuuua aggccugucg agaccucgag                                          30

<210> SEQ ID NO 81
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="May or may not be present"
<220> FEATURE:
<221> NAME/KEY: misc_feature
<222> LOCATION: (15)..(15)
<223> OTHER INFORMATION: /note="May or may not be present"
<220> FEATURE:
<221> NAME/KEY: source
<223> OTHER INFORMATION: /note="See specification as filed for detailed
      description of substitutions and preferred embodiments"

<400> SEQUENCE: 81
scccaagrmc crccv                                                          15

<210> SEQ ID NO 82
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
aattttttt                                                                 10

<210> SEQ ID NO 83
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
cuuuaaggcc uauug                                                          15
```